US007521416B2

(12) United States Patent
McBride et al.

(10) Patent No.: US 7,521,416 B2
(45) Date of Patent: *Apr. 21, 2009

(54) D-AMINO ACID PEPTIDES

(75) Inventors: William J. McBride, Boonton, NJ (US); David M. Goldenberg, Mendham, NJ (US)

(73) Assignee: Immunomedics, Inc., Morris Plains, NJ (US)

( * ) Notice: Subject to any disclaimer, the term of this patent is extended or adjusted under 35 U.S.C. 154(b) by 14 days.

This patent is subject to a terminal disclaimer.

(21) Appl. No.: 11/640,557

(22) Filed: Dec. 18, 2006

(65) Prior Publication Data

US 2007/0142296 A1 Jun. 21, 2007

Related U.S. Application Data

(63) Continuation of application No. 10/866,180, filed on Jun. 14, 2004, now Pat. No. 7,172,751.

(60) Provisional application No. 60/478,403, filed on Jun. 13, 2003.

(51) Int. Cl.
A61K 38/00 (2006.01)
(52) U.S. Cl. .......................................................... 514/2
(58) Field of Classification Search ........................ None
See application file for complete search history.

(56) References Cited

U.S. PATENT DOCUMENTS

| 4,735,210 | A |   | 4/1988  | Goldenberg         |
|-----------|---|---|---------|--------------------|
| 4,863,713 | A |   | 9/1989  | Goodwin            |
| 5,101,827 | A |   | 4/1992  | Goldenberg         |
| 5,128,119 | A |   | 7/1992  | Griffiths          |
| 5,256,395 | A |   | 10/1993 | Barbet             |
| 5,274,076 | A |   | 12/1993 | Barbet             |
| 5,328,679 | A |   | 7/1994  | Hansen             |
| 5,697,902 | A |   | 12/1997 | Goldenberg         |
| 5,746,996 | A |   | 5/1998  | Govindan           |
| 5,753,206 | A |   | 5/1998  | McBride et al.     |
| 5,772,981 | A |   | 6/1998  | Govindan et al.    |
| 5,776,093 | A |   | 7/1998  | Goldenberg         |
| 5,776,094 | A |   | 7/1998  | Goldenberg         |
| 5,776,095 | A |   | 7/1998  | Goldenberg         |
| 6,010,680 | A |   | 1/2000  | Govindan et al.    |
| 6,071,490 | A | * | 6/2000  | Griffiths et al. ............ 424/1.49 |
| 6,077,499 | A |   | 6/2000  | Griffiths et al.   |
| 6,120,768 | A |   | 9/2000  | Griffiths et al.   |
| 6,126,916 | A |   | 10/2000 | McBride et al.     |
| 6,558,669 | B1 |  | 5/2003  | Govindan et al.    |
| 6,663,866 | B1 |  | 12/2003 | Govindan           |
| 6,962,702 | B2 |  | 11/2005 | Hansen et al.      |
| 7,011,816 | B2 |  | 3/2006  | Griffiths          |
| 7,052,872 | B1 |  | 5/2006  | Hansen et al.      |
| 7,172,751 | B2 | * | 2/2007 | McBride et al. ............ 424/9.34 |
| 2002/0006379 | A1 |  | 1/2002 | Hansen et al.    |
| 2003/0026764 | A1 |  | 2/2003 | Griffiths        |
| 2003/0124057 | A1 |  | 7/2003 | Griffiths et al. |
| 2003/0176784 | A1 |  | 9/2003 | Griffiths et al. |
| 2003/0198595 | A1 |  | 10/2003 | Goldenberg et al. |
| 2003/0220470 | A1 |  | 11/2003 | Govindan         |
| 2003/0235534 | A1 |  | 12/2003 | Griffiths et al. |
| 2004/0022726 | A1 |  | 2/2004 | Goldenberg et al. |
| 2004/0057902 | A1 |  | 3/2004 | Gold et al.      |
| 2004/0235065 | A1 |  | 11/2004 | Hansen et al.   |
| 2005/0014297 | A1 |  | 1/2005 | Nejad            |
| 2006/0104899 | A1 |  | 5/2006 | Hansen et al.    |

FOREIGN PATENT DOCUMENTS

| WO | WO01/77342 A1 | 10/2001 |
| WO | 2004/029093   | 4/2004  |

OTHER PUBLICATIONS

Barbet, J. et al., "Radioimmunodetection of Medullary Thyroid Carcinoma Using Indium-111 Bivalent Hapten and Anti-CEA X Anti-DTPA-Indium Bispecific Antibody," J. Nucl. Med. 39:1172-1178 (1998).
Boden et al., "Preliminary Study of the Metal Binding Site of an Anti-DTPA-Indium Antibody by equilibrium binding Immunoassays and Immobilized Metal Ion Affinity Chromatography," Bioconjugate Chem., 6:373-379 (1995).
Gautherot, E., et al., "Therapy for Colon Carcinoma Xenografts with Bi-Specific Antibody-Targeted, Iodine-131-Labeled Bivalent Hapten," Cancer Supp., 80:2618-2623 (1997).
Gautherot, E. et al., "Radioimmunotherapy of LS147T Colon Carcinoma in Nude Mice Using an Iodine-131-Labeled Bivalent Hapten Combined with an Anti-CEA X Anti-Indium-DTPA Bispecific Antibody," J. Nucl. Med. Suppl., 38 (1997).
Goodwin, D.A. et al., "Pre-Targeted Immunoscintigraphy of Murine Tumors with Indium-111-labeled Bifunctional Haptens," J. Nucl. Med., 29:226-234 (1988).
Zoller, M. et al., "Establishment and Characterization of Monoclonal Antibodies Against an Octahedral Gallium Chelate Suitable for Immunoscintigraphy with PET," J. Nucl. Med., 33:1366-1372 (1992).

(Continued)

Primary Examiner—Cecilia Tsang
Assistant Examiner—Thomas S Heard
(74) Attorney, Agent, or Firm—Richard A. Nakashima

(57) ABSTRACT

The present invention provides compounds of the formula X—$R^1$-D-[Dpr, Orn or Lys](A)-$R^2$(Z)-D-[Dpr, Orn or Lys](B)—$R^3$(Y)—$NR^4R^5$; or $R^1$(X)-D-[Dpr, Orn or Lys](A)-$R^2$(Z)-D-[Dpr, Orn or Lys](B)—$R^3$(Y)—$NR^4R^5$, in which X is a hard acid cation chelator, a soft acid cation chelator or Ac—, $R^1$, $R^2$ and $R^3$ are independently selected from a covalent bond or one or more D-amino acids that can be the same or different, Y is a hard acid cation chelator, a soft acid cation chelator or absent, Z is a hard acid cation chelator, a soft acid cation chelator or absent, and A and B are haptens or hard acid cation chelators and can be the same or different, and $R^4$ and $R^5$ are independently selected from the group consisting of hard acid cation chelators, soft acid cation chelators, enzymes, therapeutic agents, diagnostic agents and H. The present invention also provides methods of using these compounds and kits containing the compounds.

19 Claims, 18 Drawing Sheets

OTHER PUBLICATIONS

Kranenborg, M.H. et al., "Development and Characterization of Anti-Renal Cell Carcinoma x Antichelate Bispecific Monoclonal Antibodies for Two-Phase Targeting of Renal Cell Carcinoma," Cancer Res. (Suppl.) 55, 5864-5867 (Dec. 1, 1995).

Kranenborg, M. et al., "The Effect of Antibody Protein Dose of Anti-Renal Cell Carcinoma Monoclonal Antibodies in Nude Mice with Renal Cell Carcinoma Xenografts," Cancer (Suppl.) 80:2390-2397 (1997).

Schuhmacher, J. et al., "Multistep Tumor Targeting in Nude Mice Using Bispecific Antibodies and a Gallium Chelate Suitable for Immunoscintigraphy with Positron Emission Tomography," Cancer Res., 55, 115-123 (1995).

Sharkey, R.M., "Development of a Streptavidin-Anti-Carcinoembryonic Antigen Antibody, Radiolabeled Biotin Pretargeting Method for Radioimmunotherapy of Colorectal Cancer. Studies in a Human Colon Cancer Xenograft Model," Bioconjugate Chem., 8:595-604 (1997).

Stickney, D.R. et al., "Bifunctional Antibody: A Binary Radiopharmaceutical Delivery System for Imaging Colorectal Carcinoma," Cancer Res. 51:6650-6655 (Dec. 15, 1991).

Chetanneau et al. "Pretargetted imaging of colorectal cancer recurrences using an 111In-labelled bivalent hapten and a bispecific antibody conjugate", Nuclear Medicine Communications (1994), 15, 972-980.

Drug Facts and Comparisons, 2000, p. 1967 and p. 2003.

Gruaz-Guyon et al. "Radiolabled bivalent haptens for tumor immunodetection and radioimmunotherapy", Q J Nucl. Med. 2001; 45:201-6.

Karacay et al. "Pretargeting for Cancer Radioimmunotherapy with Bispecific Antibodies: Role of the Bispecific Antibody's Valency for the Tumor Target Antigen", Bioconjugate Chem., 2002, 13 (5), 1054-1070.

Janevik-Ivanovska et al. "Bivalent Hapten-Bearing Peptides Designed for Iodine-131 Pretargeted Radioimmunotherapy", Bioconjugate Chem., 1997, 8 (4), 526-533.

Office Action issued Jan. 27, 2009 in U.S. Appl. No. 11/640,790.

* cited by examiner

D-AMINO ACID PEPTIDES

CROSS-REFERENCE TO RELATED APPLICATIONS

This application is a continuation of U.S. Patent Application Publ. No.20050025709, Ser. No. 10/866,180 (now issued U.S. Pat. No. 7,172,751), filed Jun. 14, 2004, which claimed the benefit under 35 U.S.C. §119(e) of U.S. Provisional Patent Application No. 60/478,403, filed Jun. 13, 2003, the entire contents of each incorporated herein by reference.

BACKGROUND

1. Field of the Invention

The invention relates to immunological reagents for therapeutic use, for example, in radioimmunotherapy (RAIT), and diagnostic use, for example, in radioimmunodetection (RAID) and magnetic resonance imaging (MRI). This application claims priority to provisional patent application 60/478,403, filed Jun. 13, 2003, the contents of which are hereby incorporated by reference in their entirety. The contents of U.S. Ser. No. 60/090,142 and U.S. Ser. No. 60/104, 156 also are incorporated herein by reference in their entireties.

2. Related Art

An approach to cancer therapy and diagnosis involves directing antibodies or antibody fragments to disease tissues, wherein the antibody or antibody fragment can target a diagnostic agent or therapeutic agent to the disease site. One approach to this methodology which has been under investigation, involves the use of bsAbs having at least one arm that specifically binds a targeted diseased tissue and at least one other arm that specifically binds a low molecular weight hapten. In this methodology, a bsAb is administered and allowed to localize to target, and to clear normal tissue. Some time later, a radiolabeled low molecular weight hapten is given, which being recognized by the second specificity of the bsAb, also localizes to the original target.

Although low MW haptens used in combination with bsAbs possess a large number of specific imaging and therapy uses, it is impractical to prepare individual bsAbs for each possible application. Further, the application of a bsAb/low MW hapten system has to contend with several other issues. First, the arm of the bsAb that binds to the low MW hapten must bind with high affinity, since a low MW hapten is designed to clear the living system rapidly, when not bound by bsAb. Second, the non-bsAb-bound low MW hapten actually needs to clear the living system rapidly to avoid non-target tissue uptake and retention. Third, the detection and/or therapy agent must remain associated with the low MW hapten throughout its application within the bsAb protocol employed.

Of interest with this approach are bsAbs that direct chelators and metal chelate complexes to cancers using Abs of appropriate dual specificity. The chelators and metal chelate complexes used are often radioactive, using radionuclides such as cobalt-57 (Goodwin et al., U.S. Pat. No. 4,863,713), indium-111 (Barbet et al., U.S. Pat. No. 5,256,395 and U.S. Pat. No. 5,274,076, Goodwin et al., *J. Nucl. Med.*, 33:1366-1372 (1992), and Kranenborg et al., *Cancer Res* (suppl.), 55:5864s-5867s (1995) and *Cancer* (suppl.) 80:2390-2397 (1997)) and gallium-68 (Boden et al., *Bioconjugate Chem.*, 6:373-379, (1995) and Schuhmacher et al., *Cancer Res.*, 55:115-123 (1995)) for radioimmuno-imaging. Because the Abs were raised against the chelators and metal chelate complexes, they have remarkable specificity for the complex against which they were originally raised. Indeed, the bsAbs of Boden et al. have specificity for single enantiomers of enantiomeric mixtures of chelators and metal-chelate complexes. This great specificity has proven to be a disadvantage in one respect, in that other nuclides such as yttrium-90 and bismuth-213 useful for radioimmunotherapy (RAIT), and gadolinium useful for MRI, cannot be readily substituted into available reagents for alternative uses. As a result iodine-131, a non-metal, has been adopted for RAIT purposes by using an I-131-labeled indium-metal-chelate complex in the second targeting step. A second disadvantage to this methodology requires that antibodies be raised against every agent desired for diagnostic or therapeutic use.

Pretargeting methodologies have received considerable attention for cancer imaging and therapy. Unlike direct targeting systems where an effector molecule (e.g., a radionuclide or a drug linked to a small carrier) is directly linked to the targeting agent, in pretargeting systems, the effector molecule is given some time after the targeting agent. This allows time for the targeting agent to localize in tumor lesions and, more importantly, clear from the body. Since most targeting agents have been antibody proteins, they tend to clear much more slowly from the body (usually days) than the smaller effector molecules (usually in minutes). In direct targeting systems involving therapeutic radionuclides, the body, and in particular the highly vulnerable red marrow, is exposed to the radiation all the while the targeting agent is slowly reaching its peak levels in the tumor and clearing from the body. In a pretargeting system, the radionuclide is usually bound to a small "effector" molecule, such as a chelate or peptide, which clears very quickly from the body, and thus exposure of normal tissues is minimized. Maximum tumor uptake of the radionuclide is also very rapid because the small molecule efficiently transverses the tumor vasculature and binds to the primary targeting agent. Its small size may also encourage a more uniform distribution in the tumor.

Pretargeting methods have used a number of different strategies, but most often involve an avidin/streptavidin-biotin recognition system or bispecific antibodies that co-recognize a tumor antigen and the effector molecule. The avidin/streptavidin system is highly versatile and has been used in several configurations. Antibodies can be coupled with streptavidin or biotin, which is used as the primary targeting agent.

This is followed sometime later by the effector molecule, which conjugated with biotin or with avidin/streptavidin, respectively. Another configuration relies on a 3-step approach first targeting a biotin-conjugated antibody, followed by a bridging with streptavidin/avidin, and then the biotin-conjugated effector is given. These systems can be easily converted for use with a variety of effector substances so long as the effector and the targeting agent can be coupled with biotin or streptavidin/avidin depending on the configuration used. With its versatility for use in many targeting situations and high binding affinity between avidin/streptavidin and biotin, this type of pretargeting has considerable advantages over other proposed systems. However, avidin and streptavidin are foreign proteins and therefore would be immunogenic, which would limit the number of times they could be given in a clinical application. In this respect, bsAbs have the advantage of being able to be engineered as a relatively non-immunogenic humanized protein. Although the binding affinity of a bsAb (typically $10^{-9}$ to $10^{-10}$ M) cannot compete with the extremely high affinity of the streptavidin/avidin-biotin affinity ($\sim 10^{-15}$ M), both pretargeting systems are dependent on the binding affinity of the primary targeting agent, and therefore the higher affinity of the streptavidin/avidin-biotin systems may not offer a substantial advantage over a bsAb pretargeting system. However, most bsAbs have only one arm available for binding the primary target, whereas the streptavidin/avidin-biotin pretargeting systems have typically used a whole IgG with two arms for binding the target, which strengthens target binding. By using a divalent peptide, an affinity enhancement is achieved, which greatly improves the binding of the peptide to the target site compared to a monovalent peptide. Thus, both systems are likely to provide excellent targeting ratios with reasonable retention.

Pretargeting with a bsAb also requires one arm of the antibody to recognize an effector molecule. Most radionuclide targeting systems reported to date have relied on an antibody to a chelate-metal complex, such as antibodies directed indium-loaded DTPA or antibodies to other chelates. Since the antibody is generally highly selective for this particular chelate-metal complex, new bsAbs would need to be constructed with the particular effector antibody. This could be avoided if the antibody was not specific to the effector, but instead reacted with another substance. In this way, a variety of effectors could be made so long as they also contained the antibody recognition substance. We have continued to develop the pretargeting system originally described by Janevik-Ivanovska et al. that used an antibody directed against a histamine derivative, histamine-succinyl-glycl (HSG) as the recognition system on which a variety of effector substances could be prepared. Excellent pretargeting results have been reported using a radioiodinated and a rhenium-labeled divalent HSG-containing peptide. In this work, we have expanded this system to include peptides suitable for radiolabeling $^{90}$Y, $^{111}$In, and $^{177}$Lu, as well as an alternative $^{99m}$Tc-binding peptide.

Thus, there is a continuing need for immunological agents which can be directed to diseased tissue and can specifically bind to a subsequently administered targetable diagnostic or therapeutic conjugate, and a flexible system that accommodates different diagnostic and therapeutic agents without alteration to the bi-specific or multi-specific antibodies.

In accomplishing the present invention, the present inventors have discovered that it is advantageous to raise multi-specific Abs against a targetable construct that is capable of carrying one or more diagnostic or therapeutic agents. By utilizing this technique, the characteristics of the chelator, metal chelate complex, therapeutic agent or diagnostic agent can be varied to accommodate differing applications, without raising new multi-specific Abs for each new application. Further, by using this approach, two or more distinct chelators, metal chelate complexes, diagnostic agents or therapeutic agents can be used with the inventive multi-specific Ab.

SUMMARY OF THE INVENTION

One embodiment of the present invention provides a compound comprising the formula:

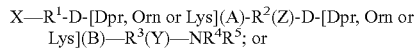

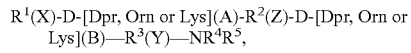

wherein:

X is a hard acid cation chelator, a soft acid cation chelator, an enzyme, a therapeutic agent, a diagnostic agent, or Ac—;

$R^1$ is a covalent bond or one or more D-amino acids that can be the same or different;

$R^2$ is a covalent bond or one or more D-amino acids that can be the same or different;

$R^3$ is a covalent bond or one or more D-amino acids that can be the same or different;

Y is a hard acid cation chelator, a soft acid cation chelator, an enzyme, a therapeutic agent, a diagnostic agent or absent;

Z is a hard acid cation chelator, a soft acid cation chelator, an enzyme, a therapeutic agent, a diagnostic agent, or absent;

A and B are haptens or hard acid cation chelators and can be the same or different; and $R^4$ and $R^5$ are independently selected from the group consisting of hard acid cation chelators, soft acid cation chelators, enzymes, therapeutic agents, diagnostic agents and H. In the present formula Dpr is 2,3-diaminoproprionic acid. In some of these embodiments, when $R^1$ or $R^3$ is a covalent bond then the other $R^1$ or $R^3$ can be one or more D-amino acids that can be the same or different. In these and other embodiments, $R^2$ can be one or more D-amino acids that can be the same or different. In still other of these embodiments, the compound can comprise the formula X—$R^1$-D-Lys(A)-$R^2$-D-Lys(B)—$R^3$(Y)—NR$^4$R$^5$. In some of these embodiments R is a single D-amino acid. In other embodiments, $R^2$ is two D-amino acids that can be the same or different. In further embodiments, $R^3$ is a D-Lys and Y is a hard acid cation chelator or a soft acid cation chelator. In some of these embodiments $R^2$ is not a D-Lys. In still further embodiments A and B are independently selected from the group consisting of histamine-succinyl-glycine (HSG), DTPA and fluorescein isothiocyanate. In yet other embodiments, $R^1$ is one or more D-amino acids that can be the same or different, $R^2$ is one or more D-amino acids that can be the same or different, $R_3$ is a covalent bond, Y is absent, and A and B are haptens or hard acid cation chelators and can be the same or different. In additional embodiments A and B are haptens and can be the same or different. In these and other embodiments $R^1$ and $R^2$ are single D-amino acids and can be the same or different. When $R^1$ is more than one amino acid then one, any or all of the amino acids can be attached to the (X) group. Similarly, when $R^2$ is more than one amino acid then one, any or all of the amino acids can be attached to the (Z) group. In some embodiments, Z is absent. In some embodiments, only one or two of X, Y, Z $R^4$ or $R^5$ is an enzyme, a therapeutic agent or a diagnostic agent. Parentheses indicate substituents on the amino acid side chain. If the molecules are in the main chain of the peptide then they are not surrounded by parentheses.

In additional embodiments $R^1$ is selected from the group consisting of D-Tyr, D-Ala, D-Ser, D-Thr, D-Cys, D-Leu, D-Ile, D-Met, D-Gln, D-Asn, D-Val, and D-Phe. In additional embodiments R1 is selected from the group consisting of D-Pro, D-His, D-Trp, D-Glu, D-Asp, D-Arg, and D-Lys. In these and other embodiments, $R^2$ is selected from the group consisting of D-Asp, D-Glu and D-Tyr. In some of the embodiments described herein $R^4$ and $R^5$ are both H. In other embodiments, one of X, $R^4$ and $R^5$ is a hard acid cation chelator. In these and other embodiments, one of the remaining X, $R^4$ and $R^5$ is a soft acid cation chelator. In some embodiments, X is a hard acid cation chelator. In additional embodiments, one of $R^4$ and $R^5$ is a hard acid cation chelator. In some embodiments, the hard acid cation chelator comprises a carboxylate or amine group. In yet further embodiments the hard acid cation chelator is selected from the group consisting of NOTA, DOTA, DTPA, and TETA. In still other embodiments, one of X, $R^4$ and $R^5$ is a soft acid cation chelator, which can comprise a thiol group. The soft acid cation chelator can be selected from the group consisting of Tscg-Cys and Tsca-Cys. In some of the present compounds one of $R^4$ and $R^5$ is a soft acid cation chelator and the remaining $R^4$ or $R^5$ is H.

In certain embodiments, X is Ac—, A and B are hard acid cation chelators and can be the same or different, $R^3$ is a covalent bond, and Y is absent. In some embodiments, X is Ac—, A and B are haptens and can be the same or different, $R^1$ is a covalent bond, and Y is a soft acid cation chelator. Specific embodiments of the present compounds include:

DOTA-D-Asp-D-Lys(HSG)-D-Asp-D-Lys(HSG)-NH$_2$ (IMP 271);

DOTA-D-Glu-D-Lys(HSG)-D-Glu-D-Lys(HSG)-NH$_2$ (IMP 277);

DOTA-D-Tyr-D-Lys(HSG)-D-Glu-D-Lys(HSG)-NH$_2$ (IMP 288);

DOTA-D-Ala-D-Lys(HSG)-D-Glu-D-Lys(HSG)-NH$_2$ (IMP 281);

DOTA-D-Phe-D-Lys(HSG)-D-Tyr-D-Lys(HSG)-NH$_2$ (IMP 284)

DOTA-D-Lys(HSG)-D-Glu-D-Lys(HSG)-D-Tyr-D-Lys(HSG)-NH2 (IMP 301)

DOTA-D-Lys(HSG)-D-Ala-D-Lys(HSG)-D-Glu-D-Lys(HSG)-D-Tyr-D-Lys(HSG)-NH2 (IMP 302)

DOTA-D-Tyr-D-Lys(HSG)-D-Glu-D-Lys(HSG)-D-Cys-NH2 (IMP 305)

Ac-D-Lys(In-DTPA)-D-Tyr-D-Lys(In-DTPA)-D-Lys(Tscg-Cys)-NH2 MH+1813 (IMP 297)

HCO—CO-D-Lys(HSG)-D-Glu-D-Lys(HSG)-NH2 (IMP 289); and

Ac-D-Lys(DTPA)-D-Tyr-D-Lys(DTPA)-D-Lys(TscG-Cys)-NH$_2$; and

Ac-D-Lys(DOTA)-D-Tyr-D-Lys(DOTA)-D-Lys(TscG-Cys)-NH$_2$.

In these and other embodiments the compounds can further comprise at least one radionuclide. Examples of suitable radionuclides include $^{225}$Ac, $^{111}$Ag, $^{72}$As, $^{77}$As, $^{211}$At, $^{198}$Au, $^{199}$Au, $^{212}$Bi, $^{213}$Bi, $^{75}$Br, $^{76}$Br, $^{11}$C, $^{55}$Co, $^{62}$Cu, $^{64}$Cu, $^{67}$Cu, $^{166}$Dy, $^{169}$Er, $^{18}$F, $^{52}$Fe, $^{59}$Fe, $^{67}$Ga, $^{68}$Ga, $^{154}$Gd, $^{155}$Gd, $^{156}$Gd, $^{157}$Gd, $^{158}$Gd, $^{166}$Ho, $^{120}$I, $^{123}$I, $^{124}$I, $^{125}$I, $^{131}$I, $^{110}$In, $^{111}$In, $^{194}$Ir, $^{177}$Lu, $^{51}$Mn, $^{52m}$Mn, $^{99}$Mo, $^{13}$N, $^{15}$O, $^{32}$P, $^{33}$P, $^{211}$Pb, $^{212}$Pb, $^{109}$Pd, $^{149}$Pm, $^{142}$Pr, $^{143}$Pr, $^{223}$Ra, $^{82m}$Rb, $^{186}$Re, $^{188}$Re, $^{189}$Re, $^{105}$Rh, $^{47}$SC, $^{153}$Sm, $^{75}$Se, $^{83}$Sr, $^{89}$Sr, $^{161}$Tb, $^{94m}$Tc, $^{94}$Tc, $^{99m}$Tc, $^{86}$Y, $^{90}$Y, $^{90}$Y, and $^{89}$Zr.

In some of the present compounds the hard acid cation chelator is chelated to a cation selected from the group consisting of Group IIa and Group IIIa metal cations. In these and other embodiments the soft acid cation chelator is chelated to a cation selected from the group consisting of transition metals, Bi, lanthanides and actinides. Suitable cations include Tc, Re, and Bi.

In still other embodiments the present compounds $R^4$ or $R^5$ is a therapeutic agent, diagnostic agent or enzyme. In these embodiments, the therapeutic agent, diagnostic agent or enzyme can be covalently linked to the compound by a linker

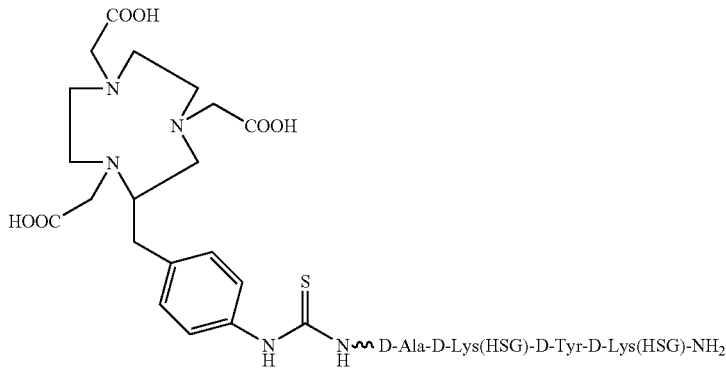

In some embodiments of the present compounds, (i) no more than one of X, $R^4$ and $R^5$ is a hard acid cation chelator and (ii) no more than one of X, $R^4$ and $R^5$ is a soft acid cation chelator. Additional specific examples of the present compounds include:

Ac-D-Phe-D-Lys(DOTA)-D-Tyr-D-Lys(DOTA)-NH$_2$;

Ac-D-Phe-D-Lys(DTPA)-D-Tyr-D-Lys(DTPA)-NH$_2$;

Ac-D-Phe-D-Lys(Bz-DTPA)-D-Tyr-D-Lys(Bz-DTPA)-NH$_2$

Ac-D-Lys(HSG)-D-Tyr-D-Lys(HSG)-D-Lys(Tscg-Cys)-NH$_2$;

DOTA-D-Phe-D-Lys(HSG)-D-Tyr-D-Lys(HSG)-D-Lys(Tscg-Cys)-NH$_2$;

(Tscg-Cys)-D-Phe-D-Lys(HSG)-D-Tyr-D-Lys(HSG)-D-Lys(DOTA)-NH$_2$;

Tscg-D-Cys-D-Glu-D-Lys(HSG)-D-Glu-D-Lys(HSG)-NH$_2$;

(Tscg-Cys)-D-Glu-D-Lys(HSG)-D-Glu-D-Lys(HSG)-NH$_2$;

Ac-D-Cys-D-Lys(DOTA)-D-Tyr-D-Ala-D-Lys(DOTA)-D-Cys-NH$_2$;

Ac-D-Cys-D-Lys(DTPA)-D-Tyr-D-Lys(DTPA)-NH$_2$;

moiety. In some embodiments, the linker moiety can comprise at least one amino acid. Suitable therapeutic agents for use in the present invention include a drug, prodrug or toxin. Prodrugs can be selected from the group consisting of epirubicin glucuronide, CPT-11, etoposide glucuronide, daunomicin glucuronide and doxorubicin glucuronide. Toxins can be selected from the group consisting of ricin, abrin, ribonuclease (RNase), DNase I, Staphylococcal enterotoxin-A, pokeweed antiviral protein, gelonin, diphtherin toxin, *Pseudomonas* exotoxin, and *Pseudomonas* endotoxin. The therapeutic agent can comprises doxorubicin, SN-38, camptothecin, etoposide, methotrexate, 6-mercaptopurine or etoposide phosphate. The diagnostic agent can comprise one or more agents for photodynamic therapy, for example a photosensitizer, such as a benzoporphyrin monoacid ring A (BPD-MA), tin etiopurpurin (SnET2), sulfonated aluminum phthalocyanine (AlSPc) and lutetium texaphyrin (Lutex). Other suitable diagnostic agents can comprise one or more image enhancing agents for use in magnetic resonance imaging (MRI), such as Mn, Fe, La or Gd. The diagnostic agent can also comprise one or more radiopaque or contrast agents for X-ray or computed tomography, such as barium, diatrizoate, ethiodized oil, gallium citrate, iocarmic acid, iocetamic acid, iodamide, iodipamide, iodoxamic acid, iogulamide, iohexol, iopamidol, iopanoic acid, ioprocemic acid, iosefamic acid, ioseric acid, iosulamide meglumine, iosemetic acid, iotasul, iotetric acid, iothalamic acid, iotroxic acid, ioxaglic acid, ioxotrizoic acid, ipodate, meglumine, metrizamide, metrizoate, propyliodone, or thallous chloride. The diagnostic agent can also comprises one or more ultrasound contrast agents, for example a liposome or dextran. In some embodiments the liposome can be gas-filled. In some embodiments an enzyme that is capable of converting a drug intermediate to a toxic form to increase toxicity of the drug at a target site can be included in the compound.

In some of the present compounds the amino acid backbone can have a length of 2 to about 50, 75, 85 or 100 contigous amino acids. For example $R^1$ or $R^3$ can be from about 1, 2, 5, 10 or 15 amino acids t about 20, 25, 30 or 35 amino acids in length. In certain compounds the amino acid chain will be 3, 4, 5, 6, 7, 8, 9 or 10 amino acids in length. In certain embodiments, $R^2$ is 1, 2, or 3 amino acids in length. In some embodiments, the present invention also provides a targetable construct comprising any of the present compounds. In some of the present compounds, the amino acid backbone is cyclic, while in others it is linear.

Another embodiment of the present invention provides methods of diagnosing, treating or both diagnosing and treating a disease or a condition that can lead to a disease comprising:

(A) administering a targetable construct comprising any of the present compounds to a subject having, or suspected of having, a disease or a condition, wherein the targetable construct comprises at least one diagnostic or therapeutic cation, and/or one or more chelated or chemically bound therapeutic agents, diagnostic agents, or enzymes; and (B) administering a multispecific antibody or antibody fragment to the subject, wherein the multispecific antibody or antibody fragment has at least one arm that specifically binds a targeted tissue and at least one other arm that specifically binds the targetable construct. These methods can further comprise:

(C) administering a clearing composition to the subject, wherein the clearing composition enhances clearance of non-localized antibodies or antibody fragments from the subject. In the present methods the targetable construct and the multispecific antibody or antibody fragment can be administered at substantially the same time.

Suitable examples of therapeutic cations used in the present methods can emit particles and/or positrons having 20 to 10,000 keV, for example $^{111}$In, $^{177}$Lu, $^{212}$Bi, $^{213}$I, $^{211}$At, $^{62}$Cu, $^{64}$Cu, $^{67}$Cu, $^{90}$Y, $^{125}$I, $^{131}$I, $^{32}$P, $^{33}$P, $^{47}$Sc, $^{111}$Ag, $^{67}$Ga, $^{142}$Pr, $^{153}$Sm, 161Tb, $^{166}$Dy, $^{166}$Ho, $^{186}$Re, $^{188}$Re, $^{189}$Re, $^{212}$Pb, $^{223}$Ra, $^{225}$Ac, $^{59}$Fe, 75S, $^{77}$As, $^{89}$Sr, $^{99}$Mo, 105Rh, $^{109}$Pd, $^{143}$Pr, $^{149}$Pm, $^{169}$Er, $^{194}$Ir, $^{198}$Au, $^{199}$Au and $^{211}$Pb. In other embodiments the diagnostic cation emits particles and/or positrons having 25-10,000 keV, such as $^{110}$In, $^{111}$In, $^{177}$Lu, $^{18}$F, $^{52}$Fe, $^{62}$Cu, $^{64}$Cu, $^{67}$Cu, $^{67}$Ga, $^{68}$Ga, $^{86}$Y, $^{90}$Y, $^{89}$Zr, $^{94}$mTc, $^{94}$Tc, $^{99}$mTc, $^{120}$I, $^{123}$I, $^{124}$I, $^{125}$I, $^{131}$I, $^{154-158}$Gd, $^{32}$P, $^{11}$C, $^{13}$N, $^{15}$O, $^{186}$Re, $^{188}$Re, $^{51}$Mn, $^{52}$mMn, $^{55}$Co, $^{72}$As, $^{75}$Br, $^{76}$Br, $^{82}$mRb and $^{83}$Sr.

In some of the present methods, the diagnostic cation or agent is used in positron-emission tomography (PET) or SPECT imaging. In other embodiments, the diagnostic cation or agent comprises one or more image enhancing agents used in magnetic resonance imaging (MRI), for example Mn, Fe, La and Gd. In other methods the diagnostic agent comprises one or more radiopaque or contrast agents for X-ray or computed tomography, for example comprises barium, diatrizoate, ethiodized oil, gallium citrate, iocarmic acid, iocetamic acid, iodamide, iodipamide, iodoxamic acid, iogulamide, iohexol, iopamidol, iopanoic acid, ioprocemic acid, iosefamic acid, ioseric acid, iosulamide meglumine, iosemetic acid, iotasul, iotetric acid, iothalamic acid, iotroxic acid, ioxaglic acid, ioxotrizoic acid, ipodate, meglumine, metrizamide, metrizoate, propyliodone, or thallous chloride. In yet additional methods the diagnostic agent comprises one or more ultrasound contrast agents, for example a liposome or dextran. In some methods, the liposome is gas-filled.

In additional methods, the one or more diagnostic agents are selected from the group consisting of fluorescent compounds, chemiluminescent compounds, and bioluminescent compounds. Suitable fluorescent compounds include fluorescein isothiocyanate, rhodamine, phycoerytherin, phycocyanin, allophycocyanin, o-phthaldehyde and fluorescamine. Suitable chemiluminescent compounds include luminol, isoluminol, an aromatic acridinium ester, an imidazole, an acridinium salt and an oxalate ester. Suitable bioluminescent compounds a include luciferin, luciferase and aequorin.

In some embodiments of the present methods, the targeted tissue is a tumor. In some embodiments, the tumor produces or is associated with antigens selected from the group consisting of colon-specific antigen-p (CSAp), carcinoembryonic antigen (CEA), CD19, CD20, CD21, CD22, CD23, CD 25, CD30, CD74, CD80, HLA-DR, Ia, MUC 1, MUC 2, MUC 3, MUC 4, EGFR, HER 2/neu, PAM-4, TAG-72, EGP-1, EGP-2, A3, KS-1, Le(y), S100, PSMA, PSA, tenascin, folate receptor, VEGF, necrosis antigens, IL-2, T101, MAGE, IL-6, insulin-like growth factor receptor, carbonic anhydrase IX, and combinations thereof.

In other methods at least one arm that specifically binds the targeted tissue is a monoclonal antibody or a fragment of a monoclonal antibody. In still further methods, the at least one other arm that specifically binds the targetable construct is a monoclonal antibody or a fragment of a monoclonal antibody. In additional methods, the at least one arm that specifically binds the targeted tissue is a human, chimeric or humanized antibody or a fragment of a human, chimeric or humanized antibody. In additional methods, the at least one other arm that specifically binds the targetable construct is a human, chimeric or humanized antibody or a fragment of a human, chimeric or humanized antibody. In some of the methods, the multispecific antibody or antibody fragment further comprises a therapeutic nuclide, such as those selected from the group consisting of $^{111}$In, $^{177}$Lu, $^{212}$Bi, $^{213}$Bi, $^{211}$At, $^{62}$Cu, $^{64}$Cu, $^{67}$Cu, $^{90}$Y, $^{125}$I, $^{131}$I, $^{32}$P, $^{33}$P, $^{47}$Sc, $^{111}$Ag, $^{67}$Ga, $^{142}$Pr, $^{153}$Sm, $^{161}$Tb, $^{166}$Dy, $^{166}$Ho, $^{186}$Re, $^{188}$Re, $^{189}$Re, $^{212}$Pb, $^{223}$Ra, $^{25}$Ac, $^{59}$Fe, $^{75}$Se, $^{77}$As, $^{89}$Sr, $^{99}$Mo, $^{105}$Rh, $^{109}$Pd, $^{143}$Pr, $^{149}$Pm, $^{169}$Er, $^{194}$Ir, $^{198}$Au, $^{199}$Au and $^{211}$Pb.

In certain methods, the multispecific antibody comprises the Fv of MAb Mu-9 and the Fv of MAb 679. In some of these methods, Mu-9 and/or 679 are chimerized or humanized. In other of these methods, Mu-9 and/or 679 are human Mu9 and 679. In additional methods, the multispecific antibody comprises one or more of the CDRs of Mu-9. In some of the present methods, the multispecific antibody comprises one or more of the CDRs of 679. In some methods, the multispecific antibody is a fusion protein. In yet additional methods, the multispecific antibody comprises the Fv of MAb MN-14 and the Fv of MAb 679. In some of these methods, the MN-14, and/or 679 are chimerized or humanized. In other methods, the multispecific antibody comprises one or more of the CDRs of MN-14. In additional methods, the multispecific antibody comprises one or more of the CDRs of 679. In still further methods, the multispecific antibody is a fusion protein. In some of the present methods 9 the fusion protein is trivalent, and incorporates the Fv of an antibody reactive with CSAp. In some methods, the multispecific antibody incorporates a Class-III anti-CEA antibody and the Fv of 679.

In further methods disclosed herein the targetable construct comprises $^{10}$B atoms and the method further comprises:

(C) irradiating the $^{10}$B atoms localized at the targeted tissue, thereby effecting boron neutron capture therapy of the targeted tissue.

In additional methods, the targetable construct comprises an enzyme and the method further comprising:

(C) administering a drug to the subject, wherein the enzyme is capable of converting the drug a toxic form thereby increasing the toxicity of the drug at the targeted tissue.

In some of the present methods the disease or condition is selected from the group consisting of cancer, an infectious disease, an inflammatory disease, and autoimmune disease, cardiovascular disease, a metabolic disease, and a neurological disease. Examples of cancer include leukemias, lymphomas, sarcomas, melanomas, carcinomas, gliomas, and skin cancers. Specific examples of cancer include a B-cell malignancy, a B-cell lymphoma, chronic lymphatic leukemia, non-Hodgkin's lymphoma, acute lymphatic leukemias, or a multiple myeloma. Cancers that can be subjected to the present methods include esophageal, gastric, colonic, rectal, pancreatic, lung, breast, ovarian, urinary bladder, endometrial, cervical, testicular, renal, adrenal or liver cancer.

In some of the present methods the disease or condition is an infectious disease caused by a pathogen. Examples of pathogens include a fungus, virus, parasite, bacterium, protozoan, or mycoplasm. In some methods, the pathogen is a fungus selected from the group consisting of *Microsporum, Trichophyton, Epidermophyton, Sporothrix schenckii, Cyrptococcus neoformans, Coccidioides immitis, Histoplasma capsulatum, Blastomyces dermatitidis,* and *Candida albicans.* In other methods, the pathogen is a virus selected from the group consisting of human immunodeficiency virus (HIV), herpes virus, cytomegalovirus, rabies virus, influenza virus, hepatitis B virus, Sendai virus, feline leukemia virus, Reo virus, polio virus, human serum parvo-like virus, simian virus 40, respiratory syncytial virus, mouse mammary tumor virus, *Varicella-Zoster* virus, Dengue virus, rubella virus, measles virus, adenovirus, human T-cell leukemia viruses, Epstein-Barr virus, papilloma virus, murine leukemia virus, mumps virus, vesicular stomatitis virus, Sindbis virus, lymphocytic choriomeningitis virus, wart virus and blue tongue virus. In additional methods, the pathogen is a bacterium selected from the group consisting of *Anthrax bacillus, Streptococcus agalactiae, Legionella pneumophilia, Streptococcus pyogenes, Staphylococcus, Escherichia coli, Neisseria gonorrhoeae, Neisseria meningitidis,* Pneumococcus, Hemophilis influenzae B, *Treponema pallidum,* Lyme disease spirochetes, *Pseudomonas aeruginosa, Mycobacterium leprae, Brucella abortus, Mycobacterium tuberculosis* and *Clostridium tetani.*

In still further methods, the pathogen is a parasite selected from the group consisting of helminth and malarial parasites. In yet other methods, the pathogen is a protozoan selected from the group consisting of *Plasmodium falciparum, Plasmodium vivax, Toxoplasma gondii, Trypanosoma rangeli, Trypanosoma cruzi, Trypanosoma rhodesiensei, Trypanosoma brucei, Schistosoma mansoni, Schistosoma japanicum, Babesia bovis, Elmeria tenella, Onchocerca volvulus, Leishmania tropica, Trichinella spiralis, Onchocerca volvulus, Theileria parva, Taenia hydatigena, Taenia ovis, Taenia saginata, Echinococcus granulosus* and *Mesocestoides corti.* In yet further methods, the pathogen is a mycoplasm selected from the group consisting of *Mycoplasma arthritidis, Mycoplasma hyorhinis, Mycoplasma orale, Mycoplasma arginini, Acholeplasma laidlawii, Mycoplasma salivarum,* and *Mycoplasma pneumoniae.*

In some of the present methods, the disease or condition is an inflammatory disease or an autoimmune disease, such as acute idiopathic thrombocytopenic purpura, chronic idiopathic thrombocytopenic purpura, dermatomyositis, Sydenbam's chorea, myasthenia gravis, systemic lupus erythematosus, lupus nephritis, rheumatic fever, polyglandular syndromes, bullous pemphigoid, diabetes mellitus, Henoch-Schonlein purpura, post-streptococcalnephritis, erytbema nodosurn, Takayasu's arteritis, Addison's disease, rheumatoid arthritis, multiple sclerosis, sarcoidosis, ulcerative colitis, erythema multiforme, IgA nephropathy, polyarteritis nodosa, ankylosing spondylitis, Goodpasture's syndrome, thromboangitisubiterans, Sjögren's syndrome, primary biliary cirrhosis, Hashimoto's thyroiditis, thyrotoxicosis, scleroderma, chronic active hepatitis, polymyositis/dermatomyositis, polychondritis, pamphigus vulgaris, Wegener's granulomatosis, membranous nephropathy, amyotrophic lateral sclerosis, tabes dorsalis, giant cell arteritis/polymyalgia, pernicious anemia, rapidly progressive glomerulonephritis, psoriasis, and fibrosing alveolitis.

In other methods, the disease or condition is cardiovascular disease, such as a myocardial infarction, ischemic heart disease, atherosclerotic plaques, clots, and emboli. In additional methods, the disease or condition is a metabolic disease, such as amyloidosis. In further methods, the disease or condition is a neurological disease, such as Alzheimer's disease.

The present invention also provides methods for detecting, identifying or treating a target cell, tissue or pathogen in a subject, comprising:

(a) administering a targetable construct comprising any of the present compounds to a subject; and (b) administering a multispecific antibody or antibody fragment to the subject, wherein the multispecific antibody or antibody fragment comprises at least one arm that specifically binds a target cell, tissue or pathogen and at least one other arm that specifically binds the targetable construct. In some of these methods, the target comprises a molecule produced by or associated with the target cell, tissue, pathogen. In certain methods, the target tissue is a diseased tissue. The diseased tissue can be identified intraoperatively, endoscopically or intravascularly. In some methods, the target tissue is normal tissue, such as ovary, thymus, parathyroid, endometrium, bone marrow, or spleen. In additional methods, the pathogen is a fungus, virus, parasite, bacterium, protozoan, or mycoplasm. Examples of fungi include *Microsporum, Trichophyton, Epidermophyton, Sporothrix schenckii, Cyrptococcus neoformans, Coccidioides immitis, Histoplasma capsulatum, Blastomyces dermatitidis,* and *Candida albicans.* Examples of viri include human immunodeficiency virus (HIV), herpes virus, cytomegalovirus, rabies virus, influenza virus, hepatitis B virus, Sendai virus, feline leukemia virus, Reo virus, polio virus, human serum parvo-like virus, simian virus 40, respiratory syncytial virus, mouse mammary tumor virus, *Varicella-Zoster* virus, Dengue virus, rubella virus, measles virus, adenovirus, human T-cell leukemia viruses, Epstein-Barr virus, murine leukemia virus, mumps virus, vesicular stomatitis virus, Sindbis virus, lymphocytic choriomeningitis virus, wart virus and blue tongue virus. Examples of bacterium include *Anthrax bacillus, Streptococcus agalactiae, Legionella pneumophilia, Streptococcus pyogenes, Escherichia coli, Neisseria gonorrhoeae, Neisseria meningitidis,* Pneumococcus, Hemophilis influenzae B, *Treponema palli-* dum, Lyme disease spirochetes, *Pseudomonas aeruginosa, Mycobacterium leprae, Brucella abortus, Mycobacterium tuberculosis* and Tetanus toxin. Parasites can be a helminth or a malarial parasite. Examples of protozoa include *Plasmodium falciparum, Plasmodium vivax, Toxoplasma gondii, Trypanosoma rangeli, Trypanosoma cruzi, Trypanosoma rhodesiensei, Trypanosoma brucei, Schistosoma mansoni, Schistosoma japanicum, Babesia bovis, Elmeria tenella, Onchocerca volvulus, Leishmania tropica, Trichinella spiralis, Onchocerca volvulus, Theileria parva, Taenia hydatigena, Taenia ovis, Taenia saginata, Echinococcus granulosus* and *Mesocestoides corti*. Examples of mycoplasms include *Mycoplasma arthritidis, Mycoplasma hyorhinis, Mycoplasma orale, Mycoplasma arginini, Acholeplasma laidlawii, Mycoplasma salivarum*, and *Mycoplasma pneumoniae*.

In some of the present methods the targetable construct further comprises at least one radionuclide, therapeutic agent, diagnostic agent or enzyme. Examples of radionuclide can be $^{225}$Ac, $^{111}$Ag, $^{72}$As, $^{77}$As, $^{211}$At, $^{198}$Au, $^{199}$Au, $^{212}$Bi, $^{213}$Bi, $^{75}$Br, $^{76}$Br, $^{11}$C, $^{55}$Co, $^{62}$Cu, $^{64}$Cu, $^{67}$Cu, $^{166}$Dy, $^{169}$Er, $^{18}$F, $^{52}$Fe, $^{59}$Fe, $^{67}$Ga, $^{68}$Ga, $^{154}$Gd, $^{155}$Gd, $^{156}$Gd, $^{157}$Gd, $^{158}$Gd, $^{166}$Ho, $^{120}$I, $^{123}$I, $^{124}$I, $^{125}$I, $^{131}$I, $^{110}$In, $^{111}$In, $^{194}$Ir, $^{177}$Lu, $^{51}$Mn, $^{52}$mMn, $^{99}$Mo, $^{13}$N, $^{15}$O, $^{32}$P, $^{33}$P, $^{211}$Pb, $^{212}$Pb, $^{109}$Pd, $^{149}$Pm, $^{142}$Pr, $^{143}$Pr, $^{223}$Ra, $^{82}$mRb, $^{186}$Re, $^{188}$Re, $^{189}$Re, $^{105}$Rh, $^{47}$Sc, $^{153}$Sm, $^{75}$Se, $^{83}$Sr, $^{89}$Sr, $^{161}$Tb, $^{94}$mTc, $^{94}$Tc, $^{99}$mTc, $^{86}$Y, $^{90}$Y, $^{90}$Y, and $^{89}$Zr.

In some methods, the diagnostic agent comprises an imaging agent. In some of the disclosed methods, the method can further comprise:

(c) administering a clearing composition to the subject, wherein the composition enhances clearance of non-localized antibodies or antibody fragments from the subject. The present methods can be used to treat mammals, including humans, primates, equines, canines and felines. In some of the present methods, the therapeutic agent comprises one or more drugs, toxins, cytokines, hormones, or growth factors. In some methods, the diagnostic agent comprises a contrast agent. In additional methods, the imaging agent is an agent used for PET or SPECT. In some of the present methods, the multispecific antibody or antibody fragment is bispecific.

The present invention also provides kits for treating or identifying diseased tissues in a subject comprising:

(a) a targetable construct comprising one or more of the present compounds; and (b) a multispecific antibody or antibody fragment having at least one arm that specifically binds a targeted tissue and at least one other arm that specifically binds the targetable construct. The present kits can further comprise:

(c) a clearing composition for enhancing clearance of non-localized antibodies and antibody fragments. In some of these kits, the diagnostic agent selected from the group consisting of $^{110}$In, $^{111}$n, $^{177}$Lu, $^{18}$F, $^{52}$Fe, $^{62}$Cu, $^{64}$Cu, $^{67}$Cu, $^{67}$Ga, $^{68}$Ga, $^{86}$Y, $^{90}$Y, $^{89}$Zr, $^{94}$mTc, $^{94}$Tc, $^{99}$mTc, $^{120}$I, $^{123}$I, $^{124}$I, $^{125}$I, $^{131}$I, $^{154-158}$Gd, $^{32}$P, $^{11}$C, $^{13}$N, $^{15}$O, $^{186}$Re, $^{188}$Re, $^{51}$Mn, $^{52}$mMn, $^{55}$Co, $^{72}$As, $^{75}$Br, $^{76}$Br, $^{82}$mRb and $^{83}$Sr. In other kits, the therapeutic agent is selected from the group consisting of $^{111}$In, $^{177}$Lu, $^{212}$Bi, $^{213}$Bi, $^{211}$At, $^{62}$Cu, $^{64}$CU, $^{67}$Cu, $^{90}$Y, $^{125}$I, $^{131}$I, $^{32}$P, $^{33}$P, $^{47}$SC, $^{67}$Ga, $^{142}$Pr, $^{153}$SM, $^{161}$Tb, $^{166}$Dy, $^{166}$Ho, $^{186}$Re, $^{188}$Re, $^{189}$Re, $^{212}$Pb, $^{223}$Ra, $^{225}$Ac, $^{59}$Fe, $^{75}$Se, $^{77}$As, $^{89}$Sr, $^{99}$Mo, $^{105}$Rh, $^{109}$Pd, $^{143}$Pr, $^{149}$Pm, $^{169}$Er, $^{194}$Ir, $^{198}$Au, $^{199}$Au and $^{211}$Pb.

In some of the above kits, when the targetable construct comprises an enzyme the kit further comprises a drug which the enzyme is capable of converting to a toxic form to increase the toxicity of the drug.

The present invention can also provide a multi-specific or bi-specific antibody or antibody fragment having at least one arm that specifically binds a targeted tissue and at least one other arm that specifically binds a targetable construct.

In the present methods, when the targetable construct comprises an enzyme, the methods can further comprise administering to the patient 1) a prodrug, when the enzyme is capable of converting the prodrug to a drug at the target site;

2) a drug which is capable of being detoxified in the patient to form an intermediate of lower toxicity, when the enzyme is capable of reconverting the detoxified intermediate to a toxic form, and, therefore, of increasing the toxicity of the drug at the target site, 3) a prodrug which is activated in the patient through natural processes and is subject to detoxification by conversion to an intermediate of lower toxicity, when the enzyme is capable of reconverting the detoxified intermediate to a toxic form, and, therefore, of increasing the toxicity of the drug at the target site, or 4) a second targetable construct which comprises a carrier portion which comprises or bears at least one epitope recognizable by the at least one other arm of the bi-specific antibody or antibody fragment, and a prodrug, when the enzyme is capable of converting the prodrug to a drug at the target site.

In another embodiment, kits can further comprise, when the first targetable construct comprises an enzyme, 1) a prodrug, when the enzyme is capable of converting the prodrug to a drug at the target site;

2) a drug which is capable of being detoxified in the patient to form an intermediate of lower toxicity, when the enzyme is capable of reconverting the detoxified intermediate to a toxic form, and, therefore, of increasing the toxicity of the drug at the target site, 3) a prodrug which is activated in the patient through natural processes and is subject to detoxification by conversion to an intermediate of lower toxicity, when the enzyme is capable of reconverting the detoxified intermediate to a toxic form, and, therefore, of increasing the toxicity of the drug at the target site, or 4) a second targetable construct which comprises a carrier portion which comprises or bears at least one epitope recognizable by the at least one other arm of the bi-specific antibody or antibody fragment, and a prodrug, when the enzyme is capable of converting the prodrug to a drug at the target site.

Another embodiment of the invention provides a method of preparing the antibodies or antibody fragments by recombinant technology. In accordance with this aspect of the present invention, there is provided a method of preparing a bi-specific antibody or antibody fragment having at least one arm that specifically binds a targeted tissue and at least one other arm that specifically binds a targetable construct, comprising:

(A) introducing the recombinant DNA construct described above into a host cell;

(B) growing the cell and isolating the antibody or antibody fragment.

In another embodiment of the present invention there is provided a method of preparing a bi-specific fusion protein having at least one arm that specifically binds to a targeted tissue and at least one other arm that is specifically binds to a targetable construct, comprising:

(1) (A) introducing into a host cell a recombinant DNA construct comprising an expression cassette capable of producing in the host cell a fragment of the bi-specific fusion protein, wherein the construct comprises, in the 5' to 3' direction of transcription, a transcriptional initiation regulatory region functional in the host cell, a translational initiation regulatory region functional in the host cell, a DNA sequence encoding a scFv linked to a light-chain antibody fragment, and a transcriptional and translational termination regulatory region functional in the host cell, wherein the fragment of the bi-specific fusion protein is under the control of the regulatory regions;

(B) co-introducing into the host cell a recombinant DNA construct comprising an expression cassette capable of producing in the host cell a Fd fragment which is complementary to the light-chain antibody fragment in (A) and which when associated with the light-chain antibody fragment forms a Fab fragment whose binding site is specific for the targeted tissue, wherein the construct comprises, in the 5' to 3' direction of transcription, a transcriptional initiation regulatory region functional in the host cell, a translational initiation regulatory region functional in the host cell, a DNA sequence encoding a Fd fragment, and a transcriptional and translational termination regulatory region functional in the host cell, wherein the Fd fragment is under the control of the regulatory regions;

(C) growing the cell and isolating the bi-specific fusion protein, or (2) (A) introducing into a first host cell a recombinant DNA construct comprising an expression cassette capable of producing in the first host cell a fragment of the bi-specific fusion protein, wherein the construct comprises, in the 5' to 3' direction of transcription, a transcriptional initiation regulatory region functional in the first host cell, a translational initiation regulatory region functional in the first host cell, a DNA sequence encoding a scFv linked to a light-chain antibody fragment, and a transcriptional and translational termination regulatory region functional in the first host cell, wherein the fragment of the bi-specific fusion protein is under the control of the regulatory regions;

(B) introducing into a second host cell a recombinant DNA construct comprising an expression cassette capable of producing in the second host cell a Fd fragment which is complementary to the light-chain antibody fragment in (2)(A) and which when associated with the light-chain antibody fragment forms a Fab fragment whose binding site is specific for the targeted tissue, wherein the construct comprises, in the 5' to 3' direction of transcription, a transcriptional initiation regulatory region functional in the second host cell, a translational initiation regulatory region functional in the second host cell, a DNA sequence encoding a Fd fragment, and a transcriptional and translational termination regulatory region functional in the second host cell, wherein the Fd fragment is under the control of the regulatory regions;

(C) growing the first and second host cells;

(D) optionally isolating the bi-specific fusion protein fragment and the Fd fragment; and (E) combining the fragments to produce a bi-specific fusion protein and isolating the bi-specific fusion protein.

A variety of host cells can be used to prepare bi-specific antibodies or antibody fragments, including, but not limited to, mammalian cells, insect cells, plant cells and bacterial cells. In one embodiment, the method utilizes a mammalian zygote, and the introduction of the recombinant DNA construct produces a transgenic animal capable of producing a bi-specific antibody or antibody fragment.

The present inventors have discovered that it is advantageous to raise bsAbs against a targetable construct that is capable of carrying one or more diagnostic or therapeutic agents. By utilizing this technique, the characteristics of the chelator, metal chelate complex, therapeutic agent or diagnostic agent can be varied to accommodate differing applications, without raising new bsAbs for each new application.

Further, by using this approach, two or more distinct chelators, metal chelate complexes or therapeutic agents can be used with the inventive bsAb.

The invention further relates to a method of screening for a targetable construct comprising:

contacting said targetable construct with a bi-specific antibody or antibody fragment having at least one arm that specifically binds a targeted tissue and at least one other arm that specifically binds said targetable construct to give a mixture;

wherein said at least one arm is capable of binding to a complementary binding moiety on the target cells, tissues or pathogen or on a molecule produced by or associated therewith; and optionally incubating said mixture; and analyzing said mixture.

Additional aspects, features and advantages of the invention will be set forth in the description which follows, and in part will be obvious from the description, or may be learned by practice of the invention. The embodiments and advantages of the invention may be realized and obtained by means of the instrumentalities and combinations particularly pointed out in the present specification. One skilled in the art will recognize that the embodiments described herein can be suitably used in combination with any other suitable described embodiment.

DETAILED DESCRIPTION

Figure 1:
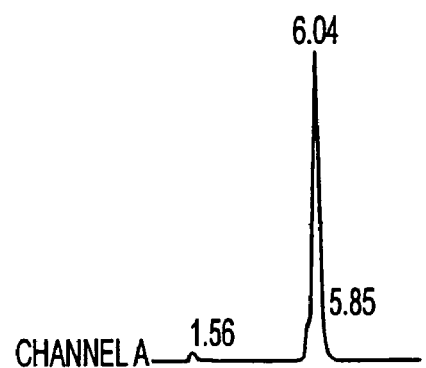
FIG. 1 shows a reversed phase HPLC (RP-HPLC)trace of labeled IMP 281.

Unless otherwise specified, "a" or "an" means "one or more".

The present invention provides compounds comprising the formula:

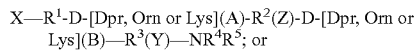
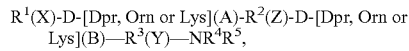

wherein:

X is a hard acid cation chelator, a soft acid cation chelator, an enzyme, a therapeutic agent, a diagnostic agent, or Ac—;

$R^1$ is a covalent bond or one or more D-amino acids that can be the same or different;

$R^2$ is a covalent bond or one or more D-amino acids that can be the same or different;

$R^3$ is a covalent bond or one or more D-amino acids that can be the same or different;

Y is a hard acid cation chelator, a soft acid cation chelator, an enzyme, a therapeutic agent, a diagnostic agent or absent;

Z is a hard acid cation chelator, a soft acid cation chelator, an enzyme, a therapeutic agent, a diagnostic agent, or absent;

A and B are haptens or hard acid cation chelators and can be the same or different; and $R^4$ and $R^5$ are independently selected from the group consisting of hard acid cation chelators, soft acid cation chelators, enzymes, therapeutic agents, diagnostic agents and H. In the present formula Dpr is 2,3-diaminoproprionic acid. In some of these embodiments, when $R^1$ or $R^3$ is a covalent bond then the other $R^1$ or $R^3$ can be one or more D-amino acids that can be the same or different. In these and other embodiments, $R^2$ can be one or more D-amino acids that can be the same or different. In still other of these embodiments, the compound can comprise the formula X—$R^1$-D-Lys(A)-$R^2$-D-Lys(B)—$R^3$(Y)—NR$^4$R$^5$. In some of these embodiments $R^2$ is a single D-amino acid. In other embodiments, $R^2$ is two D-amino acids that can be the same or different. In further embodiments, $R^3$ is a D-Lys and Y is a hard acid cation chelator or a soft acid cation chelator. In some of these embodiments $R^2$ is not a D-Lys. In still further embodiments A and B are independently selected from the group consisting of histamine-succinyl-glycine (HSG), DTPA and fluorescein isothiocyanate. In yet other embodiments, $R^1$ is one or more D-amino acids that can be the same or different, $R^2$ is one or more D-amino acids that can be the same or different, $R_3$ is a covalent bond, Y is absent, and A and B are haptens or hard acid cation chelators and can be the same or different. In additional embodiments A and B are haptens and can be the same or different. In these and other embodiments $R^1$ and $R^2$ are single D-amino acids and can be the same or different.

When $R^1$ is more than one amino acid then one, any or all of the amino acids can be attached to the (X) group. Similarly, when $R^2$ is more than one amino acid then one, any or all of the amino acids can be attached to the (Z) group. In some embodiments, Z is absent. In some embodiments, only one or two of X, Y, Z $R^4$ or $R^5$ is an enzyme, a therapeutic agent or a diagnostic agent. Parentheses indicate substituents on the amino acid side chain. If the molecules are in the main chain of the peptide then they are not surrounded by parentheses. In the context of the present invention the skilled artisan will recognize that one or more amino acids may refer to 1-10 amino acids, advantageously 1-5 amino acids, although more than 10 amino acids may be employed as required.

In additional embodiments $R^1$ is selected from the group consisting of D-Tyr, D-Ala, D-Ser, D-Thr, D-Cys, D-Leu, D-Ile, D-Met, D-Gln, D-Asn, D-Val, and D-Phe. In additional embodiments $R^1$ is selected from the group consisting of D-Pro, D-His, D-Trp, D-Glu, D-Asp, D-Arg, and D-Lys. In these and other embodiments, $R^2$ is selected from the group consisting of D-Asp, D-Glu and D-Tyr. In some of the embodiments described herein $R^4$ and $R^5$ are both H. In other embodiments, one of X, $R^4$ and $R^5$ is a hard acid cation chelator. In these and other embodiments, one of the remaining X, $R^4$ and $R^5$ is a soft acid cation chelator. In some embodiments, X is a hard acid cation chelator. In additional embodiments, one of $R^4$ and $R^5$ is a hard acid cation chelator. In some embodiments, the hard acid cation chelator comprises a carboxylate or amine group. In yet further embodiments the hard acid cation chelator is selected from the group consisting of NOTA, DOTA, DTPA, and TETA. In still other embodiments, one of X, $R^4$ and $R^5$ is a soft acid cation chelator, which can comprise a thiol group. The soft acid cation chelator can be selected from the group consisting of Tscg-Cys and Tsca-Cys. In some of the present compounds one of $R^4$ and $R^5$ is a soft acid cation chelator and the remaining $R^4$ or $R^5$ is H.

In certain embodiments, X is Ac—, A and B are hard acid cation chelators and can be the same or different, $R^3$ is a covalent bond, and Y is absent. In some embodiments, X is Ac—, A and B are haptens and can the same or different, $R^1$ is a covalent bond, and Y is a soft acid cation chelator. Specific embodiments of the present compounds include:

(IMP 271);

(IMP 277);

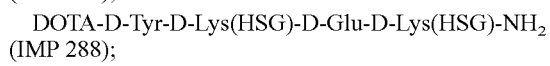
(IMP 288);

(IMP 0281);

(IMP 284)

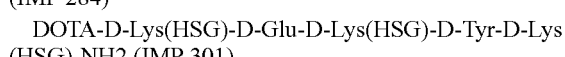
(HSG)-NH2 (IMP 301)

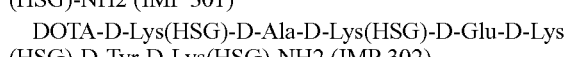
(HSG)-D-Tyr-D-Lys(HSG)-NH2 (IMP 302)

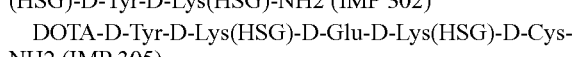
NH2 (IMP 305)

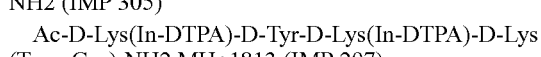
(Tscg-Cys)-NH2 MH+1813 (IMP 297)

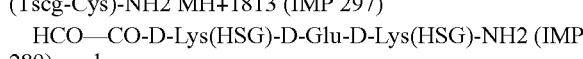
289); and

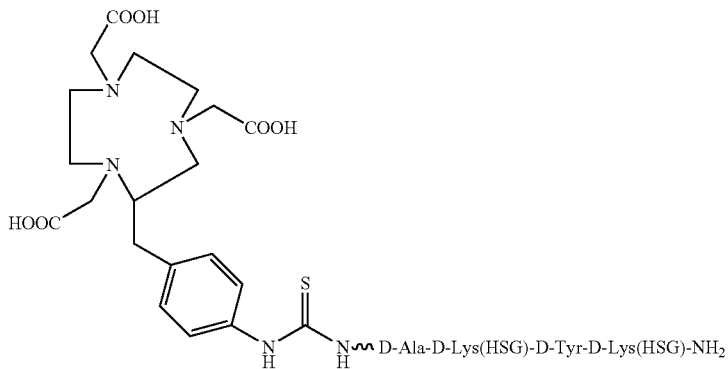

In some embodiments of the present compounds, (i) no more than one of X, $R^4$ and $R^5$ is a hard acid cation chelator and (ii) no more than one of X, $R^4$ and $R^5$ is a soft acid cation chelator. Additional specific examples of the present compounds include:

Ac-D-Phe-D-Lys(DOTA)-D-Tyr-D-Lys(DOTA)-$NH_2$;
Ac-D-Phe-D-Lys(DTPA)-D-Tyr-D-Lys(DTPA)-$NH_2$;
Ac-D-Phe-D-Lys(Bz-DTPA)-D-Tyr-D-Lys(Bz-DTPA)-$NH_2$
Ac-D-Lys(HSG)-D-Tyr-D-Lys(HSG)-D-Lys(Tscg-Cys)-$NH_2$;
DOTA-D-Phe-D-Lys(HSG)-D-Tyr-D-Lys(HSG)-D-Lys(Tscg-Cys)-$NH_2$;
(Tscg-Cys)-D-Phe-D-Lys(HSG)-D-Tyr-D-Lys(HSG)-D-Lys(DOTA)-$NH_2$;
Tscg-D-Cys-D-Glu-D-Lys(HSG)-D-Glu-D-Lys(HSG)-$NH_2$;
(Tscg-Cys)-D-Glu-D-Lys(HSG)-D-Glu-D-Lys(HSG)-$NH_2$;
Ac-D-Cys-D-Lys(DOTA)-D-Tyr-D-Ala-D-Lys(DOTA)-D-Cys-$NH_2$;
Ac-D-Cys-D-Lys(DTPA)-D-Tyr-D-Lys(DTPA)-$NH_2$;
Ac-D-Lys(DTPA)-D-Tyr-D-Lys(DTPA)-D-Lys(TscG-Cys)-$NH_2$; and
Ac-D-Lys(DOTA)-D-Tyr-D-Lys(DOTA)-D-Lys(TscG-Cys)-$NH_2$.

In these and other embodiments the compounds can further comprise at least one radionuclide. In some of the present compounds the hard acid cation chelator is chelated to a cation selected from the group consisting of Group IIa and Group IIIa metal cations. In these and other embodiments the soft acid cation chelator is chelated to a cation selected from the group consisting of transition metals, Bi, lanthanides and actinides.

In still other embodiments the present compounds $R^4$ or $R^5$ is a therapeutic agent, diagnostic agent or enzyme.

In some of the present compounds the amino acid backbone can have a length of 2 to about 50, 75, 85 or 100 contiguous amino acids. For example $R^1$ or $R^3$ can be from about 1, 2, 5, 10 or 15 amino acids t about 20, 25, 30 or 35 amino acids in length. In certain compounds the amino acid chain will be 3, 4, 5, 6, 7, 8, 9 or 10 amino acids in length. In certain embodiments, $R^2$ is 1, 2, or 3 amino acids in length. In some embodiments, the present invention also provides a targetable construct comprising any of the present compounds. In some of the present compounds, the amino acid backbone is cyclic, while in others it is linear. The present compounds are useful, inter alia, as targetable constructs.

Desirably, the targetable construct includes a peptide having at least 2 units of a recognizable hapten. Examples of recognizable haptens include, but are not limited to, histamine succinyl glycine (HSG) and fluorescein isothiocyanate. The targetable construct may be conjugated to a variety of agents useful for treating or identifying diseased tissue. Examples of conjugated agents include, but are not limited to, chelators, metal chelate complexes, drugs, toxins (e.g., ricin, abrin, ribonuclease (e.g., RNase), DNase I, *Staphylococcal* enterotoxin-A, pokeweed antiviral protein, gelonin, diphtherin toxin, *Pseudomonas* exotoxin, *Pseudomonas* endotoxin) and other effector molecules. Additionally, enzymes useful for activating a prodrug or increasing the target-specific toxicity of a drug can be conjugated to the targetable construct. Thus, the use of bsAb which are reactive to a targetable construct allows a variety of therapeutic and diagnostic applications to be performed without raising new bsAb for each application.

Bispecific antibody (bsAb) pretargeting represents a potentially non-immunogenic, highly selective alternative for diagnostic and therapeutic applications. The bsAb pretargeting system described herein represents an additional significant advantage over other pretargeting systems in that it potentially can be developed for use with a variety of different imaging or therapeutic agents. The flexibility of this system is based on use of an antibody directed against histamine-succinyl-glycl (HSG) and the development of peptides containing the HSG residue. HSG-containing peptides were synthesized with either DOTA for the chelation of $^{111}$In, $^{90}$Y, or $^{177}$Lu or a technetium/rhenium chelate. For pretargeting, these peptides were used in combination with bispecific antibodies using the anti-HSG Fab' chemically stabilized with the Fab' of either an anti-carcinoembryonic antigen (CEA) or an anti-colon-specific antigen-p (CSAp) antibody to provide tumor targeting capability for tumors expressing these antigens. However, other antigen targets may include diverse tumor-associated antigens known in the art, such as against CD19, CD20, CD21, CD22, CD23, CD25, CD30, CD74, CD 80, HLA-DR, Ia, MUC 1, MUC 2, MUC 3, MUC 4, EGFR, HER 2/neu, PAM-4, BrE3, TAG-72 (B72.3, CC49), EGP-1 (e.g., RS7), EGP-2 (e.g., 17-1A and other Ep-CAM targets), Le(y) (e.g., B3), A3, KS-1, S100, IL-2, T101, necrosis antigens, folate receptors, angiogenesis markers (e.g., VEGF), tenascin, PSMA, PSA, tumor-associated cytokines, MAGE and/or fragments thereof. Tissue-specific antibodies (e.g., against bone marrow cells, such as CD34, CD74, etc., parathyroglobulin antibodies, etc.) as well as antibodies against non-malignant diseased tissues, such as fibrin of clots, macrophage antigens of atherosclerotic plaques (e.g., CD74 antibodies), and also specific pathogen antibodies (e.g., against bacteria, viruses, and parasites) are well known in the art.

The peptides can be radiolabeled to a high specific activity in a facile manner that avoids the need for purification. In some embodiments the peptides will be cleared rapidly from the body with minimal retention in tumor or normal tissues. The pretargeting system described herein is highly flexible, being capable of using a wide array of compounds of diagnostic imaging and therapeutic interest, and by achieving excellent tumor uptake and targeting ratios, is highly promising for use in these applications.

Additionally, encompassed is a method for detecting and/or treating target cells, tissues or pathogens in a mammal, comprising administering an effective amount of one or more of the present compounds as a targetable construct. The method can further comprise administering a bispecific antibody or antibody fragment comprising at least one arm that specifically binds a targeted cell, tissue or pathogen and at least one other arm that specifically binds a targetable construct. As used herein, the term "pathogen" includes, but is not limited to fungi (e.g., *Microsporum, Trichophyton, Epidermophyton, Sporothrix schenckii, Cryptococcus neoformans, Coccidioides immitis, Histoplasma Capsulatum, Blastomyces dermatitidis, Candida albicans*), viruses (e.g., human immunodeficiency virus (HIV), herpes virus, cytomegalovirus, rabies virus, influenza virus, hepatitis B virus, Sendai virus, feline leukemia virus, Reo virus, polio virus, human serum parvo-like virus, simian virus 40, respiratory syncytial virus, mouse mammary tumor virus, *Varicella-Zoster* virus, Dengue virus, rubella virus, measles virus, adenovirus, human T-cell leukemia viruses, Epstein-Barr virus, murine leukemia virus, mumps virus, vesicular stomatitis virus, Sindbis virus, lymphocytic choriomeningitis virus, wart virus and blue tongue virus), parasites, bacteria (e.g., *Anthrax bacillus, Streptococcus agalactiae, Legionella pneumophilia, Streptococcus pyogenes, Escherichia coli, Neisseria gonorrhoeae, Neisseria meningitidis*, Pneumococcus, Hemophilis influenzae B, *Treponema pallidum*, Lyme disease spirochetes, *Pseudomonas aeruginosa, Mycobacterium leprae, Brucella abortus, Mycobacterium tuberculosis* and Tetanus toxin), mycoplasma (e.g., *Mycoplasma arthritidis, M. hyorhinis, M. orale, M. arginini, Acholeplasma laidlawii, M. salivarum*, and *M. pneumoniae*) and protozoans (e.g., *Plasmodium falciparum, Plasmodium vivax, Toxoplasma gondii, Trypanosoma rangeli, Trypanosoma cruzi, Trypanosoma rhodesiensei, Trypanosoma brucei, Schistosoma mansoni, Schistosoma japanicum, Babesia bovis, Elmeria tenella, Onchocerca volvulus, Leishmania tropica, Trichinella spiralis, Onchocerca volvulus, Theileria parva, Taenia hydatigena, Taenia ovis, Taenia saginata, Echinococcus granulosus* and *Mesocestoides corti*). See U.S. Pat. No. 5,332,567.

Also provided herein are antibodies and antibody fragments. The antibody fragments are antigen binding portions of an antibody, such as F(ab')$_2$, F(ab)$_2$, Fab', Fab, and the like. The antibody fragments bind to the same antigen that is recognized by the intact antibody. For example, an anti-CD22 monoclonal antibody fragment binds to an epitope of CD22.

The term "antibody fragment" also includes any synthetic or genetically engineered protein that acts like an antibody by binding to a specific antigen to form a complex. For example, antibody fragments include isolated fragments, "Fv" fragments, consisting of the variable regions of the heavy and light chains, recombinant single chain polypeptide molecules in which light and heavy chain variable regions are connected by a peptide linker ("sFv proteins"), and minimal recognition units consisting of the amino acid residues that mimic the "hypervariable region." Three of these so-called "hypervariable" regions or "complementarity-determining regions" (CDR) are found in each variable region of the light or heavy chain. Each CDR is flanked by relatively conserved framework regions (FR). The FR are thought to maintain the structural integrity of the variable region. The CDRs of a light chain and the CDRs of a corresponding heavy chain form the antigen-binding site. The "hypervariability" of the CDRs accounts for the diversity of specificity of antibodies.

As used herein, the term "subject" refers to any animal (i.e., vertebrates and invertebrates) including, but not limited to humans and other primates, rodents (e.g., mice, rats, and guinea pigs), lagamorphs (e.g., rabbits), bovines (e.g, cattle), ovines (e.g., sheep), caprines (e.g., goats), porcines (e.g., swine), equines (e.g., horses), canines (e.g., dogs), felines (e.g., cats), domestic fowl (e.g., chickens, turkeys, ducks, geese, other gallinaceous birds, etc.), as well as feral or wild animals, including, but not limited to, such animals as ungulates (e.g., deer), bear, fish, lagamorphs, rodents, birds, etc. It is not intended that the term be limited to a particular age or sex. Thus, adult and newborn subjects, as well as fetuses, whether male or female, are encompassed by the term.

Suitable antibodies and fragments for use with the present compounds include the following: Fvs derived from anti-CD20 antibodies, such as those described in Provisional U.S. Application titled "Anti-CD20 Antibodies And Fusion Proteins Thereof And Methods Of Use", U.S. Provisional No. 60/356,132, U.S. Provisional Application No. 60/416,232 and Ser. No. 10/366,709 (the contents of which are in their entirety herein by reference); hMN-14 antibodies, such as those disclosed in U.S. application No. 5,874,540 (the contents of which are incorporated in their entirety herein by reference), which is a Class III anti-carcinoembryonic antigen antibody (anti-CEA antibody); Mu-9 antibodies, such as those described in U.S. application Ser. No. 10/116,116 (the contents of which are incorporated in their entirety herein by reference); LL1 antibodies, such as those described in U.S. Provisional Application No. 60/360,259 (the contents of which are incorporated in their entirety herein by reference); AFP antibodies, such as those described in U.S. Provisional Application No. 60/399,707 (the contents of which are incorporated in their entirety herein by reference); PAM4 antibodies, such as those described in Provisional U.S. Application titled "Monoclonal Antibody cPAM4", Ser. No. 30/388,313 (the contents of which are incorporated in their entirety herein by reference); RS7 antibodies, such as those described in U.S. Provisional Application No. 60/360,229 (the contents of which are incorporated in their entirety herein by reference); humanized MN3 antibodies, such as those disclosed in U.S. Provisional Application No. 60/414,341, and CD22 antibodies, such as those disclosed in U.S. Pat. Nos. 5,789,554 and 6,187,287 and U.S. application Ser. Nos. 09/741,843 and 09/988,013 (the contents of which are incorporated in their entirety herein by reference). Many other tumor-associated antigens of hematopoietic and solid tumors are known to those skilled in the art, as contained in the referenced applications, and include (but are not limited to) CD15, CD19, CD20, CD21, CD22, CD23, CD25, CD40, CD45, CD66, CD74, CD80, Ii, Ia, HLA-DR, PSMA, PSA, prostatic acid phosphatase, tenascin, Le(y), AFP, HCG, CEA, CSAp, PAM4, MUC 1, MUC2, MUC3, MUC4, EGP-1, EGP-2, EGFR, HER2/neu, insulin growth-factor receptors, S100, VEGF, Placenta Growth Factor (PIGF), placental alkaline phosphatase, necrosis products, oncogene products, and the like. The present compounds can also be used in conjunction with any of the methods disclosed in the above applications.

II. Constructs Targetable to Antibodies

The targetable construct can be of diverse structure as described herein. In preferred embodiments, the compounds are selected to diminish the elicitation of immune responses and/or for rapid in vivo clearance when used within the bsAb targeting method. Hydrophobic agents are best at eliciting strong immune responses, whereas hydrophilic agents are preferred for rapid in vivo clearance, thus, a balance between hydrophobic and hydrophilic needs to be established. This is accomplished, in part, by relying on the use of hydrophilic chelating agents to offset the inherent hydrophobicity of many organic moieties. Also, sub-units of the targetable construct may be chosen which have opposite solution properties, for example, peptides, which contain amino acids, some of which are hydrophobic and some of which are hydrophilic. Aside from peptides, carbohydrates may be used.

Any amino acid can be used in the present compounds, including naturally and non-naturally occurring amino acids.

The targetable construct may include a peptide backbone having as few as two amino-acid residues, with preferably two to ten amino acid residues, and may be coupled to other moieties such as chelating agents. The targetable construct should be a low molecular weight construct, preferably having a molecular weight of less than 50,000 daltons, and advantageously less than about 20,000 daltons, 10,000 daltons or 5,000 daltons, including any metal ions that may be bound to the chelating agents. For instance, the known peptide DTPA-Tyr-Lys(DTPA)-OH (wherein DTPA is diethylenetriaminepentaacetic acid) has been used to generate antibodies against the indium-DTPA portion of the molecule. However, by use of the non-indium-containing molecule, and appropriate screening steps, new Abs against the tyrosyl-lysine dipeptide can be made. More usually, the antigenic peptide of the targetable construct will have four or more residues, such as the peptide DOTA-D-Phe-D-Lys(HSG)-D-Tyr-D-Lys(HSG)-NH$_2$, wherein DOTA is 1,4,7,10-tetraaza-cyclododecanetetraacetic acid and HSG is the histamine succinyl glycyl group of the formula:

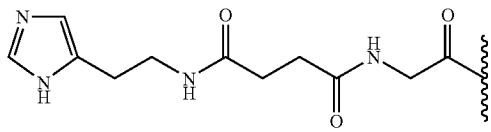

The non-metal-containing peptide may be used as an immunogen, with resultant Abs screened for reactivity against the D-Phe-D-Lys-D-Tyr-D-Lys backbone.

The haptens of the targetable construct also provide an immunogenic recognition moiety, for example, a chemical hapten. Using a chemical hapten, preferably the HSG hapten, high specificity of the construct for the antibody is exhibited. This occurs because antibodies raised to the HSG hapten are known and can be easily incorporated into the appropriate bsAb. Thus, binding of the haptens to the peptide backbone would result in a targtable construct that is specific for the bsAb or bsFab.

The present inventors have discovered that peptides having all D-amino acid backbones are stable in vitro and in vivo, even compared against peptides having one or a few D-amino acids incorporated into the backbone. Incorporation of unnatural amino acids, e.g., D-amino acids, into the peptide backbone structure also helps to ensure that, when used with the final bsAb/construct system, the arm of the bsAb which recognizes the targetable construct is specific. The invention further contemplates other backbone structures such as those constructed from non-natural amino acids and peptoids.

The peptides to be used as described can be synthesized conveniently on an automated peptide synthesizer using a solid-phase support and standard techniques of repetitive orthogonal deprotection and coupling. Free amino groups in the peptide, that are to be used later for chelate conjugation, are advantageously blocked with standard protecting groups such as an acetyl group. Such protecting groups will be known to the skilled artisan. See Greene and Wuts *Protective Groups in Organic Synthesis,* 1999 (John Wiley and Sons, N.Y.). When the peptides are prepared for later use within the bsAb system, they are advantageously cleaved from the resins to generate the corresponding C-terminal amides, in order to inhibit in vivo carboxypeptidase activity.

III. Chelate Moieties

The presence of hydrophilic chelate moieties on the targetable construct helps to ensure rapid in vivo clearance. In addition to hydrophilicity, chelators are chosen for their metal-binding properties, and may be changed at will since, at least for those targetable constructs whose bsAb epitope is part of the peptide or is a non-chelate chemical hapten, recognition of the metal-chelate complex is no longer an issue.

Particularly useful metal-chelate combinations include 2-benzyl-DTPA and its monomethyl and cyclohexyl analogs, used with $^{47}$Sc, $^{52}$Fe, $^{55}$Co, $^{67}$Ga, $^{68}$Ga, $^{111}$In, $^{89}$Zr, $^{90}$Y, $^{16}$Tb, $^{177}$Lu, $^{212}$Bi, $^{213}$Bi, and $^{225}$Ac for radio-imaging and RAIT. The same chelators, when complexed with non-radioactive metals such as Mn, Fe and Gd for use with MRI, when used along with the bsAbs of the invention. Macrocyclic chelators such as NOTA (1,4,7-triaza-cyclononane-N,N',N''-triacetic acid), DOTA, and TETA (p-bromoacetamido-benzyl-tetraethylaminetetraacetic acid) are of use with a variety of metals and radiometals, most particularly with radionuclides of Ga, Y and Cu, respectively.

DTPA and DOTA-type chelators, where the ligand includes hard base chelating functions such as carboxylate or amine groups, are most effective for chelating hard acid cations, especially Group IIa and Group IIIa metal cations. Such metal-chelate complexes can be made very stable by tailoring the ring size to the metal of interest. Other ring-type chelators such as macrocyclic polyethers are of interest for stably binding nuclides such as $^{223}$Ra for RAIT. Porphyrin chelators may be used with numerous radiometals, and are also useful as certain cold metal complexes for bsAb-directed immuno-phototherapy. Also, more than one type of chelator may be conjugated to the targetable construct to bind multiple metal ions, e.g., cold ions, diagnostic radionuclides and/or therapeutic radionuclides.

Particularly useful diagnostic radionuclides that can be bound to the chelating agents of the targetable construct include, but are not limited to, $^{110}$In, $^{111}$In, $^{177}$Lu, $^{18}$F, $^{52}$F, $^{62}$Cu, $^{64}$Cu, $^{67}$Cu, $^{67}$Ga, $^{68}$Ga, $^{86}$Y, $^{90}$Y, $^{89}$Zr, $^{94m}$TC, $^{94}$Tc, $^{99m}$Tc, $^{120}$I, $^{123}$I, $^{124}$I, $^{125}$I, $^{131}$I, $^{154-158}$Gd, $^{32}$P, $^{11}$C, $^{13}$N, $^{15}$O, $^{186}$Re, $^{188}$Re, $^{51}$Mn, $^{52m}$Mn, $^{55}$Co, $^{72}$As, $^{75}$Br, $^{76}$Br, $^{82m}$Rb, $^{83}$Sr, or other gamma-, beta-, or positron-emitters. Preferably, the diagnositc radionuclides include a decay energy in the range of 25 to 10,000 keV, more preferably in the range of 25 to 4,000 keV, and even more preferably in the range of 20 to 1,000 keV, and still more preferably in the range of 70 to 700 keV. Total decay energies of useful positron-emitting radionuclides are preferably <2,000 keV, more preferably under 1,000 keV, and most preferably <700 keV. Radionuclides useful as diagnostic agents utilizing gamma-ray detection include, but are not limited to: Cr-51, Co-57, Co-58, Fe-59, Cu-67, Ga-67, Se-75, Ru-97, Tc-99m, In-111, In-114m, I-123, I-125, I-131, Yb-169, Hg-197, and Tl-201. Decay energies of useful gamma-ray emitting radionuclides are preferably 20-2000 keV, more preferably 60-600 keV, and most preferably 100-300 keV.

Particularly useful therapeutic radionuclides that can be bound to the chelating agents of the targetable construct include, but are not limited to $^{111}$In, $^{177}$Lu, $^{212}$Bi, $^{213}$Bi, $^{211}$At, $^{62}$Cu, $^{64}$Cu, $^{67}$Cu, $^{90}$Y, $^{125}$I, $^{131}$I, $^{32}$P, $^{33}$P, $^{47}$sc, $^{111}$Ag, $^{67}$Ga, $^{142}$Pr, $^{153}$Sm, $^{161}$Tb, $^{166}$Dy, $^{166}$Ho, $^{186}$Re, $^{188}$Re, $^{189}$Re, $^{212}$Pb, $^{223}$Ra, $^{225}$Ac, $^{59}$Fe, $^{75}$Se, $^{77}$As, $^{89}$Sr, $^{99}$Mo, $^{105}$Rh, $^{109}$Pd, $^{143}$Pr, $^{149}$Pm, $^{169}$Er, $^{194}$Ir, $^{198}$Au, $^{199}$Au, and $^{211}$Pb. The therapeutic radionuclide preferably has a decay energy in the range of 25 to 10,000 keV. Decay energies of useful beta-particle-emitting nuclides are preferably 25-5,000 keV, more preferably 100-4,000 keV, and most preferably 500-2,500 keV. Also preferred are radionuclides that substantially decay with Auger-emitting particles. For example, Co-58, Ga-67, Br-80m, Tc-99m, Rh-103m, Pt-109, In-111, Sb-119, I-125, Ho-161, Os-189m and Ir-192. Decay energies of useful beta-particle-emitting nuclides are preferably <1,000 keV, more preferably <100 keV, and most preferably <70 keV. Also preferred are radionuclides that substantially decay with generation of alpha-particles. Such radionuclides include, but are not limited to: Dy-152, At-211, Bi-212, Ra-223, Rn-219, Po-215, Bi-211, Ac-225, Fr-221, At-217, Bi-213 and Fm-255. Decay energies of useful alpha-particle-emitting radionuclides are preferably 2,000-9,000 keV, more preferably 3,000-8,000 keV, and most preferably 4,000-7,000 keV.

Chelators such as those disclosed in U.S. Pat. No. 5,753,206, especially thiosemi-carbazonylglyoxylcysteine(Tscg-Cys) and thiosemicarbazinyl-acetylcysteine (Tsca-Cys) chelators are advantageously used to bind soft acid cations of Tc, Re, Bi and other transition metals, lanthanides and actinides that are tightly bound to soft base ligands, especially sulfur- or phosphorus-containing ligands. It can be useful to link more than one type of chelator to a peptide, e.g., a hard acid chelator like DTPA for In(III) cations, and a soft acid chelator (e.g, thiol-containing chelator such as Tscg-Cys) for Tc cations. Because antibodies to a di-DTPA hapten are known (Barbet '395, supra) and are readily coupled to a targeting antibody to form a bsAb, it is possible to use a peptide hapten with cold di-DTPA chelator and another chelator for binding a radioisotope, in a pretargeting protocol, for targeting the radioisotope. One example of such a peptide is Ac-D-Lys(DTPA)-D-Tyr-D-Lys(DTPA)-D-Lys(Tscg-Cys)-NH$_2$. This peptide can be preloaded with In(III) and then labeled with 99-m-Tc cations, the In(III) ions being preferentially chelated by the DTPA and the Tc cations binding preferentially to the thiol-containing Tscg-Cys. Other hard acid chelators such as NOTA, DOTA, TETA and the like can be substituted for the DTPA groups, and Mabs specific to them can be produced using analogous techniques to those used to generate the anti-di-DTPA Mab.

It will be appreciated that two different hard acid or soft acid chelators can be incorporated into the linker, e.g., with different chelate ring sizes, to bind preferentially to two different hard acid or soft acid cations, due to the differing sizes of the cations, the geometries of the chelate rings and the preferred complex ion structures of the cations. This will permit two different metals, one or both of which may be radioactive or useful for MRI enhancement, to be incorporated into a linker for eventual capture by a pretargeted bsAb.

Preferred chelators include NOTA, DOTA and Tscg and combinations thereof. These chelators have been incorporated into a chelator-peptide conjugate motif as exemplified in the following constructs:

DOTA-D-Asp-D-Lys(HSG)-D-Asp-D-Lys(HSG)-NH$_2$ (IMP 271);

DOTA-D-Glu-D-Lys(HSG)-D-Glu-D-Lys(HSG)-NH$_2$ (IMP 277);

DOTA-D-Tyr-D-Lys(HSG)-D-Glu-D-Lys(HSG)-NH$_2$ (IMP 288);

DOTA-D-Ala-D-Lys(HSG)-D-Glu-D-Lys(HSG)-NH2 (IMP 0281);

DOTA-D-Phe-D-Lys(HSG)-D-Tyr-D-Lys(HSG)-NH$_2$ (IMP 284)

DOTA-D-Lys(HSG)-D-Glu-D-Lys(HSG)-D-Tyr-D-Lys (HSG)-NH2 (IMP 301)

DOTA-D-Lys(HSG)-D-Ala-D-Lys(HSG)-D-Glu-D-Lys (HSG)-D-Tyr-D-Lys(HSG)-NH2 (IMP 302)

DOTA-D-Tyr-D-Lys(HSG)-D-Glu-D-Lys(HSG)-D-Cys-NH2 (IMP 305)

Ac-D-Lys(In-DTPA)-D-Tyr-D-Lys(In-DTPA)-D-Lys (Tscg-Cys)-NH2 MH+1813 (IMP 297)

HCO—CO-D-Lys(HSG)-D-Glu-D-Lys(HSG)-NH2 (IMP 289); and

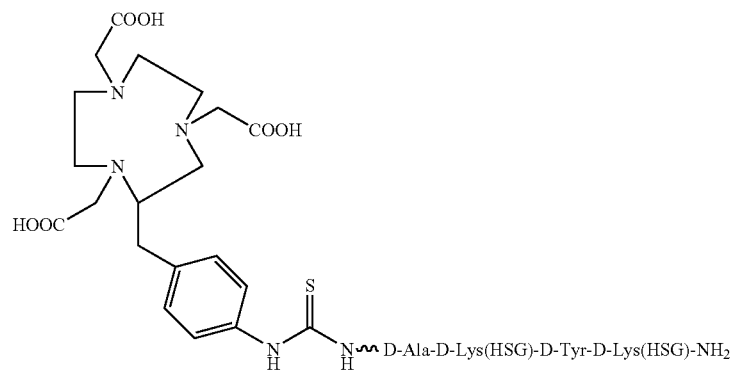

The chelator-peptide conjugates above, are capable of binding $^{68}$Ga and are thus useful in positron emission tomography (PET) applications.

Chelators are coupled to the peptides of the targetable construct using standard chemistries, some of which are discussed more fully in the working examples below.

IV. General Methods for Preparation of Metal Chelates

Chelator-peptide conjugates may be stored for long periods as solids. They may be metered into unit doses for metal-binding reactions, and stored as unit doses either as solids, aqueous or semi-aqueous solutions, frozen solutions or lyophilized preparations. They may be labeled by well-known procedures.

Typically, a hard acid cation is introduced as a solution of a convenient salt, and is taken up by the hard acid chelator and possibly by the soft acid chelator. However, later addition of soft acid cations leads to binding thereof by the soft acid chelator, displacing any hard acid cations which may be chelated therein. For example, even in the presence of an excess of cold $^{111}$InCl$_3$, labeling with 99m-Tc(V) glucoheptonate or with Tc cations generated in situ with stannous chloride and Na99m-TcO$_4$ proceeds quantitatively on the soft acid chelator.

Other soft acid cations such as $^{186}$Re, $^{188}$Re, $^{213}$Bi and divalent or trivalent cations of Mn, Co, Ni, Pb, Cu, Cd, Au, Fe, Ag (monovalent), Zn and Hg, especially $^{64}$Cu and $^{67}$Cu, and the like, some of which are useful for radioimmunodetection or radioimmunotherapy, can be loaded onto the linker peptide by analogous methods. Re cations also can be generated in situ from perrhenate and stannous ions or a prereduced rhenium glucoheptonate or other transchelator can be used. Because reduction of perrhenate requires more stannous ion (typically above 200 µg/mL final concentration) than is needed for the reduction of Tc, extra care needs to be taken to ensure that the higher levels of stannous ion do not reduce sensitive disulfide bonds such as those present in disulfide-cyclized peptides. During radiolabeling with rhenium, similar procedures are used as are used with the Tc-99m. One method for the preparation of ReO metal complexes of the Tscg-Cys-ligands is by reacting the peptide with ReOCl$_3$(P(Ph$_3$)$_2$ but it is also possible to use other reduced species such as ReO(ethylenediamine)$_2$.

V. Methods of Administration

It should be noted that much of the discussion presented hereinbelow focuses on the use of the disclosed targetable constructs in the context of treating diseased tissue. The invention contemplates, however, the use of the bispecific antibodies and targetable constructs in treating and/or imaging normal tissue and organs using the methods described in U.S. Pat. Nos. 6,126,916; 6,077,499; 6,010,680; 5,776,095; 5,776,094; 5,776,093; 5,772,981; 5,753,206; 5,746,996; 5,697,902; 5,328,679; 5,128,119; 5,101,827; and 4,735,210, which are incorporated herein by reference. As used herein, the term "tissue" refers to tissues, including but not limited to, tissues from the ovary, thymus, parathyroid, bone marrow or spleen. An important use when targeting normal tissues is to identify and treat them when they are ectopic (i.e., displaced from their normal location), such as in endometriosis.

The administration of a bsAb and the targetable construct discussed above may be conducted by administering the bsAb at some time prior to administration of the therapeutic agent which is associated with the linker moiety. The doses and timing of the reagents can be readily devised by a skilled artisan, and are dependent on the specific nature of the reagents employed. If a bsAb-F(ab')$_2$ derivative is given first, then a waiting time of 1-6 days before administration of the targetable construct may be appropriate. If an IgG-Fab' bsAb conjugate is the primary targeting vector, then a longer waiting period before administration of the linker moiety may be indicated, in the range of 3-15 days. Alternatively, the bsAb and the targetable construct may be administered substantially at the same time in either a cocktail form or by administering one after the other.

A wide variety of diagnostic and therapeutic reagents can be advantageously conjugated to the targetable construct. Generally, diagnostic and therapeutic agents can include isotopes, drugs, toxins, cytokines, conjugates with cytokines, hormones, growth factors, conjugates, radionuclides, contrast agents, metals, cytotoxic drugs, and immune modulators. For example, gadolinium metal is used for magnetic resonance imaging and fluorochromes can be conjugated for photodynamic therapy. Moreover, contrast agents can be MRI contrast agents, such as gadolinium ions, lanthanum ions, manganese ions, iron, chromium, copper, cobalt, nickel, dysprosium, rhenium, europium, terbium, holmium, neodymium or other comparable label, CT contrast agents, and ultrasound contrast agents. Additional diagnotic agents can include fluorescent labeling compounds such as fluorescein isothiocyanate, rhodamine, phycoerytherin, phycocyanin, allophycocyanin, o-phthaldehyde and fluorescamine, chemiluminescent compounds including luminol, isoluminol, an aromatic acridinium ester, an imidazole, an acridinium salt and an oxalate ester, and bioluminescent compounds including luciferin, luciferase and aequorin. Radionuclides can also be used as diagnostic and/or therapeutic agents, including for example, $^{90}$Y, $^{111}$In, $^{131}$I, $^{99m}$Tc, $^{186}$Re, $^{188}$Re, $^{177}$Lu, $^{67}$Cu, $^{212}$Bi, $^{213}$Bi, and $^{211}$At.

Therapeutic agents also include, for example, chemotherapeutic drugs such as vinca alkaloids, anthracyclines, epidophyllotoxinw, taxanes, antimetabolites, alkylating agents, antibiotics, Cox-2 inhibitors, antimitotics, antiangiogenic and apoptotoic agents, particularly doxorubicin, methotrexate, taxol, CPT-11, camptothecans, and others from these and other classes of anticancer agents. Other useful therapuetic agents for the preparation of immunoconjugates and antibody fusion proteins include nitrogen mustards, alkyl sulfonates, nitrosoureas, triazenes, folic acid analogs, COX-2 inhibitors, pyrimidine analogs, purine analogs, platinum coordination complexes, hormones, and the like. Suitable therapeutic agents are described in REMINGTON'S PHARMACEUTICAL SCIENCES, 19th Ed. (Mack Publishing Co. 1995), and in GOODMAN AND GILMAN'S THE PHARMACOLOGICAL BASIS OF THERAPEUTICS, 7th Ed. (MacMillan Publishing Co. 1985), as well as revised editions of these publications. Other suitable therapeutic agents, such as experimental drugs, are known to those of skill in the art. Therapeutic agents may also include, without limitation, others drugs, prodrugs and/or toxins. The terms "drug," "prodrug," and "toxin" are defined throughout the specification. The terms "diagnostic agent" or "diagnosis" include, but are not limited to, detection agent, detection, or localization.

When the targetable construct includes a diagnostic agent, the bsAb is preferably administered prior to administration of the therapeutic agent. After sufficient time has passed for the bsAb to target to the diseased tissue, the diagnostic agent is administered, by means of the targetable construct, so that imaging can be performed. Tumors can be detected in body cavities by means of directly or indirectly viewing various structures to which light of the appropriate wavelength is delivered and then collected, or even by special detectors, such as radiation probes or fluorescent detectors, and the like. Lesions at any body site can be viewed so long as nonionizing radiation can be delivered and recaptured from these structures. For example, PET which is a high resolution, noninvasive, imaging technique can be used with the inventive antibodies and targetable constructs for the visualization of human disease. In PET, 511 keV gamma photons produced during positron annihilation decay are detected. X-ray, computed tomography (CT), MRI and gamma imaging (e.g., Single Photon Emission Computed Tomography (SPECT)) may also be utilized through use of a diagnostic agent that functions with these modalities.

As discussed earlier, the targetable construct may include radioactive diagnostic agents that emit 25-10,000 keV gamma-, beta-, alpha- and auger-particles and/or positrons. Examples of such agents include, but are not limited to $^{18}$F, $^{52}$Fe, $^{62}$Cu, $^{64}$Cu, $^{67}$Cu, $^{68}$Ga, $^{86}$Y, $^{89}$Zr $^{94m}$Tc, $^{94}$Tc, $^{99m}$Tc, $^{111}$In, $^{123}$I, $^{124}$I, $^{125}$I, $^{131}$I, $^{154-158}$Gd and $^{175}$Lu.

The present bsAbs or bsFabs can be used in a method of photodynamic therapy (PDT) as discussed in U.S. Pat. Nos. 6,096,289; 4,331,647; 4,818,709; 4,348,376; 4,361,544; 4,444,744; 5,851,527. In PDT, a photosensitizer, e.g., a hematoporphyrin derivative such as dihematoporphyrin ether, is administered to a subject. Anti-tumor activity is initiated by the use of light, e.g., 630 nm. Alternate photosensitizers can be utilized, including those useful at longer wavelengths, where skin is less photosensitized by the sun. Examples of such photosensitizers include, but are not limited to, benzoporphyrin monoacid ring A (BPD-MA), tin etiopurpurin (SnET2), sulfonated aluminum phthalocyanine (AlSPc) and lutetium texaphyrin (Lutex).

Additionally, in PDT, a diagnostic agent may be injected, for example, systemically, and laser-induced fluorescence can be used by endoscopes to detect sites of cancer which have accreted the light-activated agent. For example, this has been applied to fluorescence bronchoscopic disclosure of early lung tumors. Doiron et al. *Chest* 76:32 (1979). In another example, the antibodies and antibody fragments can be used in single photon emission. For example, a Tc-99m-labeled diagnostic agent can be administered to a subject following administration of the inventive antibodies or antibody fragments. The subject is then scanned with a gamma camera which produces single-photon emission computed tomographic images and defines the lesion or tumor site.

Therapeutically useful immunoconjugates can be obtained by conjugating photoactive agents or dyes to an antibody composite. Fluorescent and other chromogens, or dyes, such as porphyrins sensitive to visible light, have been used to detect and to treat lesions by directing the suitable light to the lesion. In therapy, this has been termed photoradiation, phototherapy, or photodynamic therapy (Jori et al. (eds.), *Photodynamic Therapy of Tumors and Other Diseases* (Libreria Progetto 1985); van den Bergh, *Chem. Britain* 22:430 (1986)). Moreover, monoclonal antibodies have been coupled with photoactivated dyes for achieving phototherapy. Mew et al., *J. Immunol.* 130:1473 (1983); idem., *Cancer Res.* 45:4380 (1985); Oseroff et al., *Proc. Natl. Acad. Sci. USA* 83:8744 (1986); idem., *Photochem. Photobiol.* 46:83 (1987); Hasan et al., *Prog. Clin. Biol. Res.* 288:471 (1989); Tatsuta et al., *Lasers Surg. Med.* 9:422 (1989); Pelegrin et al., *Cancer* 67:2529 (1991). However, these earlier studies did not include use of endoscopic therapy applications, especially with the use of antibody fragments or subfragments. Thus, the present invention contemplates the therapeutic use of immunoconjugates comprising photoactive agents or dyes.

Radiopaque and contrast materials are used for enhancing X-rays and computed tomography, and include iodine compounds, barium compounds, gallium compounds, thallium compounds, etc. Specific compounds include barium, diatrizoate, ethiodized oil, gallium citrate, iocarmic acid, iocetamic acid, iodamide, iodipamide, iodoxamic acid, iogulamide, iohexol, iopamidol, iopanoic acid, iopromic acid, iosefamic acid, ioseric acid, iosulamide meglumine, iosemetic acid, iotasul, iotetric acid, iothalamic acid, iotroxic acid, ioxaglic acid, ioxotrizoic acid, ipodate, meglumine, metrizamide, metrizoate, propyliodone, and thallous chloride. Ultrasound contrast material may also by used including dextran and liposomes, particularly gas-filled liposomes. In one embodiment, an immunomodulator, such as a cytokine, may also be conjugated to the therapeutic construct. As used herein, the term "immunomodulator" includes cytokines, stem cell growth factors, lymphotoxins, such as tumor necrosis factor (TNF), and hematopoietic factors, such as interleukins (e.g., interleukin-1 (IL-1), IL-2, IL-3, IL-6, IL-10, IL-12 and IL-18), colony stimulating factors (e.g., granulocyte-colony stimulating factor (G-CSF) and granulocyte macrophage-colony stimulating factor (GM-CSF)), interferons (e.g., interferons-α, -β and -γ), the stem cell growth factor designated "S1 factor," erythropoietin and thrombopoietin. Examples of suitable immunomodulator moieties include IL-2, IL-6, IL-10, IL-12, IL-18, interferon-γ, TNF-α, and the like.

The targetable construct may also be conjugated to an enzyme capable of activating a drug/prodrug at the target site or improving the efficacy of a normal therapeutic by controlling the body's detoxification pathways. Following administration of the bsAb, an enzyme conjugated to the targetable construct having a low MW hapten is administered. After the enzyme is pretargeted to the target site by bsAb:targetable construct binding, a cytotoxic drug is injected that is known to act at the target site. The drug may be one which is detoxified by the mammal's ordinary detoxification processes to form an intermediate of lower toxicity. For example, the drug may be converted into the potentially less toxic glucuronide in the liver. The detoxified intermediate can then be reconverted to its more toxic form by the pretargeted enzyme at the target site, and this enhances cytotoxicity at the target site.

Alternatively, an administered prodrug can be converted to an active drug by the pretargeted enzyme. The pretargeted enzyme improves the efficacy of the treatment by recycling the detoxified drug. This approach can be adopted for use with any enzyme-drug pair. Alternatively, the targetable construct with enzyme can be mixed with the targeting bsAb prior to administration to the patient. After a sufficient time has passed for the bsAb:targetable construct-conjugate to localize to the target site and for unbound targetable construct to clear from circulation, a prodrug is administered. As discussed above, the prodrug is then converted to the drug in situ by the pre-targeted enzyme.

Certain cytotoxic drugs that are useful for anticancer therapy are relatively insoluble in serum. Some are also quite toxic in an unconjugated form, and their toxicity is considerably reduced by conversion to prodrugs. Conversion of a poorly soluble drug to a more soluble conjugate, e.g., a glucuronide, an ester of a hydrophilic acid or an amide of a hydrophilic amine, will improve its solubility in the aqueous phase of serum and its ability to pass through venous, arterial or capillary cell walls and to reach the interstitial fluid bathing the tumor. Cleavage of the prodrug deposits the less soluble drug at the target site. Many examples of such prodrug-to-drug conversions are disclosed in U.S. Pat. No. 5,851,527, to Hansen.

Conversion of certain toxic substances such as aromatic or alicyclic alcohols, thiols, phenols and amines to glucuronides in the liver is the body's method of detoxifying them and making them more easily excreted in the urine. One type of antitumor drug that can be converted to such a substrate is epirubicin, a 4-epimer of doxorubicin (Adriamycin), which is an anthracycline glycoside and has been shown to be a substrate for human beta-D-glucuronidase See, e.g., Arcamone *Cancer Res.* 45:5995 (1985). Other analogues with fewer polar groups are expected to be more lipophilic and show greater promise for such an approach. Other drugs or toxins with aromatic or alicyclic alcohol, thiol or amine groups are candidates for such conjugate formation. These drugs, or other prodrug forms thereof, are suitable candidates for the site-specific enhancement methods of the present invention.

The prodrug CPT-11 (irinotecan) is converted in vivo by carboxylesterase to the active metabolite SN-38. One application of the invention, therefore, is to use a bsAb targeted against a tumor and a hapten (e.g. di-DTPA) followed by injection of a di-DTPA-carboxylesterase conjugate. Once a suitable tumor-to-background localization ratio has been achieved, the CPT-11 is given and the tumor-localized carboxylesterase serves to convert CPT-11 to SN-38 at the tumor. Due to its poor solubility, the active SN-38 will remain in the vicinity of the tumor and, consequently, will exert an effect on adjacent tumor cells that are negative for the antigen being targeted. This is a further advantage of the method. Modified forms of carboxylesterases have been described and are within the scope of the invention. See, e.g., Potter et al., *Cancer Res.* 58:2646-2651 (1998) and Potter et al., *Cancer Res.* 58:3627-3632 (1998).

Etoposide is a widely used cancer drug that is detoxified to a major extent by formation of its glucuronide and is within the scope of the invention. See, e.g., Hande et al. *Cancer Res.* 48:1829-1834 (1988). Glucuronide conjugates can be prepared from cytotoxic drugs and can be injected as therapeutics for tumors pre-targeted with mAb-glucuronidase conjugates. See, e.g., Wang et al. *Cancer Res.* 52:44844491 (1992). Accordingly, such conjugates also can be used with the pre-targeting approach described here. Similarly, designed prodrugs based on derivatives of daunomycin and doxorubicin have been described for use with carboxylesterases and glucuronidases. See, e.g., Bakina et al. *J. Med Chem.* 40:4013-4018 (1997). Other examples of prodrug/enzyme pairs that can be used within the present invention include, but are not limited to, glucuronide prodrugs of hydroxy derivatives of phenol mustards and beta-glucuronidase; phenol mustards or CPT-11 and carboxypeptidase; methotrexate-substituted alpha-amino acids and carboxypeptidase A; penicillin or cephalosporin conjugates of drugs such as 6-mercaptopurine and doxorubicin and beta-lactamase; etoposide phosphate and alkaline phosphatase.

The enzyme capable of activating a prodrug at the target site or improving the efficacy of a normal therapeutic by controlling the body's detoxification pathways may alternatively be conjugated to the hapten. The enzyme-hapten conjugate is administered to the subject following administration of the pre-targeting bsAb and is directed to the target site. After the enzyme is localized at the target site, a cytotoxic drug is injected, which is known to act at the target site, or a prodrug form thereof which is converted to the drug in situ by the pretargeted enzyme. As discussed above, the drug is one which is detoxified to form an intermediate of lower toxicity, most commonly a glucuronide, using the mammal's ordinary detoxification processes. The detoxified intermediate, e.g., the glucuronide, is reconverted to its more toxic form by the pretargeted enzyme and thus has enhanced cytotoxicity at the target site. This results in a recycling of the drug. Similarly, an administered prodrug can be converted to an active drug through normal biological processes. The pretargeted enzyme improves the efficacy of the treatment by recycling the detoxified drug. This approach can be adopted for use with any enzyme-drug pair.

In an alternative embodiment, the enzyme-hapten conjugate can be mixed with the targeting bsAb prior to administration to the patient. After a sufficient time has passed for the enzyme-hapten-bsAb conjugate to localize to the target site and for unbound conjugate to clear from circulation, a prodrug is administered. As discussed above, the prodrug is then converted to the drug in situ by the pre-targeted enzyme.

The invention further contemplates the use of the inventive bsAb and the diagnostic agent(s) in the context of Boron Neutron Capture Therapy (BNCT) protocols. BNCT is a binary system designed to deliver ionizing radiation to tumor cells by neutron irradiation of tumor-localized $^{10}B$ atoms. BNCT is based on the nuclear reaction which occurs when a stable isotope, isotopically enriched $^{10}B$ (present in 19.8% natural abundance), is irradiated with thermal neutrons to produce an alpha particle and a $^{7}Li$ nucleus. These particles have a path length of about one cell diameter, resulting in high linear energy transfer. Just a few of the short-range 1.7 MeV alpha particles produced in this nuclear reaction are sufficient to target the cell nucleus and destroy it. Success with BNCT of cancer requires methods for localizing a high concentration of $^{10}B$ at tumor sites, while leaving non-target organs essentially boron-free. Compositions and methods for treating tumors in subjects using pre-targeting bsAb for BNCT are described in U.S. Pat. No. 6,228,362 and can easily be modified for the purposes of the present invention.

In another embodiment of the present invention, the peptide backbone of the targetable construct is conjugated to a prodrug. The pre-targeting bsAb is administered to the patient and allowed to localize to the target and substantially clear circulation. At an appropriate later time, a targetable construct comprising a prodrug, for example poly-glutamic acid $(SN-38-ester)_{10}$, is given, thereby localizing the prodrug specifically at the tumor target. It is known that tumors have increased amounts of enzymes released from intracellular sources due to the high rate of lysis of cells within and around tumors. A practitioner can capitalize on this fact by appropriately selecting prodrugs capable of being activated by these enzymes. For example, carboxylesterase activates the prodrug poly-glutamic acid $(SN-38-ester)_{10}$ by cleaving the ester bond of the poly-glutamic acid $(SN-38-ester)_{10}$ releasing large concentrations of free SN-38 at the tumor. Alternatively, the appropriate enzyme also can be targeted to the tumor site.

After cleavage from the targetable construct, the drug is internalized by the tumor cells. Alternatively, the drug can be internalized as part of an intact complex by virtue of cross-linking at the target. The targetable construct can induce internalization of tumor-bound bsAb and thereby improve the efficacy of the treatment by causing higher levels of the drug to be internalized.

A variety of peptide carriers are well-suited for conjugation to prodrugs, including polyamino acids, such as polylysine, polyglutamic (E) and aspartic acids (D), including D-amino acid analogs of the same, co-polymers, such as poly(Lys-Glu) {poly[KE]}, advantageously from 1:10 to 10:1. Copolymers based on amino acid mixtures such as poly(Lys-Ala-Glu-Tyr) (KAEY; 5:6:2:1) can also be employed. Smaller polymeric carriers of defined molecular weight can be produced by solid-phase peptide synthesis techniques, readily producing polypeptides of from 2-50 residues in chain length. A second advantage of this type of reagent, other than precise structural definition, is the ability to place single or any desired number of chemical handles at certain points in the chain. These can be used later for attachment of recognition and therapeutic haptens at chosen levels of each moiety.

Poly(ethylene) glycol [PEG] has desirable in vivo properties for a bi-specific antibody prodrug approach. Ester linkages between the hydroxyl group of SN-38 and both ends of a standard di-hydroxyl PEG can be introduced by insertion of diacids such as succinic acid between the SN-38 and PEG hydroxyl groups, to generate species such as SN-38-O—CO(CH2)$_2$CO—O-PEG-0-CO(CH2)$_2$CO—OSN-38. The di-SN-38-PEG produced can be considered as the shortest member of the class of SN-38-polymer prodrugs. The desirable in vivo properties of PEG derivatives and the limited loading capacity due to their dimeric functionality led to the preparation of PEG co-polymers having greater hapten-bearing capacity such as those described by Poiani et al. See, e.g., Poiani et al. *Bioconjugate Chem.,* 5:621-630, 1994. PEG derivatives are activated at both ends as their bis(succinimidyl)carbonate derivatives and co-polymerized with multifunctional diamines such as lysine. The product of such co-polymerization, containing (-Lys(COOH)-PEG-Lys(COOH)-PEG-)$_n$ repeat units wherein the lysyl carboxyl group is not involved in the polymerization process, can be used for attachment of SN-38 residues. The SN-38 residues are reacted with the free carboxyl groups to produce SN-38 esters of the (-Lys-(COOH)-PEG-Lys(COOH)-PEG-)$_n$, chain.

Other synthetic polymers that can be used to carry recognition haptens and prodrugs include N-(2-hydroxypropyl) methacrylamide (HMPA) copolymers, poly(styrene-co-maleic acid/anhydride (SMA), poly(divinylether maleic anhydride) (DIVEMA), polyethyleneimine, ethoxylated polyethylene-imine, starburst dendrimers and poly(N-vinylpyrrolidone) (PVP). As an example, DIVEMA polymer comprised of multiple anhydride units is reacted with a limited amount of SN-38 to produce a desired substitution ratio of drug on the polymer backbone. Remaining anhydride groups are opened under aqueous conditions to produce free carboxylate groups. A limited number of the free carboxylate groups are activated using standard water-soluble peptide coupling agents, e.g. 1-ethyl-3-(3-dimethylaminopropyl)carbodiimide hydrochloride (EDC), and coupled to a recognition moiety bearing a free amino group. An example of the latter is histamine, to which antibodies have been raised in the past.

A variety of prodrugs can be conjugated to the targetable construct. The above exemplifications of polymer use are concerned with SN-38, the active metabolite of the prodrug CPT-11 (irinotecan). SN-38 has an aromatic hydroxyl group that was used in the above descriptions to produce aryl esters susceptible to esterase-type enzymes. Similarly the camptothecin analog topotecan, widely used in chemotherapy, has an available aromatic hydroxyl residue that can be used in a similar manner as described for SN-38, producing esterase-susceptible polymer-prodrugs.

Doxorubicin also contains aromatic hydroxyl groups that can be coupled to carboxylate-containing polymeric carriers using acid-catalyzed reactions similar to those described for the camptothecin family. Similarly, doxorubicin analogs like daunomycin, epirubicin and idarubicin can be coupled in the same manner. Doxorubicin and other drugs with amino 'chemical handles' active enough for chemical coupling to polymeric carriers can be effectively coupled to carrier molecules via these free amino groups in a number of ways. Polymers bearing free carboxylate groups can be activated in situ (EDC) and the activated polymers mixed with doxorubicin to directly attach the drug to the side-chains of the polymer via amide bonds. Amino-containing drugs can also be coupled to amino-pendant polymers by mixing commercially available and cleavable cross-linking agents, such as ethylene glycobis(succinimidylsuccinate) (EGS, Pierce Chemical Co., Rockford, Ill.) or bis-[2-(succinimido-oxycarbonyloxy) ethyl]sulfone (BSOCOES, Molecular Biosciences, Huntsville, Ala.), to cross-link the two amines as two amides after reaction with the bis(succinimidyl) ester groups. This is advantageous as these groups remain susceptible to enzymatic cleavage. For example, (doxorubicin-EGS)$_n$-polylysine remains susceptible to enzymatic cleavage of the diester groups in the EGS linking chain by enzymes such as esterases. Doxorubicin also can be conjugated to a variety of peptides, for example, HyBnK(DTPA)YK(DTPA)-NH$_2$, using established procedures (HyBn=p-H$_2$NNHC$_6$H$_4$CO$_2$H). See Kaneko et al, *J. Bioconjugate Chem.,* 2: 133-141, 1991.

In one preferred embodiment, the therapeutic conjugate comprises doxorubicin coupled to a carrier comprising amine residues and a chelating agent, such as DTPA, to form a DTPA-peptide-doxorubicin conjugate, wherein the DTPA forms the recognition moiety for a pretargeted bsAb. In some embodiments, the carrier comprises a tyrosyl-lysine dipeptide, e.g., D-Tyr-D-Lys(DTPA)-NH$_2$, and can comprise D-Lys(DTPA)-D-Tyr-D-Lys(DTPA)-NH$_2$. Doxorubicin phenyl hydrazone conjugates to bis-DPTA containing peptides are particularly desirable in a therapeutic context.

Methotrexate also has an available amino group for coupling to activated carboxylate-containing polymers, in a similar manner to that described for doxorubicin. It also has two glutamyl carboxyl groups (alpha and gamma) that can be activated for coupling to amino-group containing polymers. The free carboxylate groups of methotrexate can be activated in situ (EDC) and the activated drug mixed with an amino-containing polymer to directly attach the drug to the side-chains of the polymer via amide bonds. Excess unreacted or cross-reacted drug is separated readily from the polymer-drug conjugate using size-exclusion or ion-exchange chromatography.

Maytansinoids and calicheamicins (such as esperamycin) contain mixed di- and tri-sulfide bonds that can be cleaved to generate species with a single thiol useful for chemical manipulation. The thiomaytensinoid or thioespera-mycin is first reacted with a cross-linking agent such as a maleimido-peptide that is susceptible to cleavage by peptidases. The C-terminus of the peptide is then activated and coupled to an amino-containing polymer such as polylysine.

In still other embodiments, the bi-specific antibody-directed delivery of therapeutics or prodrug polymers to in vivo targets can be combined with bi-specific antibody delivery of radionuclides, such that combination chemotherapy and radioimmunotherapy is achieved. Each therapy can be conjugated to the targetable construct and administered simultaneously, or the nuclide can be given as part of a first targetable construct and the drug given in a later step as part of a second targetable construct. In one simple embodiment, a peptide containing a single prodrug and a single nuclide is constructed. For example, the tripeptide Ac-D-Glu-D-Gly-D-Lys-NH$_2$ can be used as a carrier portion of a targetable construct, whereby SN-38 is attached to the gamma glutamyl carboxyl group as an aryl ester, while the chelate DOTA is attached to the epsilon amino group as an amide, to produce the complex Ac-D-Glu(SN-38)-D-Gly-D-Lys(DOTA)-NH$_2$. The DOTA chelate can then be radiolabeled with various metals for imaging and therapy purposes including In-111, Y-90, Sm-153, Lu-177 and Zr-89. As the metal-DOTA complex may represent the recognizable hapten on the targetable construct, the only requirement for the metal used as part of the DOTA complex is that the secondary recognition antibody also used recognizes that particular metal-DOTA complex at a sufficiently high affinity. Generally, this affinity (log K$_a$) is between 6-11. Polymeric peptides such as poly[D-Glu(SN- $38)_{10}$-D-Lys(Y-90-DOTA)$_2$] can be given as readily as the more chemically defined lower MW reagent above, and are indeed preferred. Also, triply substituted polymers can be used, such as poly[D-Glu(Sn-38)$_{10}$-D-Lys(Y-90-DOTA)$_n$ (histamine-succinate)$_m$, where n and m are integers, such that the recognition agent is independent of the radioimmunotherapy agent. The prodrug is activated by carboxylesterases present at the tumor site or by carboxylesterases targeted to the site using a second targetable construct.

Alternatively, a combination therapy can be achieved by administering the chemotherapy and radioimmunotherapy agents in separate steps. For example, a patient expressing CEA-tumors is first administered bsAb with at least one arm which specifically binds CEA and at least one other arm which specifically binds the targetable construct whose hapten is a conjugate of yttrium-DOTA. Later the patient is treated with a targetable construct comprising a conjugate of yttrium-DOTA-beta-glucuronidase. After sufficient time for bsAb and enzyme localization and clearance, a second targetable construct, comprising Ac-D-Glu(SN-38)-D-Gly-D-Lys(Y-90-DOTA)-NH$_2$, is given. The second targetable construct localizes to the tumor by virtue of bsAb at the tumor that are not already bound to a first targetable construct. First targetable constructs which are localized to the target site act on the Ac-D-Glu(SN-38)-D-Gly-D-Lys(Y-90-DOTA)-NH$_2$ to liberate the free SN-38 drug. Localization of both the prodrug and its respective enzyme to the target site enhances the production of active drug by ensuring that the enzyme is not substrate limited. This embodiment constitutes a marked improvement of current prodrug methodologies currently practiced in the art.

Another advantage of administering the prodrug-polymer in a later step, after the nuclide has been delivered as part of a previously given targetable construct, is that the synergistic effects of radiation and drug therapy can be manipulated and, therefore, maximized. It is hypothesized that tumors become more 'leaky' after RAIT due to radiation damage. This can allow a polymer-prodrug to enter a tumor more completely and deeply. This results in improved chemotherapy.

Alternatively, the RAIT therapy agent can be attached to bsAb rather than to the targetable construct. For example, an anti-CEA×anti-DTPA bsAb conjugated to Y-90-DOTA is administered first to a patient with CEA-expressing tumors. In this instance, advantage is taken of the selectivity of certain anti-chelate mabs in that an anti-indium-DTPA antibody do not bind to a yttrium-DOTA chelate. After the Y-90-DOTA-anti-CEA×anti-indium-DTPA has maximized at the tumor and substantially cleared non-target tissue, a conjugate of indium-DTPA-glucuronidase is injected and localized specifically to the CEA tumor sites. The patient is then injected with a polymer-prodrug such as poly(Glu)(SN-38)$_{10}$. The latter is cleaved selectively at the tumor to active monomeric SN-38, successfully combining chemotherapy with the previously administered RAIT.

It should also be noted that a bispecific antibody or antibody fragment can be used in the present method, with at least one binding site specific to an antigen at a target site and at least one other binding site specific to the enzyme component of the antibody-enzyme conjugate. Such an antibody can bind the enzyme prior to injection, thereby obviating the need to covalently conjugate the enzyme to the antibody, or it can be injected and localized at the target site and, after non-targeted antibody has substantially cleared from the circulatory system of the mammal, enzyme can be injected in an amount and by a route which enables a sufficient amount of the enzyme to reach a localized antibody or antibody fragment and bind to it to form the antibody-enzyme conjugate in situ.

It should also be noted that the invention also contemplates the use of multivalent target binding proteins which have at least three different target binding sites as described in Patent Appl. Ser. No. 60/220,782. Multivalent target binding proteins have been made by cross-linking several Fab-like fragments via chemical linkers. See U.S. Pat. Nos. 5,262,524; 5,091,542 and Landsdorp et al., *Euro. J Immunol.* 16: 679-83 (1986). Multivalent target binding proteins also have been made by covalently linking several single chain Fv molecules (scFv) to form a single polypeptide. See U.S. Pat. No. 5,892,020. A multivalent target binding protein which is basically an aggregate of scFv molecules has been disclosed in U.S. Pat. Nos. 6,025,165 and 5,837,242. A trivalent target binding protein comprising three scFv molecules has been described in Krott et al., *Protein Engineering* 10(4): 423-433 (1997).

A clearing agent may be used which is given between doses of the bsAb and the targetable construct. The present inventors have discovered that a clearing agent of novel mechanistic action may be used with the invention, namely a glycosylated anti-idiotypic Fab' fragment targeted against the disease targeting arm(s) of the bsAb. Anti-CEA (MN-14 Ab)×anti-peptide bsAb is given and allowed to accrete in disease targets to its maximum extent. To clear residual bsAb, an anti-idiotypic Ab to MN-14, termed WI2, is given, preferably as a glycosylated Fab' fragment. The clearing agent binds to the bsAb in a monovalent manner, while its appended glycosyl residues direct the entire complex to the liver, where rapid metabolism takes place. Then the therapeutic or diagnostic agent which is associated with the targetable construct is given to the subject. The WI2 Ab to the MN-14 arm of the bsAb has a high affinity and the clearance mechanism differs from other disclosed mechanisms (see Goodwin et al., ibid), as it does not involve cross-linking, because the WI2-Fab' is a monovalent moiety.

In accordance with yet another aspect of the present invention, the present invention provides a kit suitable for treating or identifying diseased tissues in a patient, comprising a bi-specific antibody or antibody fragment having at least one arm that specifically binds a targeted tissue and at least one other arm that specifically binds a targetable construct, a first targetable construct which comprises a carrier portion which comprises or bears at least one epitope recognizable by the at least one other arm of the bi-specific antibody or antibody fragment, and one or more conjugated therapeutic or diagnostic agents, or enzymes, and, optionally, a clearing composition useful for clearing non-localized antibodies and antibody fragments. The kit may optionally contain a prodrug when the first targetable construct comprises an enzyme capable of converting the prodrug to a drug at the target site, an enzyme that is capable of reconverting a detoxified intermediate of a drug to a toxic form, and, therefore, of increasing the toxicity of the drug at the target site, or an enzyme capable of reconverting a prodrug which is activated in the patient through natural processes and is subject to detoxification by conversion to an intermediate of lower toxicity from the detoxified intermediate to a toxic form, and, therefore, of increasing the toxicity of the drug at the target site. A second targetable construct may also be used which comprises a carrier portion which comprises or bears at least one epitope recognizable by the at least one other arm of the bi-specific antibody or antibody fragment, and a prodrug, when the enzyme is capable of converting the prodrug to a drug at the target site. Instruments which facilitate identifying or treating diseased tissue also can be included in the kit. Examples include, but are not limited to application devices, such as syringes. Solutions required for utilizing the disclosed invention for identifying or treating diseased tissue also can be included in the kit.

The targetable construct or antibody fragment may be administered intravenously, intraarterially, intraoperatively, endoscopically, intraperitoneally, intramuscularly, subcutaneously, intrapleurally, intrathecally, by perfusion through a regional catheter, or by direct intralesional injection, and can be by continuous infusion or by single or multiple boluses or through other methods known to those skilled in the art for diagnosing (detecting) and treating diseased tissue. Further, the targetable construct may include agents for other methods of detecting and treating diseased tissue including, without limitation, conjugating dextran or liposome formulations to the targetable construct for use with ultrasound, or other contrast agents for use with other imaging modalities, such as X-ray, CT, PET, SPECT and ultrasound, as previously described.

VI. Methods for Raising Antibodies

Abs to peptide backbones and/or haptens are generated by well-known methods for Ab production. For example, injection of an immunogen, such as (peptide)$_n$-KLH, wherein KLH is keyhole limpet hemocyanin, and n=1-30, in complete Freund's adjuvant, followed by two subsequent injections of the same immunogen suspended in incomplete Freund's adjuvant into immunocompetent animals, is followed three days after an i.v. boost of antigen, by spleen cell harvesting. Harvested spleen cells are then fused with Sp2/0-Ag14 myeloma cells and culture supernatants of the resulting clones analyzed for anti-peptide reactivity using a direct-binding ELISA. Fine specificity of generated Abs can be analyzed for by using peptide fragments of the original immunogen. These fragments can be prepared readily using an automated peptide synthesizer. For Ab production, enzyme-deficient hybridomas are isolated to enable selection of fused cell lines. This technique also can be used to raise antibodies to one or more of the chelates comprising the linker, e.g., In(III)-DTPA chelates. Monoclonal mouse antibodies to an In(III)-di-DTPA are known (Barbet '395 supra).

The antibodies used in the present invention are specific to a variety of cell surface or intracellular tumor-associated antigens as marker substances. These markers may be substances produced by the tumor or may be substances which accumulate at a tumor site, on tumor cell surfaces or within tumor cells, whether in the cytoplasm, the nucleus or in various organelles or sub-cellular structures. Among such tumor-associated markers are those disclosed by Herberman, "Immunodiagnosis of Cancer", in Fleisher ed., "The Clinical Biochemistry of Cancer", page 347 (American Association of Clinical Chemists, 1979) and in U.S. Pat. Nos. 4,150,149; 4,361,544; and 4,444,744. See also U.S. Pat. No. 5,965,132, to Thorpe et al., U.S. Pat. No. 6,004,554, to Thorpe et al., U.S. Pat. No. 6,071,491, to Epstein et al., U.S. Pat. No. 6,017,514, to Epstein et al., U.S. Pat. No. 5,882,626, to Epstein et al., U.S. Pat. No. 5,019,368, to Epstein et al., and U.S. Pat. No. 6,342,221, to Thorpe et al., all of which are incorporated herein by reference.

Tumor-associated markers have been categorized by Herberman, supra, in a number of categories including oncofetal antigens, placental antigens, oncogenic or tumor virus associated antigens, tissue associated antigens, organ associated antigens, ectopic hormones and normal antigens or variants thereof. Occasionally, a sub-unit of a tumor-associated marker is advantageously used to raise antibodies having higher tumor-specificity, e.g., the beta-subunit of human chorionic gonadotropin (HCG) or the gamma region of carcino embryonic antigen (CEA), which stimulate the production of antibodies having a greatly reduced cross-reactivity to non-tumor substances as disclosed in U.S. Pat. Nos. 4,361, 644 and 4,444,744. Markers of tumor vasculature (e.g., VEGF), of tumor necrosis (Epstein patents), of membrane receptors (e.g., folate receptor, EGFR), of transmembrane antigens (e.g., PSMA), and of oncogene products can also serve as suitable tumor-associated targets for antibodies or antibody fragments. Markers of normal cell constitutents which are expressed copiously on tumor cells, such as B-cell complex antigens (e.g., CD19, CD20, CD21, CD22, CD23, and HLA-DR on B-cell malignancies), as well as cytokines expressed by certain tumor cells (e.g., IL-2 receptor in T-cell malignancies) are also suitable targets for the antibodies and antibody fragments of this invention. Other well-known tumor associated antigens that can be targeted by the antibodies and antibody fragments of this invention include, but are not limited to, CEA, CSAp, TAG-72, MUC-1, MUC-2, MUC-3, MUC-4, EGP-1, EGP-2, BrE3, PAM-4, KC-4, A3, KS-1, PSMA, PSA, tenascin, T101, S100, MAGE, HLA-DR, CD19, CD20, CD22, CD30, and CD74.

Another marker of interest is transmembrane activator and CAML-interactor (TACI). See Yu et al. *Nat. Immunol.* 1:252-256 (2000). Briefly, TACI is a marker for B-cell malignancies (e.g., lymphoma). Further it is known that TACI and B-cell maturation antigen (BCMA) are bound by the tumor necrosis factor homolog a proliferation-inducing ligand (APRIL). APRIL stimulates in vitro proliferation of primary B and T cells and increases spleen weight due to accumulation of B cells in vivo. APRIL also competes with TALL-I (also called BLyS or BAFF) for receptor binding. Soluble BCMA and TACI specifically prevent binding of APRIL and block APRIL-stimulated proliferation of primary B cells. BCMA-Fc also inhibits production of antibodies against keyhole limpet hemocyanin and Pneumovax in mice, indicating that APRIL and/or TALL-I signaling via BCMA and/or TACI are required for generation of humoral immunity. Thus, APRIL-TALL-I and BCMA-TACI form a two ligand-two receptor pathway involved in stimulation of B and T cell function.

After the initial raising of antibodies to the immunogen, the antibodies can be sequenced and subsequently prepared by recombinant techniques. Humanization and chimerization of murine antibodies and antibody fragments are well known to those skilled in the art. For example, humanized monoclonal antibodies are produced by transferring mouse complementary determining regions from heavy and light variable chains of the mouse immunoglobulin into a human variable domain, and then, substituting human residues in the framework regions of the murine counterparts. The use of antibody components derived from humanized monoclonal antibodies obviates potential problems associated with the immunogenicity of murine constant regions. General techniques for cloning murine immunoglobulin variable domains are described, for example, by the publication of Orlandi et al., *Proc. Nat'l Acad. Sci. USA* 86: 3833 (1989), which is incorporated by reference in its entirety. Techniques for producing humanized Mabs are described, for example, by Jones et al., *Nature* 321: 522 (1986), Riechmann et al., *Nature* 332: 323 (1988), Verhoeyen et al., *Science* 239: 1534 (1988), Carter et al., *Proc. Nat'l Acad. Sci. USA* 89: 4285 (1992), Sandhu, *Crit. Rev. Biotech.* 12: 437 (1992), and Singer et al., *J. Immun.* 150: 2844 (1993), each of which is hereby incorporated by reference.

Alternatively, fully human antibodies can be obtained from transgenic non-human animals. See, e.g., Mendez et al., *Nature Genetics*, 15: 146-156 (1997); U.S. Pat. No. 5,633, 425. For example, human antibodies can be recovered from transgenic mice possessing human immunoglobulin loci. The mouse humoral immune system is humanized by inactivating the endogenous immunoglobulin genes and introducing human immunoglobulin loci. The human immunoglobulin loci are exceedingly complex and comprise a large number of discrete segments which together occupy almost 0.2% of the human genome. To ensure that transgenic mice are capable of producing adequate repertoires of antibodies, large portions of human heavy- and light-chain loci must be introduced into the mouse genome. This is accomplished in a stepwise process beginning with the formation of yeast artificial chromosomes (YACs) containing either human heavy- or light-chain immunoglobulin loci in germline configuration. Since each insert is approximately 1 Mb in size, YAC construction requires homologous recombination of overlapping fragments of the immunoglobulin loci. The two YACs, one containing the heavy-chain loci and one containing the light-chain loci, are introduced separately into mice via fusion of YAC-containing yeast spheroblasts with mouse embryonic stem cells. Embryonic stem cell clones are then microinjected into mouse blastocysts. Resulting chimeric males are screened for their ability to transmit the YAC through their germline and are bred with mice deficient in murine antibody production. Breeding the two transgenic strains, one containing the human heavy-chain loci and the other containing the human light-chain loci, creates progeny which produce human antibodies in response to immunization.

Unrearranged human immunoglobulin genes also can be introduced into mouse embryonic stem cells via microcell-mediated chromosome transfer (MMCT). See, e.g., Tomizuka et al., *Nature Genetics*, 16: 133 (1997). In this methodology microcells containing human chromosomes are fused with mouse embryonic stem cells. Transferred chromosomes are stably retained, and adult chimeras exhibit proper tissue-specific expression.

As an alternative, an antibody or antibody fragment of the present invention may be derived from human antibody fragments isolated from a combinatorial immunoglobulin library. See, e.g., Barbas et al., *METHODS: A Companion to Methods in Enzymology* 2: 119 (1991), and Winter et al., *Ann. Rev. Immunol.* 12: 433 (1994), which are incorporated by reference. Many of the difficulties associated with generating monoclonal antibodies by B-cell immortalization can be overcome by engineering and expressing antibody fragments in *E. coli*, using phage display. To ensure the recovery of high affinity, monoclonal antibodies a combinatorial immunoglobulin library must contain a large repertoire size. A typical strategy utilizes mRNA obtained from lymphocytes or spleen cells of immunized mice to synthesize cDNA using reverse transcriptase. The heavy- and light-chain genes are amplified separately by PCR and ligated into phage cloning vectors. Two different libraries are produced, one containing the heavy-chain genes and one containing the light-chain genes. Phage DNA is islolated from each library, and the heavy- and light-chain sequences are ligated together and packaged to form a combinatorial library. Each phage contains a random pair of heavy- and light-chain cDNAs and upon infection of *E. coli* directs the expression of the antibody chains in infected cells. To identify an antibody that recognizes the antigen of interest, the phage library is plated, and the antibody molecules present in the plaques are transferred to filters. The filters are incubated with radioactively labeled antigen and then washed to remove excess unbound ligand. A radioactive spot on the autoradiogram identifies a plaque that contains an antibody that binds the antigen. Cloning and expression vectors that are useful for producing a human immunoglobulin phage library can be obtained, for example, from STRATAGENE Cloning Systems (La Jolla, Calif.).

A similar strategy can be employed to obtain high-affinity scFv. See, e.g., Vaughn et al., *Nat. Biotechnol.*, 14: 309-314 (1996). An scFv library with a large repertoire can be constructed by isolating V-genes from non-immunized human donors using PCR primers corresponding to all known $V_H$, $V_\kappa$ and $V_\lambda$ gene families. Following amplification, the $V_\kappa$ and $V_\lambda$ pools are combined to form one pool. These fragments are ligated into a phagemid vector. The scFv linker, $(Gly_4, Ser)_3$, is then ligated into the phagemid upstream of the $V_L$ fragment. The $V_H$ and linker-$V_L$ fragments are amplified and assembled on the $J_H$ region. The resulting $V_H$-linker-$V_L$ fragments are ligated into a phagemid vector. The phagemid library can be panned using filters, as described above, or using immunotubes (Nunc; Maxisorp). Similar results can be achieved by constructing a combinatorial immunoglobulin library from lymphocytes or spleen cells of immunized rabbits and by expressing the scfv constructs in *P. pastoris*. See, e.g., Ridder et al., *Biotechnology*, 13: 255-260 (1995). Additionally, following isolation of an appropriate scFv, antibody fragments with higher binding affinities and slower dissociation rates can be obtained through affinity maturation processes such as CDR3 mutagenesis and chain shuffling. See, e.g., Jackson et al., *Br. J Cancer*, 78: 181-188 (1998); Osbourn et al., *Immunotechnology*, 2: 181-196(1996).

Another form of an antibody fragment is a peptide coding for a single CDR. CDR peptides ("minimal recognition units") can be obtained by constructing genes encoding the CDR of an antibody of interest. Such genes are prepared, for example, by using the polymerase chain reaction to synthesize the variable region from RNA of antibody-producing cells. See, for example, Larrick et al., *Methods: A Companion to Methods in Enzymology* 2:106 (1991); Courtenay-Luck, "Genetic Manipulation of Monoclonal Antibodies," in MONOCLONAL ANTIBODIES: PRODUCTION, ENGINEERING AND CLINICAL APPLICATION, Ritter et al. (eds.), pages 166-179 (Cambridge University Press 1995); and Ward et al., "Genetic Manipulation and Expression of Antibodies," in MONOCLONAL ANTIBODIES: PRINCIPLES AND APPLICATIONS, Birch et al., (eds.), pages 137-185 (Wiley-Liss, Inc. 1995).

The bsAbs can be prepared by techniques known in the art, for example, an anti-CEA tumor Ab and an anti-peptide Ab are both separately digested with pepsin to their respective $F(ab')_2$s. The anti-CEA-Ab-$F(ab')_2$ is reduced with cysteine to generate Fab' monomeric units which are further reacted with the cross-linker bis(maleimido) hexane to produce Fab'-maleimide moieties. The anti-peptide Ab-$F(ab')_2$ is reduced with cysteine and the purified, recovered anti-peptide Fab'-SH reacted with the anti-CEA-Fab'-maleimide to generate the Fab'×Fab' bi-specific Ab. Alternatively, the anti-peptide Fab'-SH fragment may be coupled with the anti-CEA $F(ab')_2$ to generate a $F(ab')_2$×Fab' construct, or with anti-CEA IgG to generate an IgG×Fab' bi-specific construct. In one embodiment, the IgG×Fab' construct can be prepared in a site-specific manner by attaching the antipeptide Fab' thiol group to anti-CEA IgG heavy-chain carbohydrate which has been periodate-oxidized, and subsequently activated by reaction with a commercially available hydrazide-maleimide cross-linker. The component Abs used can be chimerized or humanized by known techniques. A chimeric antibody is a recombinant protein that contains the variable domains and complementary determining regions derived from a rodent antibody, while the remainder of the antibody molecule is derived from a human antibody. Humanized antibodies are recombinant proteins in which murine complementarity determining regions of a monoclonal antibody have been transferred from heavy and light variable chains of the murine immunoglobulin into a human variable domain.

A variety of recombinant methods can be used to produce bi-specific antibodies and antibody fragments. For example, bi-specific antibodies and antibody fragments can be produced in the milk of transgenic livestock. See, e.g., Colman, A., *Biochem. Soc. Symp.*, 63: 141-147, 1998; U.S. Pat. No. 5,827,690. Two DNA constructs are prepared which contain, respectively, DNA segments encoding paired immunoglobulin heavy and light chains. The fragments are cloned into expression vectors which contain a promoter sequence that is preferentially expressed in mammary epithelial cells. Examples include, but are not limited to, promoters from rabbit, cow and sheep casein genes, the cow α-lactoglobulin gene, the sheep β-lactoglobulin gene and the mouse whey acid protein gene. Preferably, the inserted fragment is flanked on its 3' side by cognate genomic sequences from a mammary-specific gene. This provides a polyadenylation site and transcript-stabilizing sequences. The expression cassettes are coinjected into the pronuclei of fertilized, mammalian eggs, which are then implanted into the uterus of a recipient female and allowed to gestate. After birth, the progeny are screened for the presence of both transgenes by Southern analysis. In order for the antibody to be present, both heavy and light chain genes must be expressed concurrently in the same cell. Milk from transgenic females is analyzed for the presence and functionality of the antibody or antibody fragment using standard immunological methods known in the art. The antibody can be purified from the milk using standard methods known in the art.

A chimeric Ab is constructed by ligating the cDNA fragment encoding the mouse light variable and heavy variable domains to fragment encoding the C domains from a human antibody. Because the C domains do not contribute to antigen binding, the chimeric antibody will retain the same antigen specificity as the original mouse Ab but will be closer to human antibodies in sequence. Chimeric Abs still contain some mouse sequences, however, and may still be immunogenic. A humanized Ab contains only those mouse amino acids necessary to recognize the antigen. This product is constructed by building into a human antibody framework the amino acids from mouse complementarity determining regions.

Other methods for producing bsAbs include engineered recombinant Abs which have additional cysteine residues so that they crosslink more strongly than the more common immunoglobulin isotypes. See, e.g., FitzGerald et al., Protein Eng. 10(10):1221-1225, 1997. Another approach is to engineer recombinant fusion proteins linking two or more different single-chain antibody or antibody fragment segments with the needed dual specificities. See, e.g., Coloma et al., *Nature Biotech.* 15:159-163, 1997. A variety of bi-specific fusion proteins can be produced using molecular engineering. In one form, the bi-specific fusion protein is monovalent, consisting of, for example, a scFv with a single binding site for one antigen and a Fab fragment with a single binding site for a second antigen. In another form, the bi-specific fusion protein is divalent, consisting of, for example, an IgG with two binding sites for one antigen and two scFv with two binding sites for a second antigen.

Functional bi-specific single-chain antibodies (bscAb), also called diabodies, can be produced in mammalian cells using recombinant methods. See, e.g., Mack et al., *Proc. Natl. Acad. Sci.*, 92: 7021-7025, 1995. For example, bscAb are produced by joining two single-chain Fv fragments via a glycine-serine linker using recombinant methods. The V light-chain ($V_L$) and V heavy-chain ($V_H$) domains of two antibodies of interest are isolated using standard PCR methods. The $V_L$ and $V_H$ cDNA's obtained from each hybridoma are then joined to form a single-chain fragment in a two-step fusion PCR. The first PCR step introduces the $(Gly_4\text{-}Ser_1)_3$ linker, and the second step joins the $V_L$ and $V_H$ amplicons. Each single chain molecule is then cloned into a bacterial expression vector. Following amplification, one of the single-chain molecules is excised and sub-cloned into the other vector, containing the second single-chain molecule of interest. The resulting bscAb fragment is subcloned into an eukaryotic expression vector. Functional protein expression can be obtained by transfecting the vector into chinese hamster ovary cells. Bi-specific fusion proteins are prepared in a similar manner. Bi-specific single-chain antibodies and bi-specific fusion proteins are included within the scope of the present invention.

Bi-specific fusion proteins linking two or more different single-chain antibodies or antibody fragments are produced in similar manner.

Recombinant methods can be used to produce a variety of fusion proteins. For example a fusion protein comprising a Fab fragment derived from a humanized monoclonal anti-CEA antibody and a scFv derived from a murine anti-diDTPA can be produced. A flexible linker, such as GGGS connects the scFv to the constant region of the heavy chain of the anti-CEA antibody. Alternatively, the scFv can be connected to the constant region of the light chain of hMN-14. Appropriate linker sequences necessary for the in-frame connection of the heavy chain Fd to the scFv are introduced into the $V_L$ and $V_K$ domains through PCR reactions. The DNA fragment encoding the scFv is then ligated into a staging vector containing a DNA sequence encoding the $C_H1$ domain. The resulting scFv-$C_H1$ construct is excised and ligated into a vector containing a DNA sequence encoding the $V_H$ region of an anti-CEA antibody. The resulting vector can be used to transfect mammalian cells for the expression of the bi-specific fusion protein.

Large quantities of bscAb and fusion proteins can be produced using *Escherichia coli* expression systems. See, e.g., Zhenping et al., *Biotechnology*, 14: 192-196, 1996. A functional bscAb can be produced by the coexpression in *E. coli* of two "cross-over" scFv fragments in which the $V_L$ and $V_H$ domains for the two fragments are present on different polypeptide chains. The V light-chain ($V_L$) and V heavy-chain ($V_H$) domains of two antibodies of interest are isolated using standard PCR methods. The cDNA's are then ligated into a bacterial expression vector such that C-terminus of the $V_L$ domain of the first antibody of interest is ligated via a linker to the N-terminus of the $V_H$ domain of the second antibody. Similarly, the C-terminus of the $V_L$ domain of the second antibody of interest is ligated via a linker to the N-terminus of the $V_H$ domain of the first antibody. The resulting dicistronic operon is placed under transcriptional control of a strong promoter, e.g., the *E. coli* alkaline phosphatase promoter which is inducible by phosphate starvation. Alternatively, single-chain fusion constructs have successfully been expressed in *E. coli* using the lac promoter and a medium consisting of 2% glycine and 1% Triton X-100. See, e.g., Yang et al., *Appl. Environ. Microbiol.*, 64: 2869-2874, 1998. An *E. coli*, heat-stable, enterotoxin II signal sequence is used to direct the peptides to the periplasmic space. After secretion, the two peptide chains associate to form a non-covalent heterodimer which possesses both antigen binding specificities. The bscAb is purified using standard procedures known in the art, e.g., Staphylococcal protein A chromatography.

Functional bscAb and fusion proteins also can be produced in the milk of transgenic livestock. See, e.g., Colman, A., Biochem. Soc. Symp., 63: 141-147, 1998; U.S. Pat. No. 5,827, 690. The bscAb fragment, obtained as described above, is cloned into an expression vector containing a promoter sequence that is preferentially expressed in mammary epithelial cells. Examples include, but are not limited to, promoters from rabbit, cow and sheep casein genes, the cow α-lactoglobulin gene, the sheep β-lactoglobulin gene and the mouse whey acid protein gene. Preferably, the inserted bscAb is flanked on its 3' side by cognate genomic sequences from a mammary-specific gene. This provides a polyadenylation site and transcript-stabilizing sequences. The expression cassette is then injected into the pronuclei of fertilized, mammalian eggs, which are then implanted into the uterus of a recipient female and allowed to gestate. After birth, the progeny are screened for the presence of the introduced DNA by Southern analysis. Milk from transgenic females is analyzed for the presence and functionality of the bscAb using standard immunological methods known in the art. The bscAb can be purified from the milk using standard methods known in the art. Transgenic production of bscAb in milk provides an efficient method for obtaining large quantities of bscAb.

Functional bscAb and fusion proteins also can be produced in transgenic plants. See, e.g., Fiedler et al., *Biotech.*, 13: 1090-1093, 1995; Fiedler et al., *Immunotechnology*, 3: 205-216, 1997. Such production offers several advantages including low cost, large scale output and stable, long term storage. The bscAb fragment, obtained as described above, is cloned into an expression vector containing a promoter sequence and encoding a signal peptide sequence, to direct the protein to the endoplasmic reticulum. A variety of promoters can be utilized, allowing the practitioner to direct the expression product to particular locations within the plant. For example, ubiquitous expression in tobacco plants can be achieved by using the strong cauliflower mosaic virus 35S promoter, while organ specific expression is achieved via the seed specific legumin B4 promoter. The expression cassette is transformed according to standard methods known in the art. Transformation is verified by Southern analysis. Transgenic plants are analyzed for the presence and functionality of the bscAb using standard immunological methods known in the art. The bscAb can be purified from the plant tissues using standard methods known in the art.

Additionally, transgenic plants facilitate long term storage of bscAb and fusion proteins. Functionally active scFv proteins have been extracted from tobacco leaves after a week of storage at room temperature. Similarly, transgenic tobacco seeds stored for 1 year at room temperature show no loss of scFv protein or its antigen binding activity.

Functional bscAb and fusion proteins also can be produced in insect cells. See, e.g., Mahiouz et al., *J. Immunol. Methods*, 212: 149-160 (1998). Insect-based expression systems provide a means of producing large quantities of homogenous and properly folded bscAb. The baculovirus is a widely used expression vector for insect cells and has been successfully applied to recombinant antibody molecules. See, e.g., Miller, L. K., *Ann. Rev. Microbiol.*, 42: 177 (1988); Bei et al., *J. Immunol. Methods*, 186: 245 (1995). Alternatively, an inducible expression system can be utilized by generating a stable insect cell line containing the bscAb construct under the transcriptional control of an inducible promoter. See, e.g., Mahiouz et al., *J. Immunol. Methods*, 212: 149-160 (1998). The bscAb fragment, obtained as described above, is cloned into an expression vector containing the *Drosphila* metallothionein promoter and the human HLA-A2 leader sequence. The construct is then transfected into *D. melanogaster* SC-2 cells. Expression is induced by exposing the cells to elevated amounts of copper, zinc or cadmium. The presence and functionality of the bscAb is determined using standard immunological methods known in the art. Purified bscAb is obtained using standard methods known in the art.

Preferred bispecific antibodies of the instant invention are those which incorporate the Fv of MAb Mu-9 and the Fv of MAb 679 or the Fv of MAb MN-14 and the Fv of MAb 679, and their human, chimerized or humanized counterparts. The MN-14, as well as its chimerized and humanized counterparts, are disclosed in U.S. Pat. No. 5,874,540. Also preferred are bispecific antibodies which incorporate one or more of the CDRs of Mu-9 or 679. The antibody can also be a fusion protein or a bispecific antibody that incorporates a Class-III anti-CEA antibody and the Fv of 679. Class-III antibodies, including Class-III anti-CEA are discussed in detail in U.S. Pat. No. 4,818,709. 679 is described in US20030113333A and US20020006379.

VII. Other Applications

The present invention encompasses the use of the bsAb and a therapeutic or diagnostic agent associated with the targetable construct discussed above in intraoperative, intravascular, and endoscopic tumor and lesion detection, biopsy and therapy as described in U.S. Pat. No. 6,096,289.

The antibodies and antibody fragments of the present invention can be employed not only for therapeutic or imaging purposes, but also as aids in performing research in vitro. For example, the bsAbs of the present invention can be used in vitro to ascertain if a targetable construct can form a stable complex with one or more bsAbs. Such an assay would aid the skilled artisan in identifying targetable constructs which form stable complexes with bsAbs. This would, in turn, allow the skilled artisan to identify targetable constructs which are likely to be superior as therapeutic and/or imaging agents.

The assay is advantageously performed by combining the targetable construct in question with at least two molar equivalents of a bsAb. Following incubation, the mixture is analyzed by size-exclusion HPLC to determine whether or not the construct has bound to the bsAb. Alternatively, the assay is performed using standard combinatorial methods wherein solutions of various bsAbs are deposited in a standard 96-well plate. To each well, is added solutions of targetable construct(s). Following incubation and analysis, one can readily determine which construct(s) bind(s) best to which bsAb(s).

It should be understood that the order of addition of the bsAb to the targetable construct is not crucial; that is, the bsAb may be added to the construct and vice versa. Likewise, neither the bsAb nor the construct needs to be in solution; that is, they may be added either in solution or neat, whichever is most convenient. Lastly, the method of analysis for binding is not crucial as long as binding is established. Thus, one may analyze for binding using standard analytical methods including, but not limited to, FABMS, high-field NMR or other appropriate method in conjunction with, or in place of, size-exclusion HPLC.

The present invention is further illustrated by, though in no way limited to, the following examples.

EXAMPLES

IMP 281 Labeling

The following peptide was labeled with $^{111}$In: (MH+: 1361)

DOTA-D-Ala-D-Lys(HSG)-D-Glu-D-Lys(HSG)-NH$_2$

In addition, the peptide was tested, after labeling, for stability in human serum (previously frozen) over a period of 20 hrs at 37° C. The study showed that the peptide remained stable. IMP 281 was also tested for binding with the humanized antibody, m679×hMN14. The In-111 labeled peptide was analyzed both on the reverse phase and the size exclusion HPLC systems.

Synthesis of IMP 281

The peptide was synthesized (NB Ref. CN 2-34) by solid phase peptide synthesis on Rink Amide resin (2.0159 g, 0.7 mmol/g) using standard Fmoc synthesis methodology. The following amino acids (6 equivalents per coupling) were added in the order shown; Fmoc-D-Lys(Aloc)-OH, Fmoc-D-Glu(OBut)-OH, Fmoc-D-Lys(Aloc)-OH, Fmoc-D-Ala-OH and DOTA-tris(t-Butyl) ester. Each amino acid was double coupled with two hour couplings first using diisopropylcarbodiimide followed by a coupling using O-Benzotriazole-N,N,N',N'-tetramethyl-uronium-hexafluoro-phosphate (HBTU) as the activating agents. The Aloc side chains were then removed with the Pd catalyst in the usual way and the trityl-HSG-OH was double coupled to the lysine side chains. The peptide was cleaved from the resin with TFA, precipitated in ether, and purified by HPLC to obtain the desired peptide. Successful synthesis was confirmed by ESMS analysis, MH+: 1361. The total yield of desired product was 298.8 mg in 6 fractions. Out of these 6 fractions, 4 contain pure peptide amounting to 201.3 mg while the remaining two fractions contain a slight impurity with a total mass of 97.5 mg.

IMP 281 Solution

The peptide (3.5 mg) was combined with 1169 μL of 0.5 M NH$_4$OAc Buffer (pH 3.98, Ref. BM10-91) to reach a final concentration of $2.2 \times 10^{-3}$ M.

Figure 2:
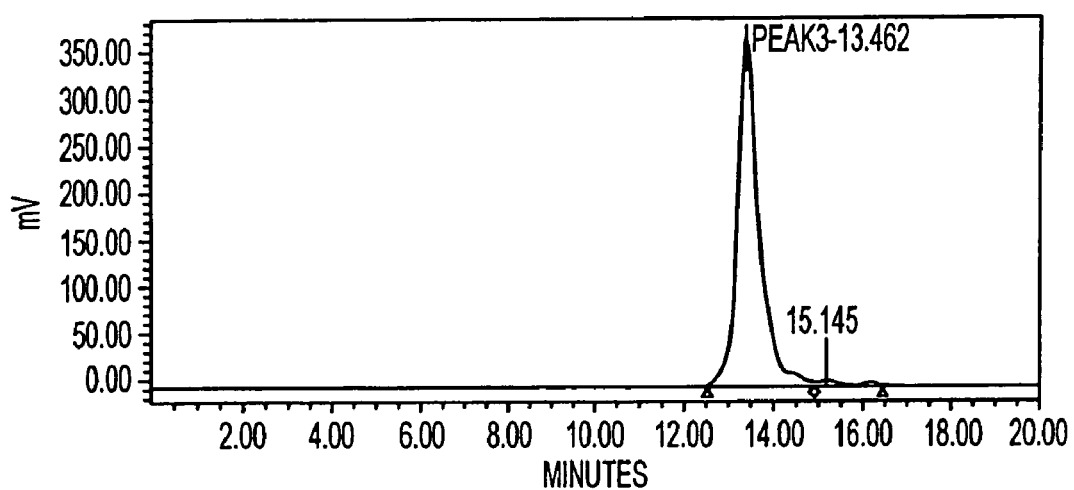
FIG. 2 shows a size-exclusion HPLC (SE-HPLC)trace of labeled IMP 281
Figure 3A:
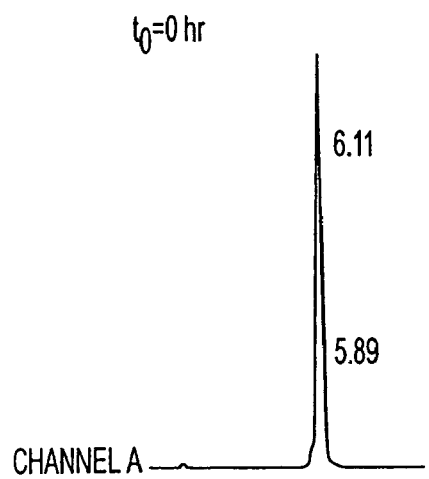
FIG. 3 shows RP-HPLC traces demonstrating the stability of IMP 281 in human serum.
Figure 3B:
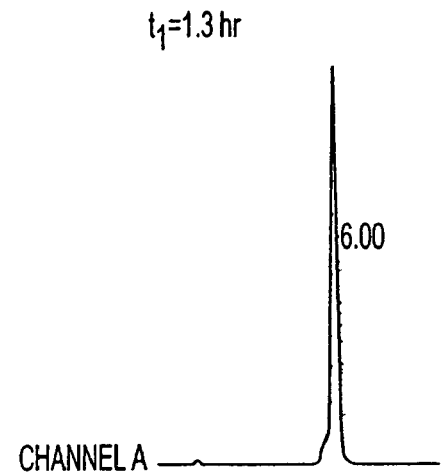
Figure 3C:
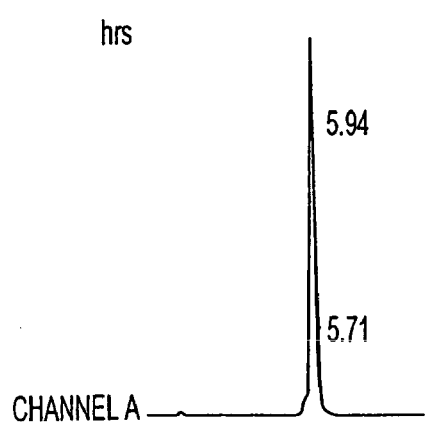
Figure 3D:
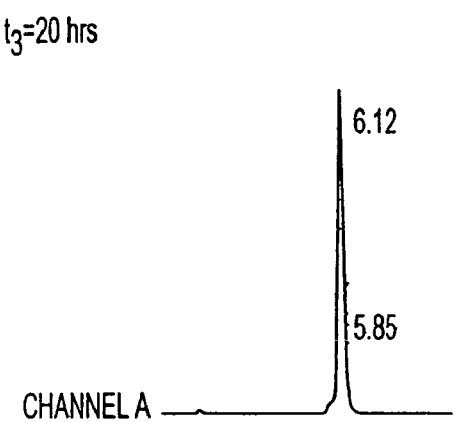

IMP 281 Labeling (FIGS. 1 and 2)

$^{111}$InCl$_3$ (6.3 μL) was added to 2.5 μL of the IMP 281 solution and 150 μL of 0.5 M NH$_4$OAc Buffer (pH 3.98, Ref. BM10-91) in a screw top plastic vial. This vial was placed in a lead pig which was submerged in a boiling water bath, for 15 minutes. The plastic vial was removed and allowed to return to r.t. The labeled peptide was subsequently analyzed by reverse phase HPLC and size exclusion HPLC. The chromatograms (FIGS. 1 & 2) showed that the peptide labeled well. The peptide concentration of this solution was $3.463 \times 10^{-4}$ M.

$^{111}$In IMP 281 in Human Serum (FIG. 3)

A (1:9) mixture of the labeled peptide and human serum (previously frozen) was made and incubated at 37° C. The $^{111}$In IMP 281 solution (70 μL) and 630 μL of human serum were combined and vortexed. This was maintained at constant temperature for 20 hrs. with injections into the reverse phase HPLC at t0=0 hrs, t1=1.3 hrs, t2=2.5 hrs, and t3=20 hrs. The labeled peptide appears to not have undergone any change as a result of being mixed in human serum. This mixture had a peptide concentration of $3.463 \times 10^{-5}$ M.

Figure 4:
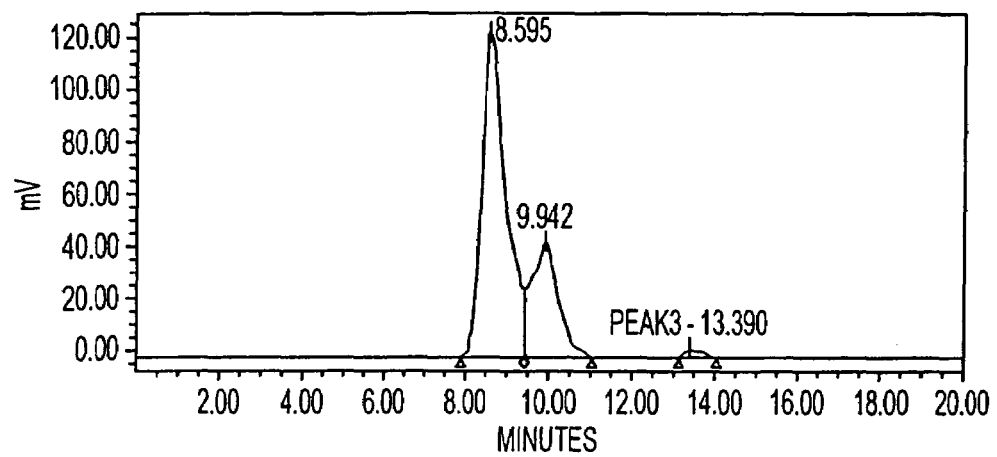
FIG. 4 shows an SE-HPLC of IMP 281 binding to m679×hMN14.

$^{111}$In IMP 281 & Antibody Binding (FIG. 4)

The labeled peptide (0.5 μL) mixture was combined with 4.33 μL of m679×hMN14 antibody (antibody/peptide ratio of 10:1) and 995 μL of 0.9% Saline. The solution was vortexed and analyzed by size exclusion HPLC. The chromatograms indicate that there is mostly bis-antibody bound but some mono-antibody bound peptide.

Figure 5:
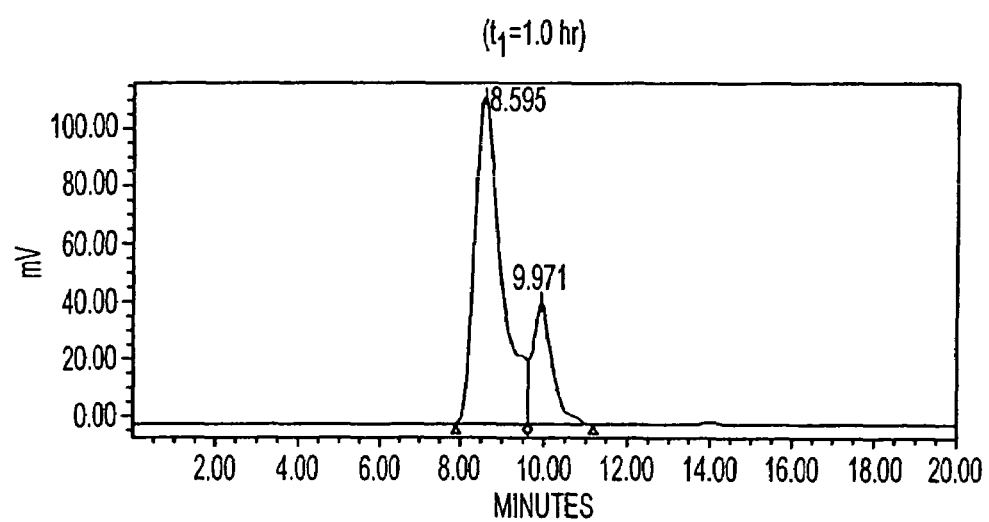
FIGS. 5 and 6 show SE-HPLC traces of IMP 281 bound to m679×hMN14 after incubation in human serum.
Figure 6:
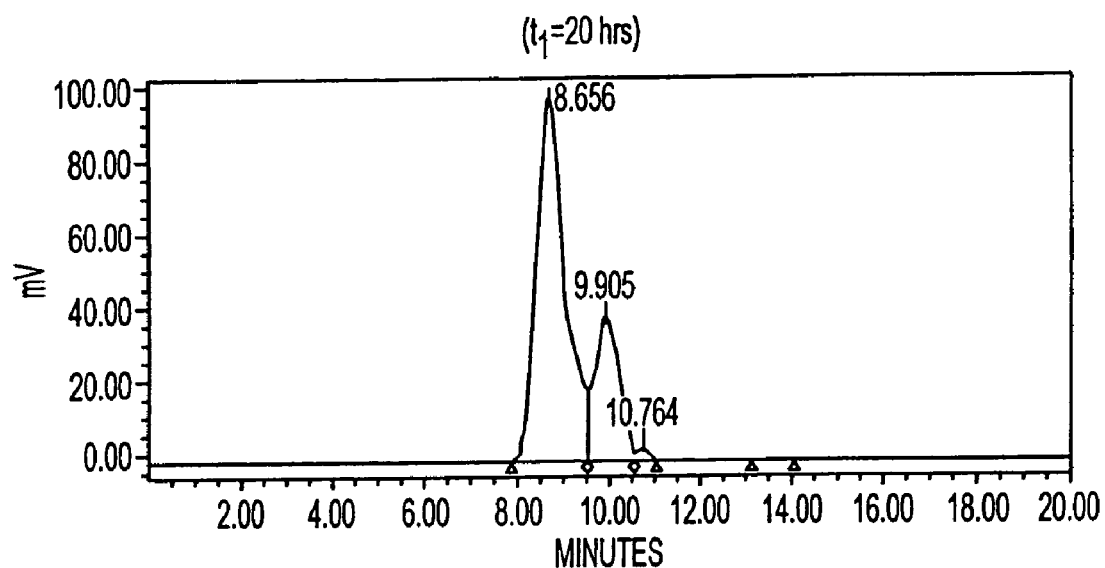

$^{111}$In IMP 281 w/Antibody & Human Serum (FIGS. 5 & 6)

$^{111}$In-IMP 281 in human serum (5.0 μL) was added to 4.33 μL of m679×hMN14 antibody (antibody/peptide ratio of 10:1) and 990 μL 0.9% Saline. The mixture was vortexed and analyzed by size exclusion HPLC at two time points (1 hr and 20 hrs). The results look similar to those of the peptide with the antibody alone.

IMP 284 Labeling

The following peptide was labeled with $^{111}$In: (MH+: 1471)

DOTA-D-Phe-D-Lys(HSG)-D-Tyr-D-Lys(HSG)-NH$_2$

In addition, the peptide was tested, after labeling, for stability in human serum over a period of 21 hrs. in human serum and 19 hrs. in mouse serum. The study showed that the peptide remained stable. IMP 284 was also tested for binding with the humanized antibody, m679×hMN 14. Reverse phase and the size exclusion HPLC systems were utilized in this study to analyze the labeling, antibody binding, and serum stability.

Synthesis of IMP 284

The peptide was synthesized by solid phase peptide synthesis on Rink Amide resin (1.0 g, 0.6 mmol/g) using standard Fmoc synthesis methodology. The following amino acids (6 equivalents per coupling) were added in the order shown; Fmoc-D-Lys(Aloc)-OH, Fmoc-D-Tyr(But)-OH, Fmoc-D-Lys(Aloc)-OH, Fmoc-D-Phe-OH and DOTA-tris(t-Butyl) ester. Each amino acid was coupled overnight using diisopropylcarbodiimide (DIC) as the activating agent. The Aloc side chains were then removed with the Pd catalyst in the usual way and the trityl-HSG-OH (7 Eq) was coupled to the lysine side chains with DIC (7 Eq) in the presence of DIEA (14 Eq). The peptide was cleaved from the resin with TFA, precipitated in ether, and purified by HPLC to obtain the desired peptide. Successful synthesis was confirmed by ESMS analysis, MH+: 1471. The total yield of desired product was 248.1 mg in 3 fractions.

IMP 284 Solution

The peptide (3.7 mg) was combined with 1143 μL of 0.5 M NH$_4$OAc Buffer (pH 3.98, Ref. BM10-91) to reach a final concentration of $2.2 \times 10^{-3}$ M.

Figure 7:
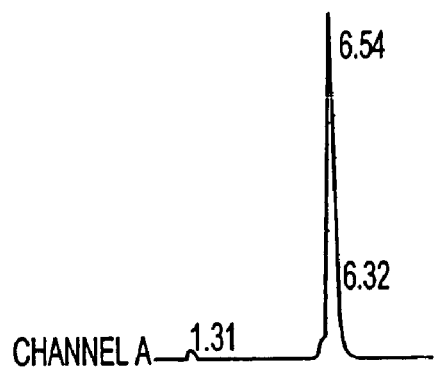
FIGS. 7 and 8 show RP- and SE-HPLC traces of labeled IMP 284.
Figure 8:
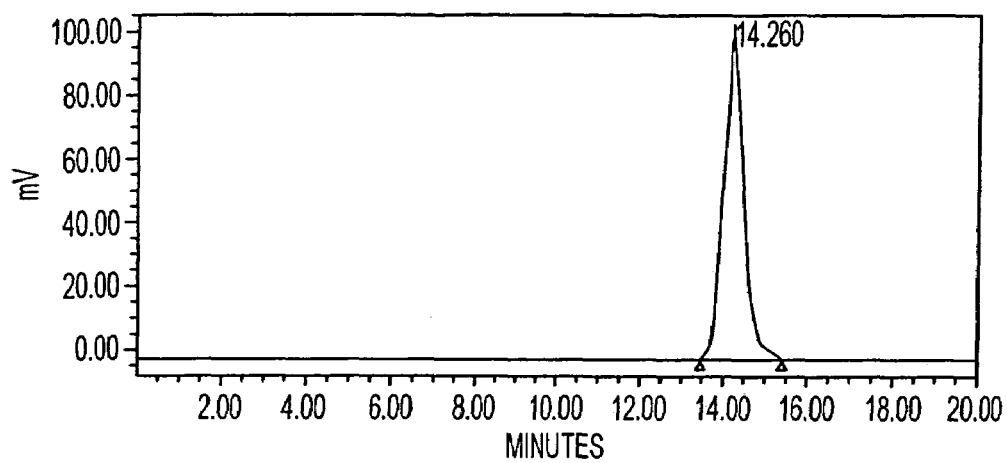

IMP 284 Labeling (FIGS. 7 & 8)

$^{111}$InCl$_3$ (7.9 μL) was added to 2.5 μL of the IMP 284 solution and 150 μL of 0.5 M NH$_4$OAc Buffer (pH 3.98, Ref. BM10-91) in a "screw top" plastic vial. This vial was placed in a led pig which was, it self, submerged in a boiling water bath, for 15 minutes. The plastic vial was removed and allowed to return to r.t. and was subsequently analyzed by reverse phase HPLC. The chromatogram showed that the peptide labeled well. The peptide concentration of this solution was $3.429 \times 10^{-5}$ M.

Figure 9:
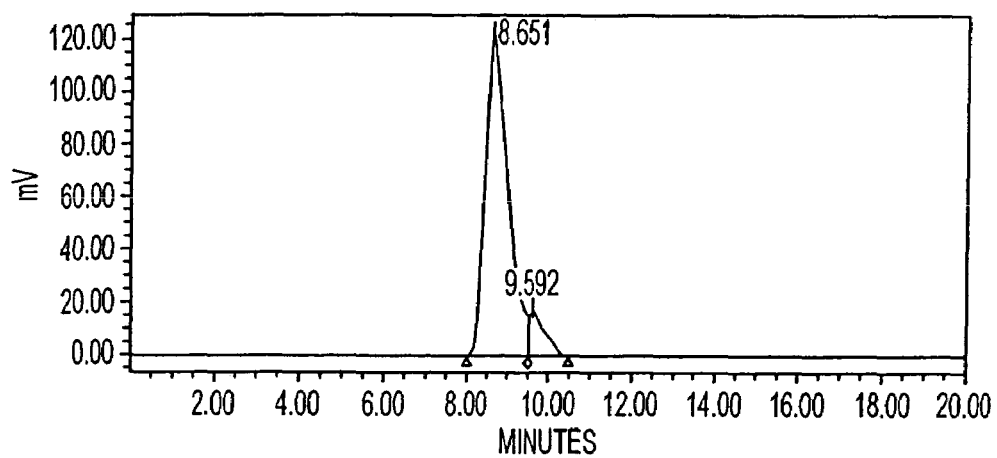
FIG. 9 shows an SE-HPLC of IMP 284 binding to m679×hMN14

$^{111}$In IMP 284 & Antibody Binding (FIG. 9)

The labeled peptide (0.5 μL) mixture was combined with 3.1 μL of m679×hMN14 antibody (antibody/peptide ratio of 19.7:1) and 1000 μL of 0.9% Saline. The solution was vortexed and analyzed by HPLC. The chromatograms indicate that there is mostly dibound and a small amount of what may be monobound peptide.

Figure 10A:
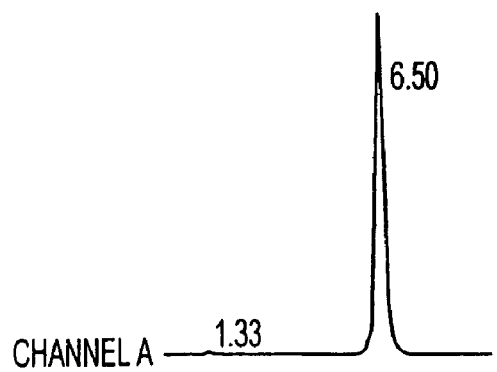
FIG. 10 shows RP-HPLC traces demonstrating the stability of IMP 284 in human serum.
Figure 10B:
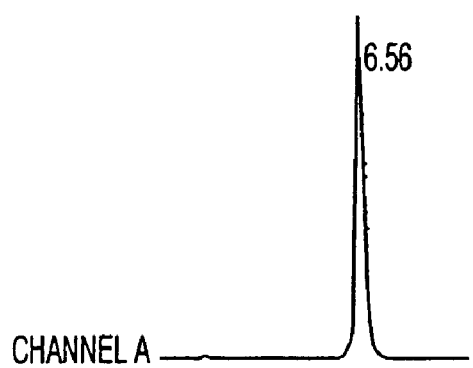
Figure 10C:
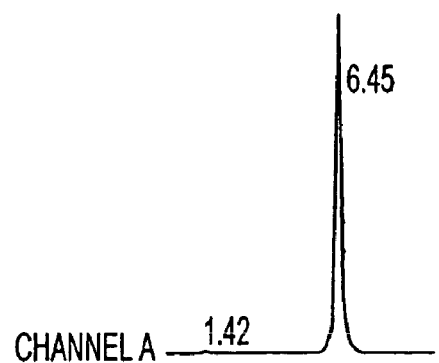

$^{111}$In IMP 284 in Human Serum (FIG. 10)

A mixture of the labeled peptide and human serum was made and incubated at 37° C. for 19.5 hrs. The human serum was freshly drawn, spun, and filtered through a Millex®-GV 0.22 μm Filter Unit. The Indium-labeled peptide solution (50 μL) and 450 μL of human serum were combined and vortexed. While incubating, injections were made into the reverse phase HPLC at t0=0 hrs, t1=2.0 hrs, and t2=19.5 hrs. The labeled peptide appears to not have undergone any change as a result of being mixed in human serum. This mixture had a peptide concentration of $3.429 \times 10^{-6}$ M. after dilution in human serum.

Figures 13A, 13B:
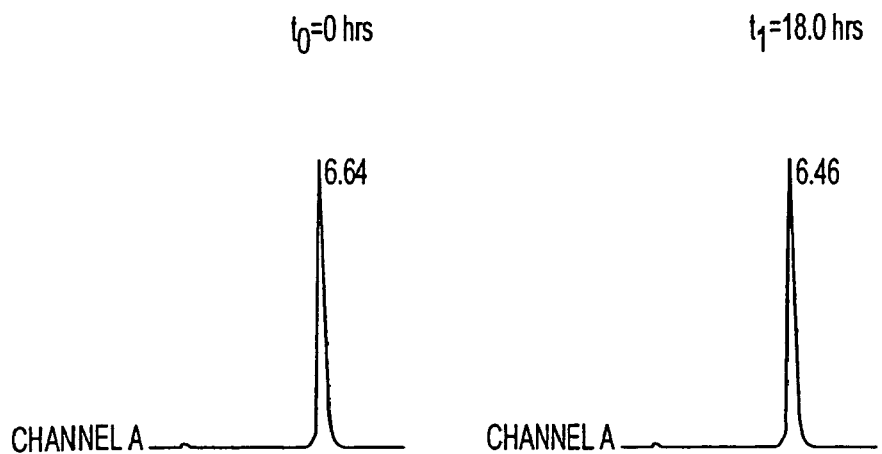
FIG. 13 shows stability of labeled IMP 284 in mouse serum.

$^{111}$In IMP 284 in Mouse Serum (FIG. 13)

A mixture of the labeled peptide and mouse serum was made and incubated at 37° C. The mouse serum was fresh nude mouse serum obtained from (GSCC on the same day).

The Indium-labeled peptide solution (50 µL) and 450 µL of the mouse serum were combined and vortexed. This was incubated at 37° C. for 18.0 hrs. Injections were made into the reverse phase HPLC at t0=0 hrs and t1=18.0 hrs. The labeled peptide appears to not have undergone any change as a result of being mixed in mouse serum. This mixture had a peptide concentration of $3.429 \times 10^{-6}$ M after dilution in mouse serum.

Figure 11:
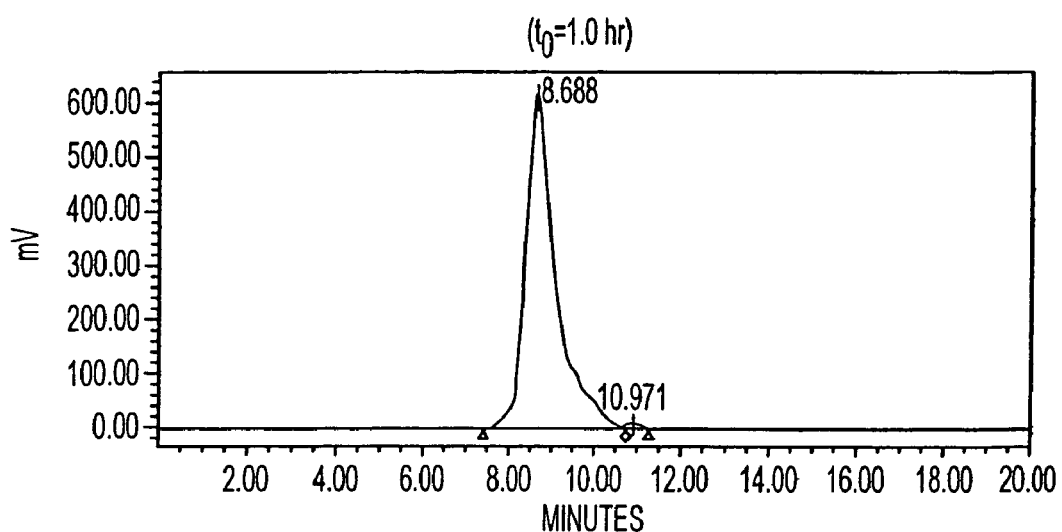
FIGS. 11 and 12 show SE-HPLC traces of IMP 284 bound to m679×hMN14 after incubation in human serum.
Figure 12:
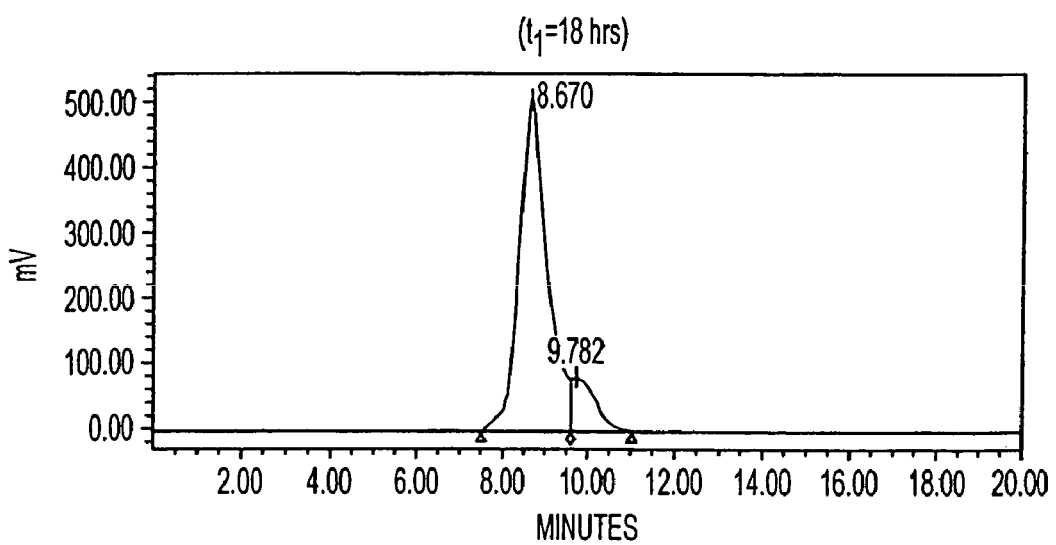

$^{111}$In IMP 284 w/Antibody & Human Serum (FIGS. 11 and 12)

$^{111}$In-IMP 284 in human serum (1.0 µL) was added to 0.7 µL of m679×hMN14 antibody (antibody/peptide ratio of 22.3:1) and 60 µL 0.9% Saline. The mixture was vortexed and analyzed by size exclusion HPLC. The same procedure was repeated 18 hrs. later. The results of both radiometric chromatograms look similar to those of the peptide with the antibody alone.

Figure 14:
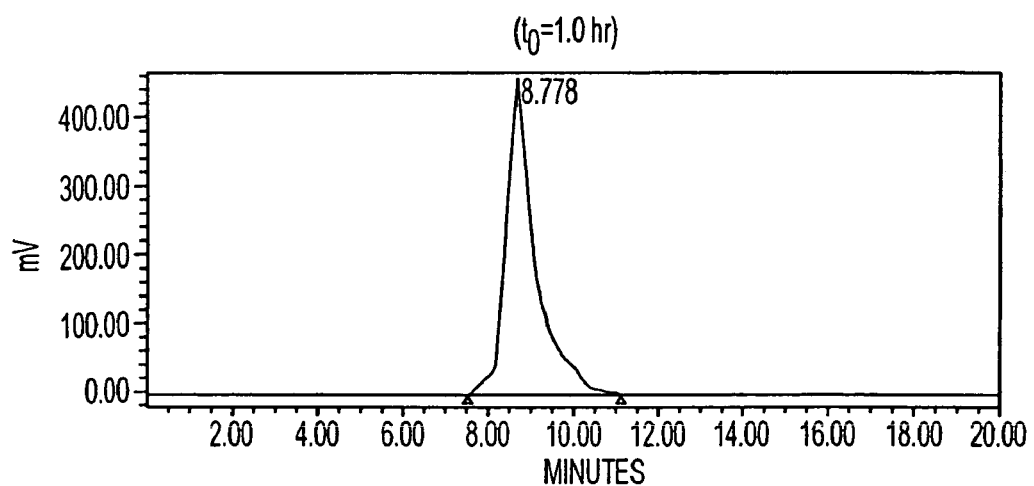
FIGS. 14 and 15 show stability of labeled IMP 284 bound to m679×hMN14 in human serum.
Figure 15:
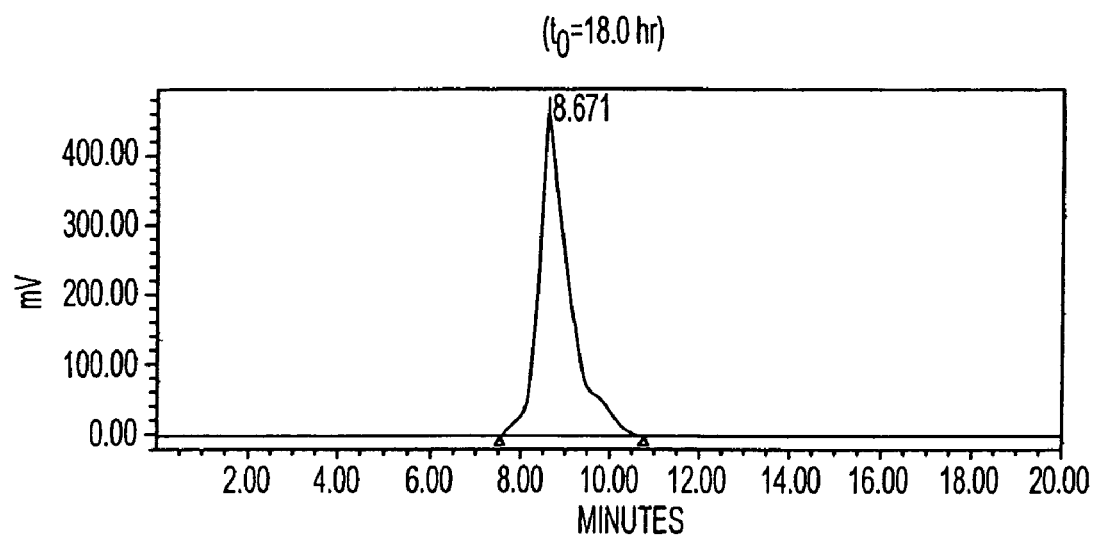

$^{111}$In IMP 284 w/Antibody & Human Serum (FIGS. 14 and 15)

$^{111}$In-IMP 284 in human serum (1.0 µL) was added to 0.7 µL of m679×hMN14 antibody (antibody/peptide ratio of 22.3:1) and 60 µL 0.9% Saline. The mixture was vortexed and analyzed by size exclusion HPLC. The same procedure was repeated 16 hrs. later. The results of both radiometric chromatograms look similar to those of the peptide with the antibody alone.

Peptide Labeling

The following peptides were labeled with 111In:

IMP281

DOTA-D-Ala-D-Lys(HSG)-D-Glu-D-Lys(HSG)-NH$_2$ (MH+: 1361)

IMP284

DOTA-D-Phe-D-Lys(HSG)-D-Tyr-D-Lys(HSG)-NH$_2$ (MH+: 1471)

In addition, the peptides were tested, after labeling, for stability in human serum over a period of 21 hrs. The study showed that both peptides remained stable. IMP281 & IMP284 were also tested for binding with the humanized antibody, m679×hMN14 (100,000 g mol−1, 10.9 mg mL−1). Studies were analyzed both on reverse phase and size exclusion HPLC systems.

IMP 281

This peptide was previously synthesized and due to impurities discovered after the initial purification, was repurified twice more using different mobile phases, columns, flow-rates, and gradients. The material used for the labeling study described in this report was ~97% pure (HPLC).

IMP 284

This peptide was previously synthesized and due to impurities discovered after the initial purification, was repurified twice more using different mobile phases, columns, flow-rates, and gradients. The material used for the labeling study described in this report was ~97% pure (HPLC).

IMP 281 Stock Solution

The peptide (3.9 mg) was combined with 1303 µL of 0.5 M NH$_4$OAc Buffer (pH 3.98) to reach a concentration of $2.2 \times 10^{-3}$ M.

IMP 284 Stock Solution

The peptide (1.5 mg) was combined with 464 µL 0.5M NH$_4$OAc Buffer (pH 3.98) to reach a concentration of $2.2 \times 10^{-3}$ M.

Figure 16:
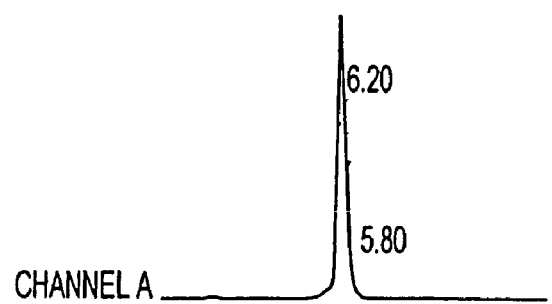
FIGS. 16 and 17 show RP- and SE-HPLC traces of labeled IMP 281.
Figure 17:
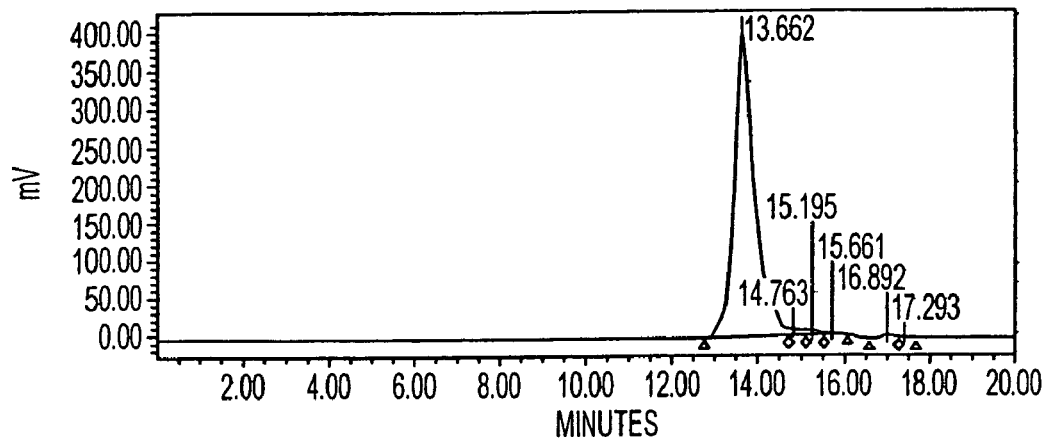

IMP 281 Labeling (FIGS. 16 & 17)

$^{111}$InCl$_3$ (6.2 µL) was added to 2.5 µL of the IMP 281 stock solution and 150 µL of 0.5 M NH$_4$OAc Buffer (pH 3.98) in a screw top plastic vial. This vial was placed in a lead pig which was submerged in a boiling water bath for 32 minutes. The plastic vial was removed and allowed to return to RT and was subsequently analyzed by reverse phase HPLC. Reverse Phase HPLC shows that the peptide labeled well with only a trace amount of unbound Indium. The peptide concentration of this solution was $3.466 \times 10^{-5}$ M.

Figure 18:
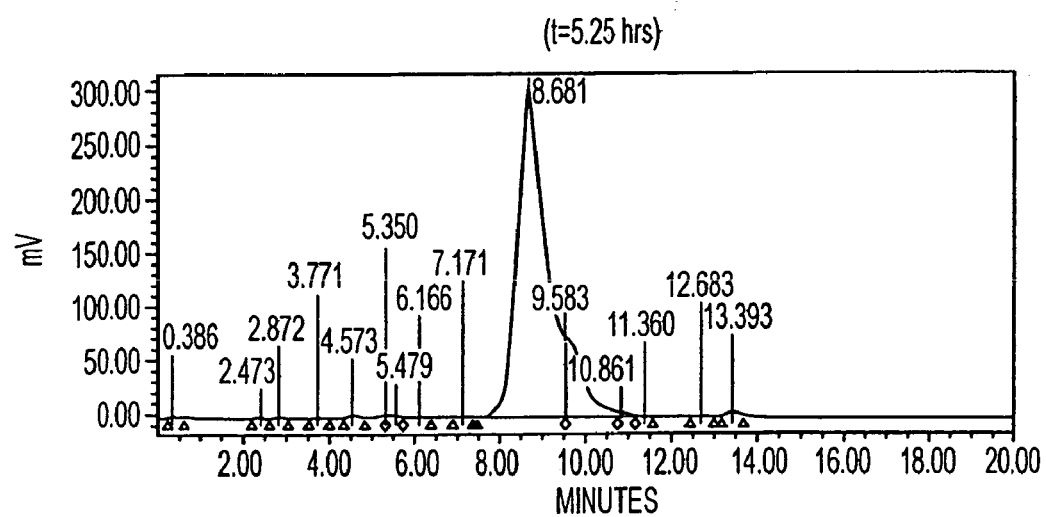
FIG. 18 shows an SE-HPLC trace of labeled IMP 281 bound to m679×hMN14.

$^{111}$In IMP 281 & Antibody Binding (FIG. 18)

The labeled peptide (1.0 µL) mixture was combined with 3.2 µL of m679×hMN14 antibody (antibody/peptide ratio of 10:1) and 200 µL of 0.9% Saline. The solution was vortexed and analyzed by HPLC. The chromatograms indicate that there is mostly dibound but some monobound peptide as well.

Figure 19:
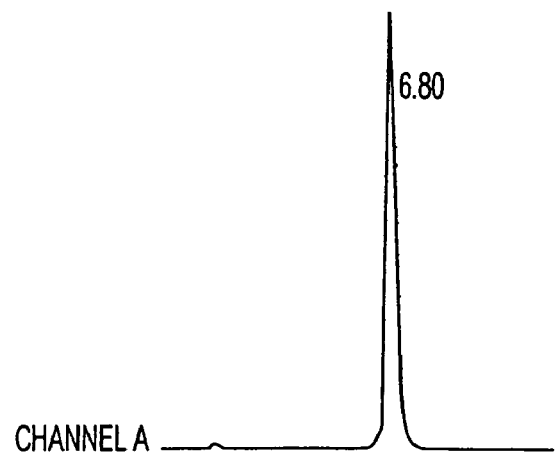
FIGS. 19 and 20 show RP- and SE-HPLC traces of labeled IMP 284.
Figure 20:
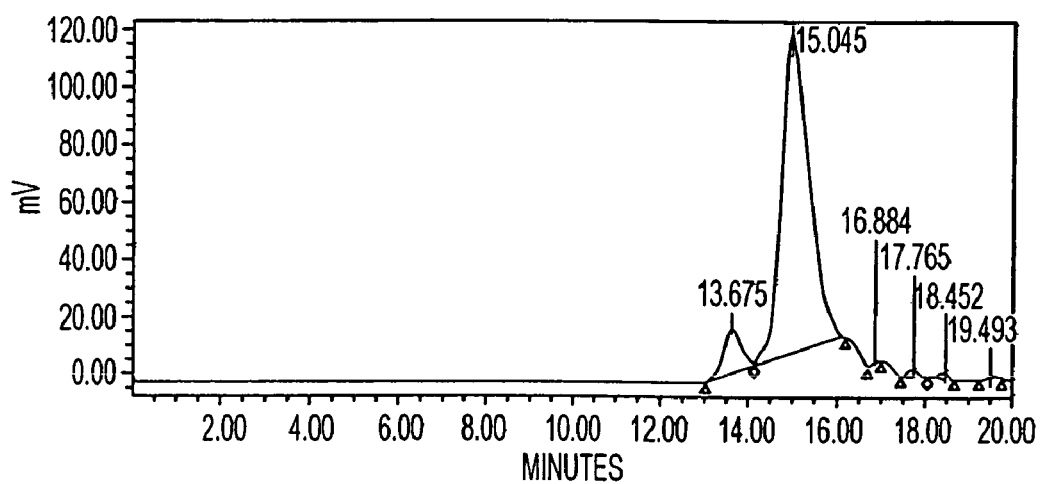

IMP 284 Labeling (FIGS. 19 and 20)

$^{111}$InCl$_3$ (6.2 µL) was added to 2.5 µL of the IMP 284 stock solution and 150 µL of 0.5 M NH$_4$OAc Buffer (pH 3.98) in a screw top plastic vial. This vial was placed in a lead pig which was submerged in a boiling water bath, for 32 minutes. The plastic vial was removed and allowed to return to RT and was subsequently analyzed by reverse phase HPLC. Reverse Phase HPLC shows that the peptide labeled well with only a trace amount of unbound Indium. The peptide concentration of this solution was $3.466 \times 10^{-5}$ M.

Figure 21:
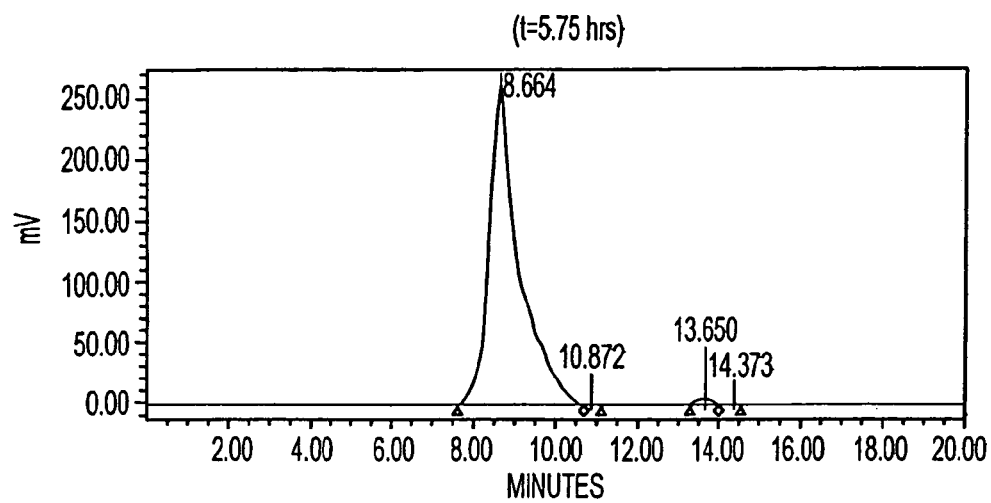
FIG. 21 shows an SE-HPLC trace of IMP 284 bound to m679×hMN14.

$^{111}$In IMP 284 & Antibody Binding (FIG. 21)

The labeled peptide (1.0 µL) mixture was combined with 3.2 µL of m679×hMN14 antibody (antibody/peptide ratio of 10:1) and 200 µL of 0.9% Saline. The solution was vortexed and analyzed by HPLC. The chromatograms indicate that there is mostly dibound but some monobound peptide as well.

Figure 22A:
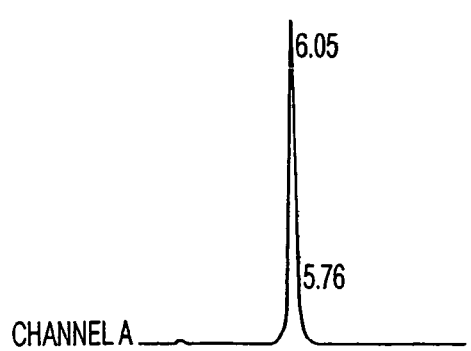
FIG. 22 shows stability of labeled IMP 281 in human serum.
Figure 22B:
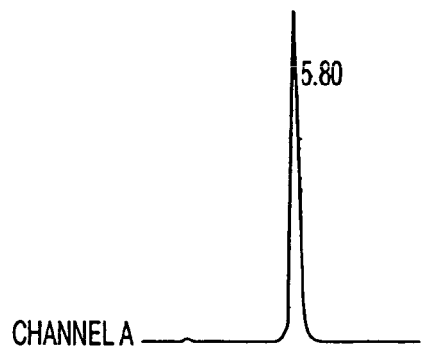

111In IMP 281 in Human Serum (FIG. 22)

A mixture of the labeled peptide and freshly drawn and filtered human serum was made and incubated at 37° C. The Indium-111 labeled peptide (50 µL) and 450 µL of human serum were combined and vortexed. This was maintained at constant temperature for 21 hrs with injections into the reverse phase HPLC at t0=2.25 hrs, t1=3.25 hrs, & t2=20.25 hrs. The labeled peptide appears to not have undergone any change as a result of being mixed in human serum. This mixture had a peptide concentration of $3.466 \times 10^{-6}$ M.

Figures 23A, 23B, 23C:
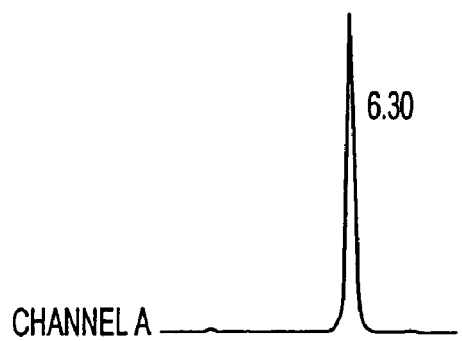
FIG. 23 shows stability of labeled IMP 284 in human serum.

$^{111}$In IMP 284 in Human Serum (FIG. 23)

A mixture of the labeled peptide and freshly drawn and filtered human serum was made and incubated at 37° C. The Indium-111 labeled peptide (50 µL) and 450 µL of human serum were combined and vortexed. This was maintained at constant temperature for 21 hrs with injections into the reverse phase HPLC at t0=2.5 hrs & t1=20.5 hrs. The labeled peptide appears to not have undergone any change as a result of being mixed in human serum. This mixture had a peptide concentration of $3.466 \times 10^{-6}$ M.

Figure 24:
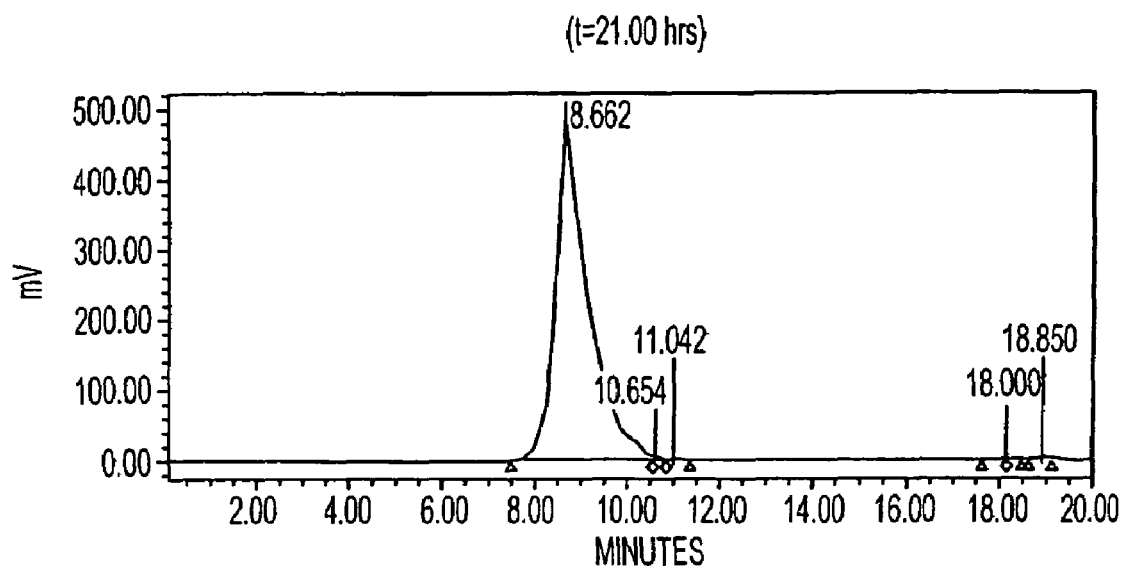
FIG. 24 shows stability of labeled IMP 281 bound to m679×hMN14 in human serum

$^{111}$In IMP 281 w/Antibody & Human Serum (FIG. 24)

$^{111}$In-IMP 281 in human serum (1.0 µL) was added to 0.64 µL of m679×hMN14 antibody (antibody/peptide ratio of 20:1) and 200 µL 0.9% Saline. The mixture was vortexed and analyzed by size exclusion HPLC. The results look similar to those of the peptide with the antibody alone.

Figure 25:
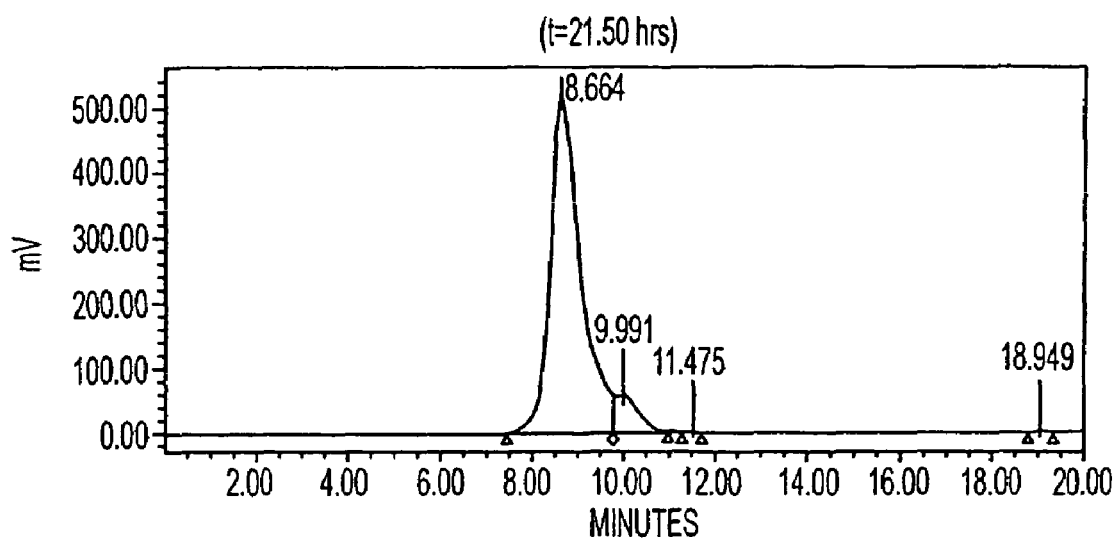
FIG. 25 shows stability of labeled IMP 284 bound to m679×hMN14 in human serum
Figure 26A:
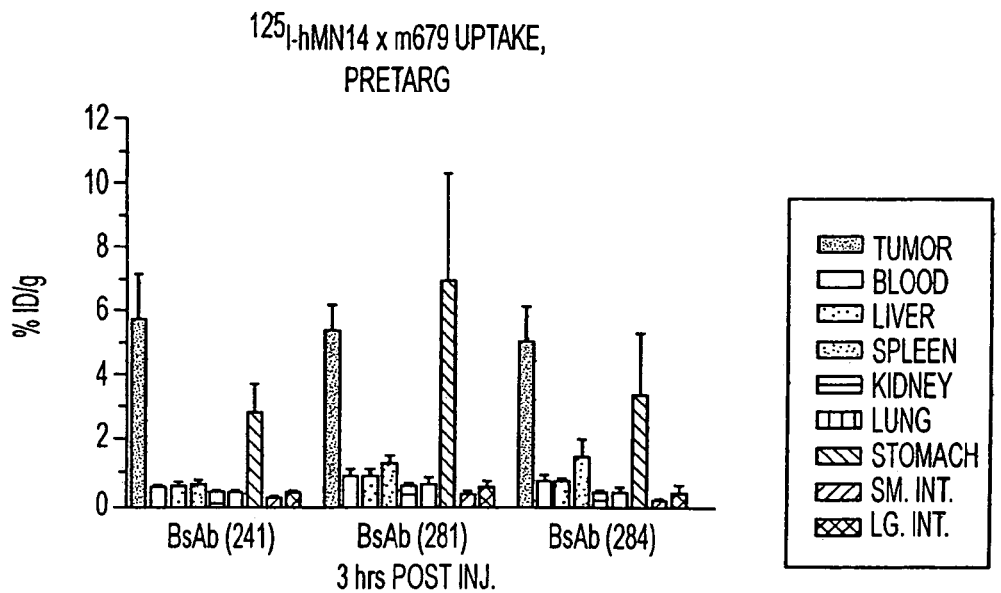
FIG. 26 shows tissue uptake of $^{125}$IhM14×m679 Fab'×Fab' in pretargeting at 3 and 24 h post peptide injection.
Figure 26B:
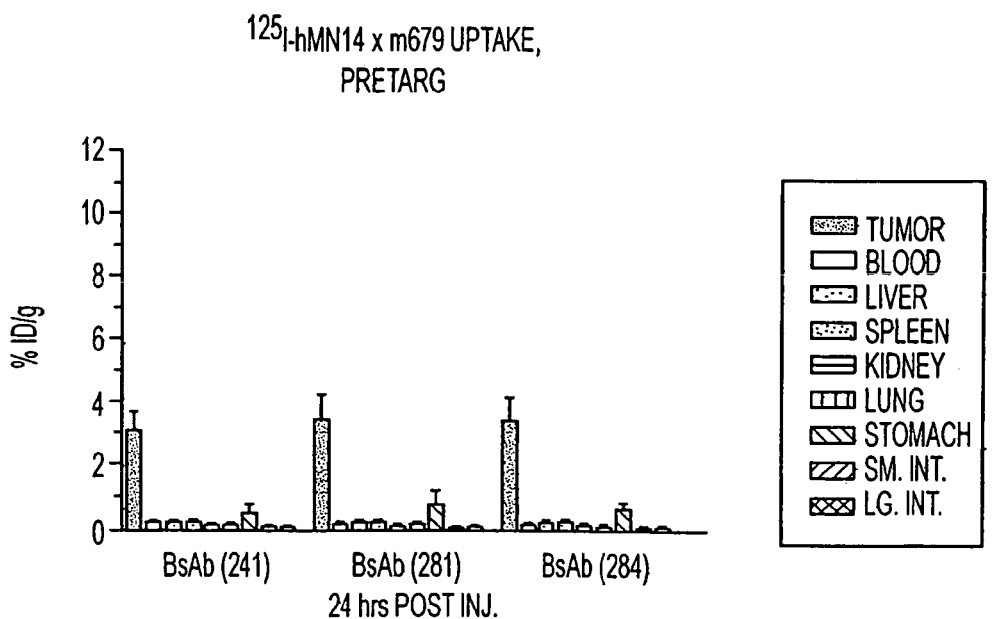

$^{111}$In IMP 284 w/Antibody & Human Serum (FIG. 25)

$^{111}$In-IMP 284 in human serum (1.0 µL) was added to 0.64 µL of m679×hMN14 antibody (antibody/peptide ratio of 20:1) and 200 ×L 0.9% Saline. The mixture was vortexed and analyzed by size exclusion HPLC. The results look similar to those of the peptide with the antibody alone.

The following peptide was synthesized and labeled with $^{111}$In: (IMP 277 MH+1419)

DOTA-D-Glu-D-Lys(HSG)-D-Glu-D-Lys(HSG)-NH$_2$

An all D-amino acid was used to improve the stability of the peptide in serum.

Synthesis:

The peptide was synthesized by solid phase peptide synthesis on Sieber Amide resin using the Fmoc procedure. The following amino acids were added in the order shown; Fmoc-D-Lys(Aloc)-OH, Fmoc-D-Glu(OBut)-OH, Fmoc-D-Lys(Aloc)-OH, Fmoc-D-Glu(OBut)-OH, DOTA-tris(tBu) ester.

Each amino acid was double coupled with two hour couplings first using diisopropylcarbodiimide followed by a coupling using O-Benzotriazole-N,N,N',N'-tetramethyl-uronium-hexafluoro-phosphate (HBTU) as the activating agents. The Aloc side chains were then remove with the Pd catalyst in the usual way and the trityl-HSG-OH was double coupled to the lysine side chains. The peptide was cleaved from the resin with TFA, precipitated in ether, and purified by HPLC to obtain the desired peptide.

Labeling Solution:

The peptide, 0.0015 g (1.06×10−6 mol) was dissolved in 480 µL 0.5 M NH$_4$OAc pH 3.98 for labeling.

Radiolabeling:

The peptide, 2.5 µL was mixed with 20 µL In-111 (2.78 mCi) and 60 µL 0.5 M NH$_4$OAc pH 3.98. The solution was heated in a boiling water bath for 15 min.

Another labeling was performed using the same conditions except a different reaction buffer was used 30 µL 0.5 M NH$_4$OAc pH 5.5 buffer.

Serum Stability:

Human Serum:

The In-111 IMP 277 (30 µL) was diluted in 540 µL of fresh human serum and placed in an incubator at 37° C. Aliquots were withdrawn at various time points and examined by reverse phase HPLC and by size exclusion HPLC.

Mouse Serum:

The In-111 IMP 277 (15 µL) was diluted in 150 µL of fresh mouse serum and placed in an incubator at 37° C. Aliquots were withdrawn at various time points and examined by reverse phase HPLC and by size exclusion HPLC.

Results:

The peptide labels well with In-111 but reverse phase HPLC shows that it contains an impurity which varies in amount depending on the labeling conditions used. Antibody binding studies show that the peptide can bind two hMN-14× 679 bispecific antibodies and that it does not bind hMN-14× 734. The peptide is very stable in human serum and appears to be just as stable in mouse serum. The mouse serum antibody binding SEC HPLC experiments do show some peaks in the antibody region when there should be none but this is probably due to the presence of the antibody in the injector or syringe from previous injections.

Conclusions:

The peptide labels well and is stable in mouse and human serum.

Example Peptides for Carrying Therapeutic/Imaging Radioisotopes to Tumors via Bispecific Antibody Tumor Pre-targeting DOTA-Phe-Lys(HSG)-Tyr-Lys(HSG)-NH$_2$ (IMP 237) was synthesized to deliver therapeutic radioisotopes such as $^{90}$Y or $^{177}$Lu to tumors via bispecific antibody tumor pretargeting. The bispecific antibody is composed of one portion which binds to an antigen on the tumor and another portion which binds to the HSG peptide. The antibody which binds the HSG peptide is 679. This system can also be used to deliver imaging isotopes such as $^{111}$In-111.

Synthesis of IMP 237

IMP 237 was synthesized on Sieber Amide resin (Nova-Biochem) using standard Fmoc based solid phase peptide synthesis to assemble the peptide backbone with the following protected amino acids, in order: Fmoc-Lys(Aloc)-OH, Fmoc-Tyr(But)-OH, Fmoc-Lys(Aloc)-OH, Fmoc-Phe-OH, (Reagents from Advanced Chemtech) tri-t-butyl DOTA (Macrocyclics). The side lysine side chains were then deprotected with Pd[P(Ph)$_3$]$_4$ by the method of Dangles et. al. *J. Org. Chem.* 52:4984-4993 (1987). The HSG ligands were then added as Trityl HSG (synthesis described below) using the BOP/HBTU double coupling procedure used to attach the amino acids. The peptide was cleaved from the resin and the protecting groups were removed by treatment with TFA. The peptide was purified by HPLC to afford 0.6079 g of peptide from 1.823 g of Fmoc-Lys(Aloc)-Tyr(But)-Lys(Aloc)-NH-Sieber amide resin.

Synthesis of N-Trityl-HSG-OH

Glycine t-butyl ester hydrochloride (15.263 g, 9.1× 10$^{-2}$ mol) and 19.760 g Na$_2$CO$_3$ were mixed, then suspended in 50 mL H$_2$O and cooled in an ice bath. Succinic anhydride (9.142 g, 9.14×10$^{-2}$ mol) was then added to the reaction solution which was allowed to warm slowly to room temperature and stir for 18 hr. Citric acid (39.911 g) was dissolved in 50 mL H$_2$O and slowly added to the reaction solution and then extracted with 2×150 mL EtOAc. The organic extracts were dried over Na$_2$SO$_4$, filtered and concentrated to afford 25.709 g of a white solid.

The crude product (25.709 g) was dissolved in 125 mL dioxane, cooled in a room temperature water bath and mixed with 11.244 g of N-hydroxysuccinimide. Diisopropylcarbodiimide 15.0 mL was added to the reaction solution which was allowed to stir for one hour. Histamine dihydrochloride (18.402 g, 1.00×10$^{-1}$ mol) was then dissolved in 100 mL DMF and 35 mL diisopropylethylamine. The histamine mixture was added to the reaction solution which was stirred at room temperature for 21 hr. The reaction was quenched with 100 mL water and filtered to remove a precipitate. The solvents were removed under hi-vacuum on the rotary evaporator. The crude product was dissolved in 300 mL dichloromethane and extracted with 100 mL saturated NaHCO$_3$. The organic layer was dried over Na$_2$SO$_4$ and concentrated to afford 34.19 g of crude product as a yellow oil.

The crude product (34.19 g) was dissolved in 50 mL chloroform and mixed with 31 mL diisopropylethylamine. Triphenylmethyl chloride (25.415 g) was dissolved in 50 ml chloroform and added dropwise to the stirred reaction solution which was cooled in an ice bath. The reaction was stirred for 45 min and then quenched with 100 mL H$_2$O. The layers were separated and the organic solution was dried over Na$_2$SO$_4$ and concentrated to form a green gum. The gum was triturated with 100 mL Et$_2$O to form a yellow precipitate which was washed with 3×50 mL portions of Et$_2$O. The solid was vacuum dried to afford 30.641 g (59.5% overall yield) of N-trityl-HSG-t-butyl ester.

N-trityl-HSG-t-butyl ester (20.620 g, 3.64×10$^{-2}$ mol) was dissolved in a solution of 30 mL chloroform and 35 mL glacial acetic acid. The reaction was cooled in an ice bath and 15 mL of BF$_3$.Et$_2$O was slowly added to the reaction solution. The reaction was allowed to warm slowly to room temperature and mix for 5 hr. The reaction was quenched by pouring into 200 mL 1M NaOH and the product was extracted with 200 mL chloroform. The organic layer was dried over Na$_2$SO$_4$ and concentrated to afford a crude gum which was triturated with 100 mL Et$_2$O to form a precipitate. The crude precipitate was poured into 400 mL 0.5 M pH 7.5 phosphate buffer and extracted with 2×200 mL EtOAc. The aqueous layer was acidified to pH 3.5 with 1 M HCl and extracted with 2×200 mL chloroform. A precipitate formed and was collected by filtration (8.58 g). The precipitate was the desired product by HPLC comparison to a previous sample (ESMS MH+511).

Radiolabeling

Labeling with $^{111}$In

The $^{111}$In (~300 µCi/kit) was diluted to 0.5 mL in deionized water and added to the lyophilized kits. The kits were heated in a boiling water bath for 15 min, the vials were cooled and 0.5 mL of 2.56×10$^{-5}$ M In in 0.5 M acetate buffer was added and the kits were again heated in the boiling water bath for 15 min. The labeled peptide vials were cooled to room temperature and evaluated by reverse phase HPLC (HPLC conditions: Waters Nova-Pak C-18, 8×100 mm RCM column eluted at 3 mL/min with a linear gradient from 100% (0.1% TFA in H$_2$O) to 100% (90% CH$_3$CN, 0.1% TFA, 10% H$_2$O)). The HPLC analysis revealed that the minimum concentration of peptide needed for labeling (4.7% loose $^{111}$In), with this formulation, was 35 µg/mL. The reverse phase HPLC trace showed a sharp $^{111}$In labeled peptide peak. The labeled peptide was completely bound when mixed with excess 679 IgG by size exclusion HPLC.

In-Vivo Studies

Nude mice bearing GW-39 human colonic xenograft tumors (100-500 mg) were injected with the bispecific antibody hMN-14×m679 (1.5×10$^{-10}$ mol). The antibody was allowed to clear for 24 hr before the $^{111}$In labeled peptide (8.8 µCi, 1.5×10$^{-11}$ mol) was injected. The animals were sacrificed at 3, 24, 48 hr post injection.

The results of the biodistribution studies of the peptide in the mice pretargeted with hMN-14×m679 are shown in Table 1. The tumor to non-tumor ratios of the peptides in the pretargeting study are show in Table 2.

TABLE 1

Pretargeting With $^{111}$In Labeled Peptide 24 hr After Injection of hMN-14 x m679
% Injected/g Tissue

| Tissue | 3 hr After $^{111}$In IMP 237 | 24 hr After $^{111}$In IMP 237 | 48 hr After $^{111}$In IMP 237 |
|---|---|---|---|
| GW-39 | 7.25 ± 2.79 | 8.38 ± 1.70 | 5.39 ± 1.46 |
| Liver | 0.58 ± 0.13 | 0.62 ± 0.09 | 0.61 ± 0.16 |
| Spleen | 0.50 ± 0.14 | 0.71 ± 0.16 | 0.57 ± 0.15 |
| Kidney | 3.59 ± 0.75 | 2.24 ± 0.40 | 1.27 ± 0.33 |
| Lungs | 1.19 ± 0.26 | 0.44 ± 0.10 | 0.22 ± 0.06 |
| Blood | 2.42 ± 0.61 | 0.73 ± 0.17 | 0.17 ± 0.06 |
| Stomach | 0.18 ± 0.03 | 0.09 ± 0.02 | 0.07 ± 0.02 |
| Sm. Int. | 0.65 ± 0.74 | 0.18 ± 0.03 | 0.11 ± 0.02 |
| Lg. Int. | 0.30 ± 0.07 | 0.17 ± 0.03 | 0.13 ± 0.03 |

TABLE 2

Pretargeting With $^{111}$In Labeled Peptide 24 hr After Injection of hMN-14 x m679
Tumor/Non-Tumor Tissue Ratios

| Tissue | 3 hr After $^{111}$In IMP 237 | 24 hr After $^{111}$In IMP 237 | 48 hr After $^{111}$In IMP 237 |
|---|---|---|---|
| Liver | 12.6 ± 4.44 | 13.6 ± 2.83 | 8.88 ± 1.78 |
| Spleen | 15.1 ± 6.32 | 12.1 ± 2.86 | 9.50 ± 1.62 |
| Kidney | 2.04 ± 0.74 | 3.84 ± 1.04 | 4.25 ± 0.19 |
| Lungs | 6.11 ± 1.96 | 19.6 ± 5.91 | 25.4 ± 6.00 |
| Blood | 3.04 ± 1.13 | 11.9 ± 3.20 | 31.9 ± 4.79 |
| Stomach | 40.5 ± 16.5 | 104. ± 39.6 | 83.3 ± 16.5 |
| Sm. Int. | 18.9 ± 12.6 | 47.5 ± 10.3 | 49.5 ± 7.83 |
| Lg. Int. | 25.2 ± 10.6 | 50.1 ± 16.7 | 43.7 ± 9.35 |

Serum Stability of DOTA-Phe-Lys(HSG)-Tyr-Lys(HSG)-NH$_2$ (IMP 237) and DOTA-Phe-Lys(HSG)-D-Tyr-Lys(HSG)-NH$_2$ (IMP 241)

Peptide Labeling and HPLC Analysis

The peptides, IMP 237 and IMP 241, were labeled according to the procedure described by Karacay et. al. Bioconjugate Chem. 11:842-854 (2000). The peptide, IMP 241 (0.0019 g), was dissolved in 587 µl 0.5 M NH$_4$Cl, pH 5.5. A 1.7 µL aliquot of the peptide solution was diluted with 165 µl 0.5 M NH$_4$Cl, pH 5.5. The $^{111}$In (1.8 mCi) in 10 µL was added to the peptide solution and the mixture was heated in a boiling water bath for 30 min.

The labeled peptide was analyzed by HPLC using a Waters 8×100 mm radial-pak, nova-pak C-18 RCM cartridge column. The column was eluted at 3 mL/min with a linear gradient which started with 100% of 0.1% TFA in water and went to 100% of 0.1% TFA in 90% acetonitrile and 10% water over 10 min. There was about 6% loose $^{111}$In in this labeling which came out at the void volume of the column (1.6 min). There were also some $^{111}$In labeled peaks at 5 min and 6.6 to 8 min. The $^{111}$In labeled peptide was eluted at 8.8 min as a single peak. The HPLC profile of $^{111}$In IMP 237 was nearly identical to $^{111}$In IMP 241.

Serum Stability

An aliquot (30 µL) of $^{111}$In IMP 241 was placed in 300 µL of fresh mouse serum and placed in a 37° C. incubator. The peptide was monitored as described above by HPLC.

An aliquot (24 µL) of $^{111}$In IMP 237 was placed in 230 µL of fresh mouse serum and placed in a 37° C. incubator. The peptide was monitored as described above by HPLC.

The analysis showed that the $^{111}$In IMP 241 decomposed slightly (~5%) after 22 hr in mouse serum at 37° C. The $^{111}$In IMP 237 was about 70% converted to the shorter retention time peak after incubation for 22 hr at 37° C.

Conclusion

The D-tyrosine in the IMP 241 peptide slows the decomposition of the peptide in mouse serum compared to IMP 237.

In Vivo Stability of IMP 237 and IMP 241 Compared

The in vivo stabilities of $^{111}$In IMP 237 and $^{111}$In IMP 241 were compared by examining (by HPLC) urine samples from mice at 30 and 60 min. The peptides, IMP 241 and IMP 237, were $^{111}$In-111 labeled as described above.

The labeled peptides were injected into Balb/c mice which were sacrificed at 30 min and 60 min post injection of the peptides using one mouse per time point. The HPLC traces indicated that $^{111}$In IMP 241 was excreted intact while $^{111}$In IMP 237 was almost completely metabolized to a new $^{111}$In labeled peptide.

Conclusion

The replacement of Tyr with D-Tyr in the peptide backbone lessened metabolism of the peptide in-vivo.

Synthesis of DOTA-D-Asp-D-Lys(HSG)-D-Asp-D-Lys(HSG)-NH$_2$ (IMP 271)

IMP 271 was synthesized on Sieber Amide resin (Nova-Biochem) using standard Fmoc based solid phase peptide synthesis to assemble the peptide backbone with the following protected amino acids, in order: Fmoc-D-Lys(Aloc)-OH, Fmoc-D-Asp(But)-OH, Fmoc-D-Lys(Aloc)-OH, and Fmoc-D-Asp(But)-OH, (Reagents from Advanced Chemtech). The linear peptide was assembled and the DOTA-tris(tBu) ester (Macrocyclics) was added to the N-terminus. The Aloc side chains on the D-lysines were then removed with Pd[P(Ph)$_3$]$_4$ by the method of Dangles et. al. J. Org. Chem. 52:4984-4993 (1987). The HSG ligands were then added as Trityl HSG (previously described) using the BOP/HBTU double coupling procedure used to attach the amino acids. The peptide was cleaved from the resin and the protecting groups were removed by treatment with TFA. The peptide was purified by HPLC.

Comparison biodistribution of the new peptides $^{111}$In-IMP 281 and IMP 284 to IMP 241 in Pretargeting and when injected alone Goal: Tumor targeting of IMP 281 was examined in this example. Reagents:

hMN-14×m679 Fab'×Fab': GN, LN 073102, 10.9 mg/mL

NCr nudes: (NCI) from Taconic, 4 weeks of age

GW39: generation # 8; SC 300 µL of 10%;
IMP 241: DOTA-Phe-Lys(HSG)-D-Tyr-Lys(HSG)-NH$_2$;
IMP 281: DOTA-D-Ala-D-Lys(HSG)-D-Glu-D-Lys(HSG)-NH$_2$; MH+1361
IMP 284: DOTA-D-Phe-D-Lys(HSG)-D-Tyr-D-Lys(HSG)-NH$_2$; MH+1471

Group I. IMP 241

A. Pretargeting

I-125 labeled bsMab (15 µg) will be injected into 10 GW xenograft bearing mice, with tumors ≧0.2 g. After allowing time for localization and clearance from blood, $^{111}$In-IMP-241 will be injected. At the times shown above, 5 mice per time point will be necropsied. Tissues (tumor, liver, spleen, kidney, lungs, blood, stomach, large and small intestines) will be isolated, weighed and counted in the appropriate windows.

B. Peptide Alone $^{111}$In-IMP-241 (8.8 µCi, 1.5×10$^{-11}$ mol) will be injected into 10 tumor bearing mice. At 3 and 24 h post injection, 5 mice per time point will be necropsied. Tissues (tumor, liver, spleen, kidney, lungs, blood, stomach, large and small intestines) will be isolated, weighed and counted in the appropriate windows.

Group II. IMP 281

A. Pretargeting

I-125 labeled bsMab (15 µg) will be injected into 10 GW xenograft bearing mice, with tumors ≧0.2 g. After allowing time for localization and clearance from blood, 111In-IMP-281 will be injected. At the times shown above, 5 mice per time point will be necropsied. Tissues (tumor, liver, spleen, kidney, lungs, blood, stomach, large and small intestines) will be isolated, weighed and counted in the appropriate windows.

B. Peptide Alone $^{111}$In-IMP-281 (8.8 µCi, 1.5×10$^{-1}$ mol) will be injected into 12 tumor bearing mice. At 3 and 24 h post injection, 5 mice per time point will be necropsied, at 30 min, 2 mice will be necropsied. Tissues (tumor, liver, spleen, kidney, lungs, blood, stomach, large and small intestines) will be isolated, weighed and counted in the appropriate windows.

Group III. IMP 284

A. Pretargeting

I-125 labeled bsMab (15 µg) will be injected into 10 GW xenograft bearing mice, with tumors ≧0.2 g. After allowing time for localization and clearance from blood, $^{111}$In-IMP-281 will be injected. At the times shown above, 5 mice per time point will be necropsied. Tissues (tumor, liver, spleen, kidney, lungs, blood, stomach, large and small intestines) will be isolated, weighed and counted in the appropriate windows.

B. Peptide Alone $^{111}$In-IMP-284 (8.8 µCi, 1.5×10–11 mol) will be injected into 13 tumor bearing mice. At 3 and 24 h post injection, 5 mice per time point will be necropsied, at 30 min 3 mice will be necropsied. Tissues (tumor, liver, spleen, kidney, lungs, blood, stomach, large and small intestines) will be isolated, weighed and counted in the appropriate windows.

Radiolabeling:

IMP-241 peptide will be labeled with In-111 according to protocol below.

$^{111}$InCl$_3$ (3mCi)

0.5 M ammonium acetate, pH 5.5 (3× volumes of In-111) peptide 2.32 µL, 2.2×10–3 M in 0.5 M ammonium acetate, pH 5.5

Centrifuge

Heat in boiling water bath for 30 min.

Cool on ice bath for 5 min

Centrifuge

Add DTPA (0.1 M in 0.1 M NaOAc, pH 6.5) to a final DTPA concentration of 3 mM

Let sit at room temperature for 15 min

Add 0.1 M sodium acetate, pH 6.5 to 1 mL

Analyze by ITLC and HPLC. ITLC strips will be developed in saturated sodium chloride and water:ethanol:ammonia (5:2:1)

Radiolabeling:

IMP-281 peptide will be labeled with In-111 according to protocol below.

$^{111}$InCl$_3$ (3mCi)

0.5 M ammonium acetate, pH 5.5 (3× volumes of In-111) peptide 2.32 µL, 2.2×10–3 M in 0.5 M ammonium acetate, pH 5.5

Centrifuge

Heat in boiling water bath for 30 min.

Cool on ice bath for 5 min

Centrifuge

Add DTPA (0.1 M in 0.1 M NaOAc, pH 6.5) to a final DTPA concentration of 3 mM

Let sit at room temperature for 15 min

Add 0.1 M sodium acetate, pH 6.5 to 1 mL

Analyze by ITLC and HPLC. ITLC strips will be developed in saturated sodium chloride and water:ethanol:ammonia (5:2:1)

Radiolabeling:

IMP-284 peptide will be labeled with In-111 according to protocol below.

$^{111}$InCl$_3$ (3mCi)

0.5 M ammonium acetate, pH 5.5 (3× volumes of In-111) peptide 2.32 µL, 2.2×10–3 M in 0.5 M ammonium acetate, pH 5.5

Centrifuge

Heat in boiling water bath for 30 min.

Cool on ice bath for 5 min

Centrifuge

Add DTPA (0.1 M in 0.1 M NaOAc, pH 6.5) to a final DTPA concentration of 3 mM

Let sit at room temperature for 15 min

Add 0.1 M sodium acetate, pH 6.5 to 1 mL

Analyze by ITLC and HPLC. ITLC strips will be developed in saturated sodium chloride and water:ethanol:ammonia (5:2:1)

Results: comparison of the peptides 111In-IMP 241, 281 and 284 alone and pretargeted with hMN14xm679 Fab'xFab'

This example compared IMP 241 with the two all D-amino acid backbone peptides described in the previous example, alone and in pretargeting. Protocol and biodistribution data are attached.

Radiolabeling data for the peptides:

| | ITLC | |
|---|---|---|
| Peptide | % unbound | % colloid |
| IMP 241 | 1.5 | 0.3 |
| IMP 281 | 0.6 | 0.3 |
| IMP 284 | 0.9 | 0.3 |

| | SE HPLC of $^{111}$In labeled peptides | | | |
|---|---|---|---|---|
| peptide | RT alone | % recovery | RT of Peptide + hMN14xm679 | % shift bsAb | % recovery |
| IMP 241 | 13.81 | 97.9 | ND | | |
| IMP 281 | 13.46 | 99 | 8.80 | 99 | 74 |
| IMP 284 | 13.88 | 96.4 | 8.77 | 99 | 72 |

| C18 reverse HPLC of the 111In-labeled peptides: | | |
|---|---|---|
| Peptide | RT, min | % (area) |
| IMP 241 | 2.4 | 1.8 |
|  | 11.51 | 97.7 |
| IMP 281 | 2.3 | 0.75 |
|  | 8.5 | 98.5 |
| IMP 284 | 2.3 | 1.3 |
|  | 11.61 | 98 |

Figure 27A:
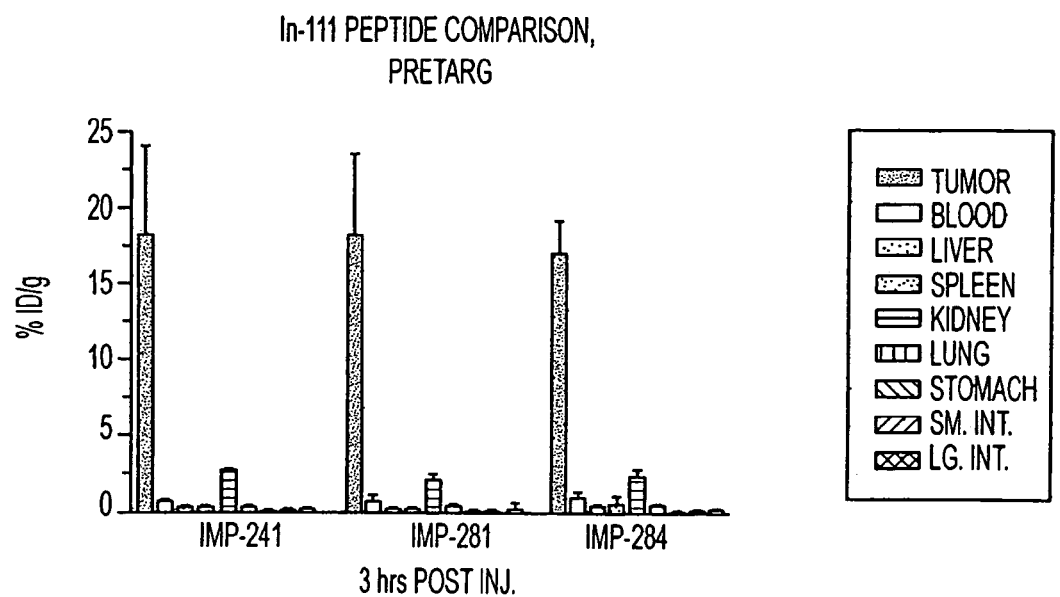
FIG. 27 shows a comparison of tissue uptake of peptides IMP 241, 281 and 284 in pretargeting, 3 (top) and 24 h (bottom) post peptide injection.
Figure 27B:
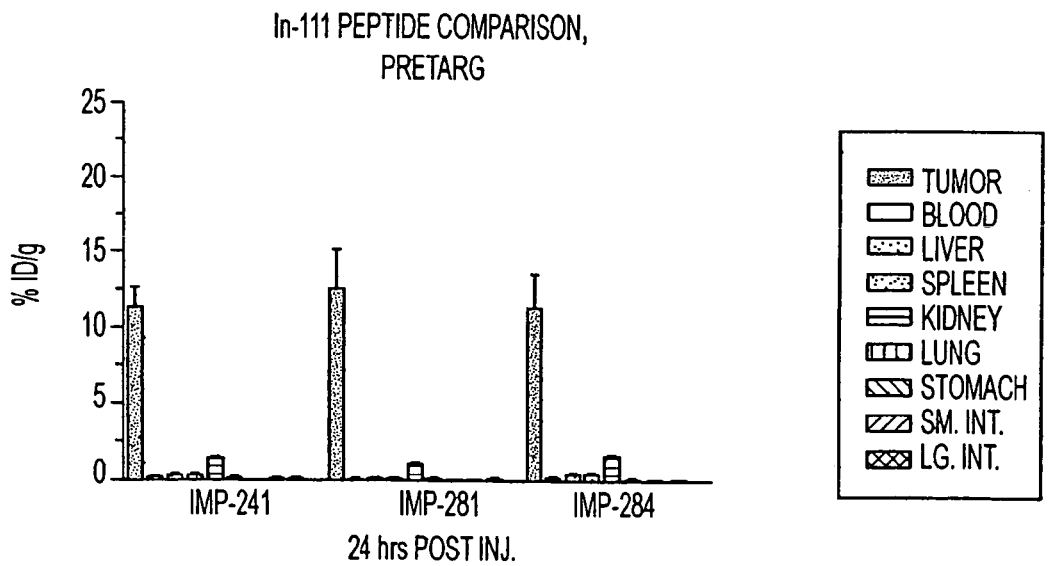
Figure 28A:
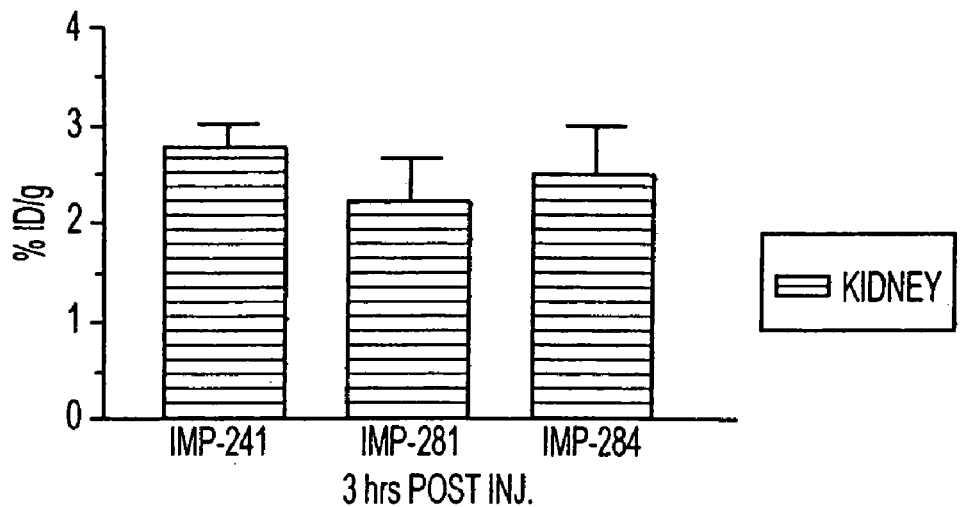
FIG. 28 shows a comparison of peptide kidney uptake in pretargeting at 3 and 24 h post peptide injection.
Figure 28B:
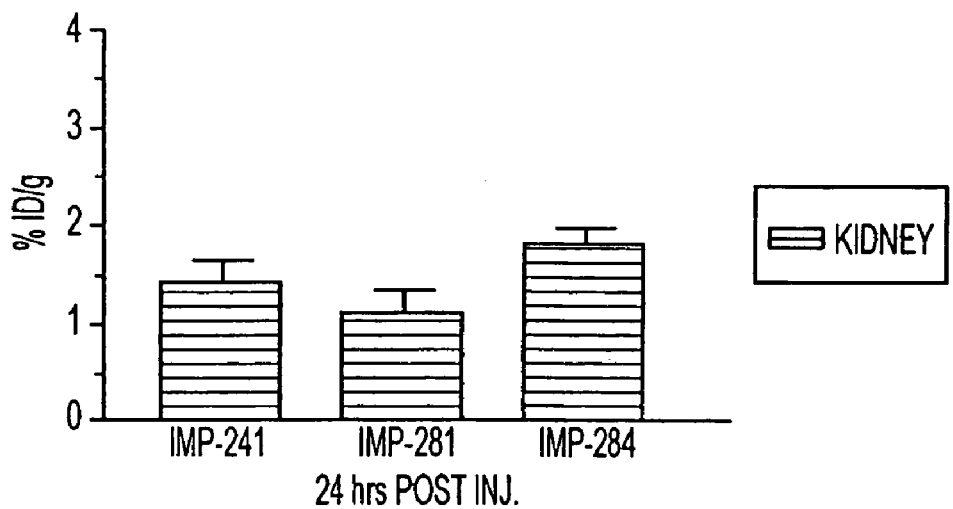
Figure 29A:
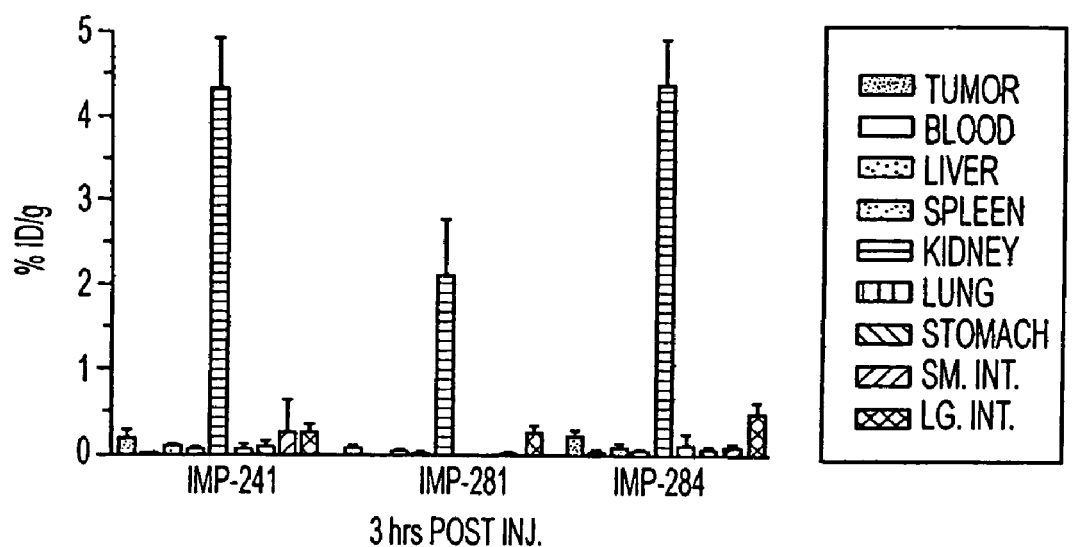
FIG. 29 shows tissue uptake of IMP 241, 281 and 284 peptides at 3 and 24 hours post injection.
Figure 29B:
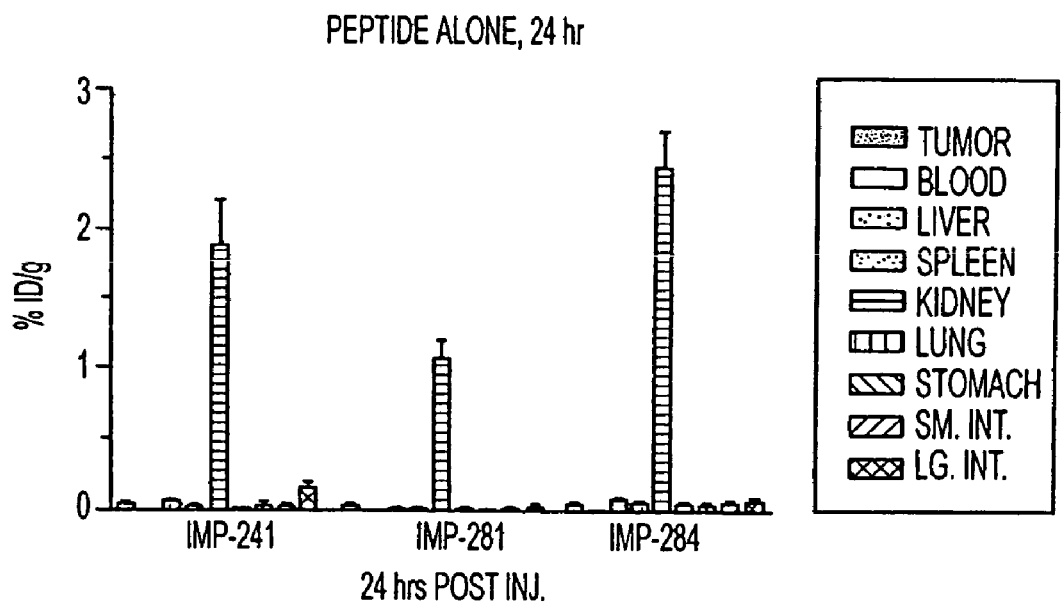

Biodistribution:

Biodistribution data is shown below. In comparing the 3 peptides, tumor peptide uptake was similar for all of the 3 peptides in pretargeting after 3 and 24 h post injection, FIG. 27. IMP 281 showed lower kidney uptake than IMP 241 and 284 in pretargeting as well as when given alone, FIGS. 28 and 29.

Conclusions: The bsAb and peptide tumor uptakes were the same in the three Pretargeting groups with the different peptides. IMP 281 showed slightly lower kidney uptake in pretargeting than with IMP 241 and 284. Reduced kidney uptake for IMP 281 was more obvious when the peptides were injected alone.

TABLE 3

Time post Injection: 24 hr
Experiment Description: Pretargeting Bio with In-111-IMP-241 vs IMP-281 vs IMP-284
Group #: IA ($^{125}$I --> 24 hrs --> $^{111}$In-IMP-241)
uCi injected: 6
Mean Body weight: 21.09

| Tissue | n | Weight | STD WT | % ID/g | STD % ID/g | % ID/org | STD % ID/org | T/NT | STD T/NT |
|---|---|---|---|---|---|---|---|---|---|
| MAb 1 isotope injected I-125 | | | | | | | | | |
| MAb 1 injected: hMN-14 x m679 | | | | | | | | | |
| Corrected MAb 1 cpm injected: 9802182 | | | | | | | | | |
| Tumor | 5 | 0.447 | 0.054 | 3.06 | 0.61 | 1.35 | 0.22 | 1.00 | 0.00 |
| Liver | 5 | 1.223 | 0.197 | 0.19 | 0.06 | 0.22 | 0.04 | 17.04 | 3.17 |
| Spleen | 5 | 0.081 | 0.018 | 0.20 | 0.06 | 0.02 | 0.00 | 16.05 | 3.09 |
| Kidney | 5 | 0.139 | 0.016 | 0.14 | 0.03 | 0.02 | 0.00 | 22.27 | 3.44 |
| Lungs | 5 | 0.153 | 0.026 | 0.13 | 0.03 | 0.02 | 0.00 | 24.52 | 7.49 |
| Blood | 5 | 0.241 | 0.002 | 0.15 | 0.03 | 0.23 | 0.03 | 20.26 | 3.91 |
| Stomach | 5 | 0.493 | 0.160 | 0.50 | 0.27 | 0.22 | 0.09 | 8.14 | 5.42 |
| Sm Int | 5 | 1.124 | 0.235 | 0.08 | 0.04 | 0.09 | 0.05 | 43.63 | 16.32 |
| Lg Int | 5 | 0.875 | 0.262 | 0.08 | 0.02 | 0.06 | 0.01 | 41.10 | 12.16 |
| MAb 2 isotope injected in-111 | | | | | | | | | |
| MAb 2 injected: IMP-241 | | | | | | | | | |
| MAb 2 cpm injected: 4975201.6 | | | | | | | | | |
| Tumor | 5 | 0.447 | 0.054 | 11.31 | 1.38 | 5.05 | 0.75 | 1.00 | 0.00 |
| Liver | 5 | 1.223 | 0.197 | 0.28 | 0.09 | 0.33 | 0.06 | 42.24 | 8.25 |
| Spleen | 5 | 0.081 | 0.018 | 0.28 | 0.11 | 0.02 | 0.01 | 44.15 | 13.06 |
| Kidney | 5 | 0.139 | 0.016 | 1.41 | 0.21 | 0.20 | 0.02 | 8.06 | 0.83 |
| Lungs | 5 | 0.153 | 0.026 | 0.19 | 0.08 | 0.03 | 0.01 | 67.48 | 20.75 |
| Blood | 5 | 0.241 | 0.002 | 0.19 | 0.06 | 0.29 | 0.07 | 61.67 | 9.61 |
| Stomach | 5 | 0.493 | 0.160 | 0.04 | 0.01 | 0.02 | 0.01 | 344.86 | 101.23 |
| Sm Int | 5 | 1.124 | 0.235 | 0.08 | 0.04 | 0.08 | 0.03 | 168.22 | 53.20 |
| Lg Int | 5 | 0.875 | 0.262 | 0.08 | 0.02 | 0.07 | 0.02 | 141.82 | 33.27 |

TABLE 4

Time post Injection: 3 hr
Experiment Description: Pretargeting Bio with In-111-IMP-241 vs IMP-281 vs IMP-284
Group #: IA ($^{125}$I --> 24 hrs --> $^{111}$In-IMP-241)
uCi injected: 6
Mean Body weight: 20.09

| Tissue | n | Weight | STD WT | % ID/g | STD % ID/g | % ID/org | STD % ID/org | T/NT | STD T/NT |
|---|---|---|---|---|---|---|---|---|---|
| MAb 1 isotope injected: I-125 | | | | | | | | | |
| MAb 1 injected: hMN-14 x m679 | | | | | | | | | |
| Corrected MAb 1 cpm injected: 9892972 | | | | | | | | | |
| Tumor | 5 | 0.489 | 0.065 | 5.67 | 1.50 | 2.73 | 0.62 | 1.00 | 0.00 |
| Liver | 5 | 1.069 | 0.154 | 0.57 | 0.12 | 0.60 | 0.12 | 10.36 | 3.25 |
| Spleen | 5 | 0.083 | 0.009 | 0.65 | 0.12 | 0.05 | 0.01 | 8.76 | 2.05 |
| Kidney | 5 | 0.131 | 0.020 | 0.40 | 0.06 | 0.05 | 0.01 | 14.38 | 3.80 |

TABLE 4-continued

Time post Injection: 3 hr
Experiment Description: Pretargeting Bio with In-111-IMP-241 vs IMP-281 vs IMP-284
Group #: IA ($^{125}$I --> 24 hrs --> $^{111}$In-IMP-241)
uCi injected: 6
Mean Body weight: 20.09

| Tissue | n | Weight | STD WT | % ID/g | STD % ID/g | % ID/org | STD % ID/org | T/NT | STD T/NT |
|---|---|---|---|---|---|---|---|---|---|
| Lungs | 5 | 0.139 | 0.020 | 0.40 | 0.04 | 0.05 | 0.01 | 14.49 | 4.16 |
| Blood | 5 | 0.233 | 0.003 | 0.57 | 0.07 | 0.84 | 0.13 | 10.16 | 2.89 |
| Stomach | 5 | 0.337 | 0.046 | 2.87 | 0.86 | 0.94 | 0.21 | 2.21 | 1.06 |
| Sm Int | 5 | 0.962 | 0.176 | 0.25 | 0.05 | 0.24 | 0.06 | 23.84 | 8.09 |
| Lg Int | 5 | 0.814 | 0.133 | 0.36 | 0.07 | 0.29 | 0.05 | 16.18 | 4.96 |

MAb 2 isotope injected: In-111
MAb 2 injected: IMP-241
MAb 2 cpm injected: 6151305

| Tissue | n | Weight | STD WT | % ID/g | STD % ID/g | % ID/org | STD % ID/org | T/NT | STD T/NT |
|---|---|---|---|---|---|---|---|---|---|
| Tumor | 5 | 0.489 | 0.065 | 17.92 | 6.32 | 8.62 | 2.65 | 1.00 | 0.00 |
| Liver | 5 | 1.069 | 0.154 | 0.38 | 0.11 | 0.40 | 0.06 | 47.71 | 14.04 |
| Spleen | 5 | 0.083 | 0.009 | 0.31 | 0.07 | 0.02 | 0.00 | 57.95 | 11.64 |
| Kidney | 5 | 0.131 | 0.020 | 2.78 | 0.25 | 0.36 | 0.04 | 6.38 | 1.78 |
| Lungs | 5 | 0.139 | 0.020 | 0.54 | 0.10 | 0.07 | 0.01 | 33.54 | 10.60 |
| Blood | 5 | 0.233 | 0.003 | 0.76 | 0.17 | 1.11 | 0.18 | 23.74 | 6.56 |
| Stomach | 5 | 0.337 | 0.046 | 0.08 | 0.02 | 0.03 | 0.00 | 226.83 | 73.39 |
| Sm Int | 5 | 0.962 | 0.176 | 0.16 | 0.05 | 0.15 | 0.03 | 120.60 | 46.41 |
| Lg Int | 5 | 0.814 | 0.133 | 0.22 | 0.09 | 0.17 | 0.06 | 88.84 | 31.75 |

TABLE 5

Time post Injection: 24 hr
Experiment Description: Pretargeting Bio with In-111-IMP-241 vs IMP-281 vs IMP-284
Group #: IB
uCi injected: 8.8
CPM Injected: 6296515
Mean Body weight: 19.89
Isotope injected: In-111
MAb injected: IMP-241

| Tissue | n | Weight | STD WT | % ID/g | STD % ID/g | % ID/org | STD % ID/org | T/NT | STD T/NT |
|---|---|---|---|---|---|---|---|---|---|
| Tumor | 5 | 0.360 | 0.086 | 0.038 | 0.013 | 0.015 | 0.008 | 1.000 | 0.000 |
| Liver | 5 | 1.008 | 0.125 | 0.071 | 0.016 | 0.070 | 0.010 | 0.542 | 0.154 |
| Spleen | 5 | 0.067 | 0.015 | 0.037 | 0.009 | 0.002 | 0.001 | 1.026 | 0.196 |
| Kidney | 5 | 0.140 | 0.039 | 1.857 | 0.346 | 0.255 | 0.056 | 0.021 | 0.006 |
| Lung | 5 | 0.137 | 0.012 | 0.018 | 0.002 | 0.002 | 0.000 | 2.078 | 0.536 |
| Blood | 5 | 0.236 | 0.003 | 0.000 | 0.000 | 0.000 | 0.000 | 569.530 | 196.879 |
| Stomach | 5 | 0.378 | 0.074 | 0.040 | 0.026 | 0.015 | 0.008 | 1.140 | 0.604 |
| Small Int. | 5 | 0.952 | 0.204 | 0.044 | 0.019 | 0.039 | 0.011 | 0.898 | 0.136 |
| Large Int. | 5 | 0.779 | 0.181 | 0.156 | 0.047 | 0.121 | 0.042 | 0.261 | 0.124 |

All blood CPMs were 0
All spleen CPMs were 200 or less
All lung CPMs were 170 or less

TABLE 6

Time post Injection: 3 hr
Experiment Description: Pretargeting Bio with In-111-IMP-241 vs IMP-281 vs IMP-2840
Group #: IB
uCi injected: 8.8
CPM Injected: 7771826.6
Mean Body weight: 18.08
Isotope injected: In-111
MAb injected: IMP-241

| Tissue | n | Weight | STD WT | % ID/g | STD % ID/g | % ID/org | STD % ID/org | T/NT | STD T/NT |
|---|---|---|---|---|---|---|---|---|---|
| Tumor | 5 | 0.376 | 0.127 | 0.209 | 0.120 | 0.066 | 0.008 | 1.000 | 0.000 |
| Liver | 5 | 0.875 | 0.130 | 0.149 | 0.012 | 0.129 | 0.011 | 1.425 | 0.874 |
| Spleen | 5 | 0.066 | 0.014 | 0.078 | 0.007 | 0.005 | 0.001 | 2.738 | 1.701 |
| Kidney | 5 | 0.113 | 0.014 | 4.327 | 0.559 | 0.488 | 0.081 | 0.047 | 0.020 |
| Lung | 5 | 0.129 | 0.017 | 0.114 | 0.043 | 0.015 | 0.007 | 2.098 | 1.561 |
| Blood | 5 | 0.232 | 0.003 | 0.010 | 0.003 | 0.013 | 0.003 | 22.736 | 14.408 |
| Stomach | 5 | 0.263 | 0.034 | 0.128 | 0.091 | 0.032 | 0.022 | 2.430 | 1.763 |

TABLE 6-continued

Time post Injection: 3 hr
Experiment Description: Pretargeting Bio with In-111-IMP-241 vs IMP-281 vs IMP-2840
Group #: IB
uCi injected: 8.8
CPM Injected: 7771826.6
Mean Body weight: 18.08
Isotope injected: In-111
MAb injected: IMP-241

| Tissue | n | Weight | STD WT | % ID/g | STD % ID/g | % ID/org | STD % ID/org | T/NT | STD T/NT |
|---|---|---|---|---|---|---|---|---|---|
| Small Int. | 5 | 0.818 | 0.113 | 0.293 | 0.389 | 0.229 | 0.301 | 1.754 | 1.473 |
| Large Int. | 5 | 0.689 | 0.173 | 0.308 | 0.089 | 0.201 | 0.022 | 0.756 | 0.523 |

All blood CPMs were 250 or less

TABLE 7

Time post Injection: 24 hr
Experiment Description: Pretargeting Bio with In-111-IMP-241 vs IMP-281 vs IMP-284
Group #: IIA ($^{125}$I --> 24 hrs -->$^{111}$In-IMP-281)
uCi injected: 6
Mean Body weight: 18.92

| Tissue | n | Weight | STD WT | % ID/g | STD % ID/g | % ID/org | STD % ID/org | T/NT | STD T/NT |
|---|---|---|---|---|---|---|---|---|---|
| | | | | MAb 1 isotope injected: I-125 | | | | | |
| | | | | MAb 1 injected: hMN-14 x m679 | | | | | |
| | | | | Corrected MAb 1 cpm injected: 9788320 | | | | | |
| Tumor | 5 | 0.590 | 0.042 | 3.51 | 0.74 | 2.05 | 0.36 | 1.00 | 0.00 |
| Liver | 5 | 0.919 | 0.060 | 0.25 | 0.02 | 0.23 | 0.01 | 14.08 | 2.06 |
| Spleen | 5 | 0.070 | 0.005 | 0.26 | 0.03 | 0.02 | 0.00 | 13.49 | 3.14 |
| Kidney | 5 | 0.126 | 0.016 | 0.16 | 0.03 | 0.02 | 0.00 | 22.05 | 2.77 |
| Lungs | 5 | 0.149 | 0.016 | 0.19 | 0.04 | 0.03 | 0.00 | 19.09 | 2.82 |
| Blood | 5 | 0.239 | 0.002 | 0.21 | 0.05 | 0.29 | 0.05 | 16.63 | 1.19 |
| Stomach | 5 | 0.334 | 0.041 | 0.84 | 0.43 | 0.28 | 0.14 | 4.58 | 1.27 |
| Sm Int | 5 | 0.882 | 0.064 | 0.08 | 0.02 | 0.07 | 0.02 | 44.14 | 4.36 |
| Lg Int | 5 | 0.793 | 0.090 | 0.10 | 0.04 | 0.08 | 0.04 | 35.48 | 7.79 |
| | | | | MAb 2 isotope injected: In-111 | | | | | |
| | | | | MAb 2 injected: IMP-281 | | | | | |
| | | | | MAb 2 cpm injected: 6659738.3 | | | | | |
| Tumor | 5 | 0.590 | 0.042 | 12.66 | 2.55 | 7.41 | 1.30 | 1.00 | 0.00 |
| Liver | 5 | 0.919 | 0.060 | 0.28 | 0.07 | 0.26 | 0.05 | 45.21 | 6.11 |
| Spleen | 5 | 0.070 | 0.005 | 0.23 | 0.04 | 0.02 | 0.00 | 54.68 | 12.53 |
| Kidney | 5 | 0.126 | 0.016 | 1.09 | 0.22 | 0.14 | 0.03 | 12.21 | 4.51 |
| Lungs | 5 | 0.149 | 0.016 | 0.18 | 0.06 | 0.03 | 0.01 | 74.26 | 14.28 |
| Blood | 5 | 0.239 | 0.002 | 0.17 | 0.05 | 0.23 | 0.05 | 76.26 | 10.04 |
| Stomach | 5 | 0.334 | 0.041 | 0.04 | 0.01 | 0.01 | 0.01 | 299.09 | 55.84 |
| Sm Int | 5 | 0.882 | 0.064 | 0.06 | 0.02 | 0.06 | 0.02 | 207.34 | 42.11 |
| Lg Int | 5 | 0.793 | 0.090 | 0.13 | 0.11 | 0.11 | 0.10 | 126.67 | 55.69 |

TABLE 8

Time post Injection: 3 hr
Experiment Description: Pretargeting Bio with In-111-IMP-241 vs IMP-281 vs IMP-284
Group #: IIA ($^{125}$I --> 24 hrs -->$^{111}$In-IMP-281)
uCi injected: 6
Mean Body weight: 19.01

| Tissue | n | Weight | STD WT | % ID/g | STD % ID/g | % ID/org | STD % ID/org | T/NT | STD T/NT |
|---|---|---|---|---|---|---|---|---|---|
| | | | | MAb 1 isotope injected: I-125 | | | | | |
| | | | | MAb 1 injected: hMN-14 x m679 | | | | | |
| | | | | Corrected MAb 1 cpm injected: 9853618 | | | | | |
| Tumor | 4 | 0.529 | 0.049 | 5.38 | 0.82 | 2.85 | 0.53 | 1.00 | 0.00 |
| Liver | 4 | 0.874 | 0.148 | 0.90 | 0.21 | 0.77 | 0.10 | 6.12 | 1.02 |
| Spleen | 4 | 0.070 | 0.010 | 1.25 | 0.33 | 0.09 | 0.02 | 4.38 | 0.56 |
| Kidney | 4 | 0.119 | 0.011 | 0.61 | 0.15 | 0.07 | 0.01 | 9.10 | 1.40 |
| Lungs | 4 | 0.138 | 0.033 | 0.65 | 0.23 | 0.08 | 0.01 | 8.74 | 1.68 |
| Blood | 4 | 0.240 | 0.002 | 0.89 | 0.26 | 1.24 | 0.26 | 6.30 | 1.03 |
| Stomach | 4 | 0.337 | 0.066 | 6.98 | 3.33 | 2.26 | 1.00 | 0.94 | 0.50 |

TABLE 8-continued

Time post Injection: 3 hr
Experiment Description: Pretargeting Bio with In-111-IMP-241 vs IMP-281 vs IMP-284
Group #: IIA ($^{125}$I --> 24 hrs --> $^{111}$In-IMP-281)
uCi injected: 6
Mean Body weight: 19.01

| Tissue | n | Weight | STD WT | % ID/g | STD % ID/g | % ID/org | STD % ID/org | T/NT | STD T/NT |
|---|---|---|---|---|---|---|---|---|---|
| Sm Int | 4 | 0.980 | 0.153 | 0.36 | 0.11 | 0.34 | 0.08 | 15.87 | 3.44 |
| Lg Int | 4 | 0.694 | 0.137 | 0.59 | 0.19 | 0.40 | 0.13 | 9.83 | 2.94 |
| MAb 2 isotope injected: In-111 | | | | | | | | | |
| MAb 2 injected: IMP-281 | | | | | | | | | |
| MAb 2 cpm injected: 8149181.6 | | | | | | | | | |
| Tumor | 4 | 0.529 | 0.049 | 17.92 | 5.28 | 9.49 | 2.87 | 1.00 | 0.00 |
| Liver | 4 | 0.874 | 0.148 | 0.36 | 0.09 | 0.30 | 0.04 | 49.60 | 2.59 |
| Spleen | 4 | 0.070 | 0.010 | 0.37 | 0.11 | 0.03 | 0.01 | 48.46 | 2.10 |
| Kidney | 4 | 0.119 | 0.011 | 2.25 | 0.41 | 0.27 | 0.05 | 7.95 | 1.70 |
| Lungs | 4 | 0.138 | 0.033 | 0.56 | 0.13 | 0.07 | 0.01 | 31.88 | 3.82 |
| Blood | 4 | 0.240 | 0.002 | 0.89 | 0.28 | 1.25 | 0.29 | 20.28 | 1.19 |
| Stomach | 4 | 0.337 | 0.066 | 0.08 | 0.03 | 0.03 | 0.00 | 224.02 | 47.19 |
| Sm Int | 4 | 0.980 | 0.153 | 0.14 | 0.04 | 0.14 | 0.03 | 129.75 | 37.91 |
| Lg Int | 4 | 0.694 | 0.137 | 0.39 | 0.38 | 0.23 | 0.17 | 69.68 | 43.20 |

TABLE 9

Time post Injection: 24 hr
Experiment Description: Pretargeting Bio with In-111-IMP-241 vs IMP-281 vs IMP-284
Group #: IIB
uCi injected: 8.8
CPM Injected: 8605706.6
Mean Body weight: 20.69
Isotope injected: In-111
MAb injected: IMP-281

| Tissue | n | Weight | STD WT | % ID/g | STD % ID/g | % ID/org | STD % ID/org | T/NT | STD T/NT |
|---|---|---|---|---|---|---|---|---|---|
| Tumor | 5 | 0.306 | 0.085 | 0.026 | 0.002 | 0.008 | 0.002 | 1.000 | 0.000 |
| Liver | 5 | 1.085 | 0.136 | 0.035 | 0.005 | 0.038 | 0.006 | 0.753 | 0.102 |
| Spleen | 5 | 0.079 | 0.011 | 0.032 | 0.003 | 0.003 | 0.001 | 0.805 | 0.082 |
| Kidney | 5 | 0.131 | 0.010 | 1.068 | 0.133 | 0.140 | 0.017 | 0.024 | 0.003 |
| Lung | 5 | 0.141 | 0.009 | 0.017 | 0.005 | 0.002 | 0.001 | 1.660 | 0.423 |
| Blood | 5 | 0.239 | 0.001 | 0.000 | 0.000 | 0.000 | 0.000 | 346.489 | 269.842 |
| Stomach | 5 | 0.356 | 0.080 | 0.007 | 0.002 | 0.003 | 0.001 | 3.816 | 1.387 |
| Small Int. | 5 | 0.964 | 0.122 | 0.017 | 0.002 | 0.016 | 0.002 | 1.543 | 0.246 |
| Large Int. | 5 | 0.847 | 0.075 | 0.031 | 0.008 | 0.026 | 0.008 | 0.907 | 0.320 |

All Blood CPMs are 15 or less
All lung CPMs are 300 or less

TABLE 10

Time post Injection: 3 hr
Experiment Description: Pretargeting Bio with In-111-IMP-241 vs IMP-281 vs IMP-284
Group #: IIB
uCi injected: 8.8
CPM Injected: 10691556.6
Mean Body weight: 18.06
Isotope injected: In-111
MAb injected: IMP-281

| Tissue | n | Weight | STD WT | % ID/g | STD % ID/g | % ID/org | STD % ID/org | T/NT | STD T/NT |
|---|---|---|---|---|---|---|---|---|---|
| Tumor | 5 | 0.301 | 0.062 | 0.100 | 0.034 | 0.029 | 0.008 | 1.000 | 0.000 |
| Liver | 5 | 0.877 | 0.148 | 0.060 | 0.009 | 0.052 | 0.008 | 1.667 | 0.541 |
| Spleen | 5 | 0.070 | 0.015 | 0.040 | 0.005 | 0.003 | 0.001 | 2.481 | 0.722 |
| Kidney | 5 | 0.115 | 0.012 | 2.133 | 0.668 | 0.246 | 0.085 | 0.047 | 0.014 |
| Lung | 5 | 0.131 | 0.016 | 0.037 | 0.007 | 0.005 | 0.001 | 2.618 | 0.528 |
| Blood | 5 | 0.243 | 0.002 | 0.004 | 0.002 | 0.006 | 0.003 | 26.510 | 9.697 |
| Stomach | 5 | 0.361 | 0.097 | 0.032 | 0.013 | 0.011 | 0.006 | 3.744 | 2.828 |
| Small Int. | 5 | 0.819 | 0.140 | 0.082 | 0.045 | 0.069 | 0.046 | 1.627 | 1.183 |
| Large Int. | 5 | 0.611 | 0.062 | 0.295 | 0.119 | 0.178 | 0.065 | 0.418 | 0.278 |

All Blood CPMs are 180 or less

TABLE 11

Time post Injection: 30 min
Experiment Description: Pretargeting Bio with In-111-IMP-241 vs IMP-281 vs IMP-284
Group #: IIB
uCi injected: 8.8
CPM Injected: 10598413.3
Mean Body weight: 17.89
Isotope injected: In-111
MAb injected: IMP-281

| Tissue | n | Weight | STD WT | % ID/g | STD % ID/g | % ID/org | STD % ID/org | T/NT | STD T/NT |
|---|---|---|---|---|---|---|---|---|---|
| Tumor | 3 | 0.258 | 0.021 | 2.298 | 0.052 | 0.594 | 0.052 | 1.000 | 0.000 |
| Liver | 3 | 0.982 | 0.201 | 0.270 | 0.087 | 0.266 | 0.101 | 9.075 | 2.628 |
| Spleen | 3 | 0.080 | 0.018 | 0.257 | 0.081 | 0.020 | 0.008 | 9.629 | 3.393 |
| Kidney | 3 | 0.113 | 0.007 | 4.984 | 1.280 | 0.558 | 0.109 | 0.481 | 0.121 |
| Lung | 3 | 0.135 | 0.029 | 0.664 | 0.139 | 0.088 | 0.018 | 3.582 | 0.870 |
| Blood | 3 | 0.245 | 0.002 | 0.854 | 0.290 | 1.141 | 0.450 | 2.934 | 1.093 |
| Stomach | 3 | 0.393 | 0.094 | 0.171 | 0.079 | 0.063 | 0.024 | 16.758 | 10.840 |
| Small Int. | 3 | 0.888 | 0.161 | 0.441 | 0.112 | 0.387 | 0.103 | 5.479 | 1.562 |
| Large Int. | 3 | 0.655 | 0.098 | 0.240 | 0.196 | 0.169 | 0.161 | 14.223 | 8.914 |

TABLE 12

Time post Injection: 24 hr
Experiment Description: Pretargeting Bio with In-111-IMP-241 vs IMP-281 vs IMP-284
Group #: IIIA ($^{125}$I -> 24 hrs ->$^{111}$In-IMP-284)
uCi injected: 6
Mean Body weight: 19.84

| Tissue | n | Weight | STD WT | % ID/g | STD % ID/g | % ID/org | STD % ID/org | T/NT | STD T/NT |
|---|---|---|---|---|---|---|---|---|---|
| MAb 1 isotope injected: I-125 | | | | | | | | | |
| Mab 1 injected: hMN-14 x m679 | | | | | | | | | |
| Corrected MAb 1 cpm injected: 9788320 | | | | | | | | | |
| Tumor | 5 | 0.605 | 0.049 | 3.46 | 0.75 | 2.11 | 0.54 | 1.00 | 0.00 |
| Liver | 5 | 1.019 | 0.172 | 0.26 | 0.07 | 0.26 | 0.03 | 13.79 | 4.49 |
| Spleen | 5 | 0.075 | 0.015 | 0.28 | 0.05 | 0.02 | 0.00 | 12.44 | 3.45 |
| Kidney | 5 | 0.126 | 0.019 | 0.16 | 0.02 | 0.02 | 0.00 | 21.37 | 4.88 |
| Lungs | 5 | 0.150 | 0.022 | 0.16 | 0.02 | 0.02 | 0.00 | 21.88 | 5.72 |
| Blood | 5 | 0.242 | 0.002 | 0.20 | 0.03 | 0.30 | 0.03 | 17.28 | 4.44 |
| Stomach | 5 | 0.401 | 0.043 | 0.70 | 0.24 | 0.28 | 0.08 | 5.38 | 2.14 |
| Sm Int | 5 | 0.892 | 0.134 | 0.12 | 0.06 | 0.10 | 0.04 | 35.67 | 16.07 |
| Lg Int | 5 | 0.697 | 0.056 | 0.11 | 0.03 | 0.08 | 0.03 | 34.77 | 13.25 |
| MAb 2 isotope injected: In-111 | | | | | | | | | |
| MAb 2 injected: IMP-284 | | | | | | | | | |
| MAb 2 cpm injected: 4317976.6 | | | | | | | | | |
| Tumor | 5 | 0.605 | 0.049 | 11.58 | 2.17 | 7.00 | 1.46 | 1.00 | 0.00 |
| Liver | 5 | 1.019 | 0.172 | 0.40 | 0.08 | 0.40 | 0.05 | 29.76 | 7.51 |
| Spleen | 5 | 0.075 | 0.015 | 0.40 | 0.11 | 0.03 | 0.00 | 30.25 | 6.78 |
| Kidney | 5 | 0.126 | 0.019 | 1.80 | 0.16 | 0.22 | 0.02 | 6.45 | 1.18 |
| Lungs | 5 | 0.150 | 0.022 | 0.21 | 0.04 | 0.03 | 0.00 | 55.57 | 11.50 |
| Blood | 5 | 0.242 | 0.002 | 0.22 | 0.04 | 0.33 | 0.05 | 52.95 | 12.65 |
| Stomach | 5 | 0.401 | 0.043 | 0.04 | 0.02 | 0.02 | 0.01 | 303.88 | 103.30 |
| Sm Int | 5 | 0.892 | 0.134 | 0.08 | 0.02 | 0.07 | 0.01 | 155.54 | 34.18 |
| Lg Int | 5 | 0.697 | 0.056 | 0.07 | 0.01 | 0.05 | 0.01 | 166.52 | 42.08 |

TABLE 13

Time post Injection: 3 hr
Experiment Description: Pretargeting Bio with In-111-IMP-241 vs IMP-281 vs IMP-284
Group #: IIIA ($^{125}$I --> 24 hrs -->$^{111}$In-IMP-284)
uCi injected: 6
Mean Body weight: 19.39

| Tissue | n | Weight | STD WT | % ID/g | STD % ID/g | % ID/org | STD % ID/org | T/NT | STD T/NT |
|---|---|---|---|---|---|---|---|---|---|
| MAb 1 isotope injected: I-125 | | | | | | | | | |
| MAb 1 injected: hMN-14 x m679 | | | | | | | | | |
| Corrected MAb 1 cpm injected: 9853618 | | | | | | | | | |
| Tumor | 5 | 0.571 | 0.103 | 5.06 | 1.20 | 2.89 | 0.84 | 1.00 | 0.00 |
| Liver | 5 | 0.901 | 0.088 | 0.73 | 0.12 | 0.66 | 0.07 | 7.13 | 2.27 |

TABLE 13-continued

Time post Injection: 3 hr
Experiment Description: Pretargeting Bio with In-111-IMP-241 vs IMP-281 vs IMP-284
Group #: IIIA ($^{125}$I --> 24 hrs --> $^{111}$In-IMP-284)
uCi injected: 6
Mean Body weight: 19.39

| Tissue | n | Weight | STD WT | % ID/g | STD % ID/g | % ID/org | STD % ID/org | T/NT | STD T/NT |
|---|---|---|---|---|---|---|---|---|---|
| Spleen | 5 | 0.062 | 0.011 | 1.50 | 0.60 | 0.09 | 0.02 | 3.74 | 1.32 |
| Kidney | 5 | 0.124 | 0.004 | 0.50 | 0.09 | 0.06 | 0.01 | 10.52 | 3.36 |
| Lungs | 5 | 0.137 | 0.010 | 0.51 | 0.09 | 0.07 | 0.01 | 10.39 | 3.38 |
| Blood | 5 | 0.234 | 0.002 | 0.77 | 0.21 | 1.10 | 0.28 | 7.13 | 2.86 |
| Stomach | 5 | 0.432 | 0.163 | 3.45 | 1.91 | 1.32 | 0.53 | 2.03 | 1.54 |
| Sm Int | 5 | 0.906 | 0.178 | 0.32 | 0.07 | 0.29 | 0.06 | 16.60 | 5.97 |
| Lg Int | 5 | 0.716 | 0.122 | 0.45 | 0.20 | 0.32 | 0.12 | 13.56 | 7.60 |
| MAb 2 isotope injected: In-111 | | | | | | | | | |
| MAb 2 injected: IMP-284 | | | | | | | | | |
| MAb 2 cpm injected: 5380911.6 | | | | | | | | | |
| Tumor | 5 | 0.571 | 0.103 | 16.72 | 2.35 | 9.56 | 2.20 | 1.00 | 0.00 |
| Liver | 5 | 0.901 | 0.088 | 0.46 | 0.17 | 0.41 | 0.11 | 39.47 | 12.02 |
| Spleen | 5 | 0.062 | 0.011 | 0.82 | 0.42 | 0.05 | 0.02 | 23.55 | 8.10 |
| Kidney | 5 | 0.124 | 0.004 | 2.51 | 0.51 | 0.31 | 0.06 | 6.87 | 1.61 |
| Lungs | 5 | 0.137 | 0.010 | 0.68 | 0.10 | 0.09 | 0.01 | 24.87 | 3.94 |
| Blood | 5 | 0.234 | 0.002 | 1.13 | 0.40 | 1.61 | 0.53 | 16.42 | 6.27 |
| Stomach | 5 | 0.432 | 0.163 | 0.08 | 0.02 | 0.03 | 0.01 | 209.92 | 52.53 |
| Sm Int | 5 | 0.906 | 0.178 | 0.17 | 0.07 | 0.14 | 0.02 | 109.59 | 35.41 |
| Lg Int | 5 | 0.716 | 0.122 | 0.18 | 0.05 | 0.13 | 0.02 | 100.97 | 45.57 |

TABLE 14

Time post Injection: 24 hr
Experiment Description: Pretargeting Bio with In-111-IMP-241 vs IMP-281 vs IMP-284
Group #: IIIB
uCi injected: 8.8
Isotope injected: In-111
MAb injected: IMP-284
CPM Injected: 5380911.6
Mean Body weight: 19.71

| Tissue | n | Weight | STD WT | % ID/g | STD % ID/g | % ID/org | STD % ID/org | T/NT | STD T/NT |
|---|---|---|---|---|---|---|---|---|---|
| Tumor | 5 | 0.315 | 0.053 | 0.053 | 0.013 | 0.016 | 0.004 | 1.000 | 0.000 |
| Liver | 5 | 1.061 | 0.103 | 0.095 | 0.005 | 0.101 | 0.014 | 0.559 | 0.134 |
| Spleen | 5 | 0.070 | 0.004 | 0.071 | 0.009 | 0.005 | 0.001 | 0.744 | 0.161 |
| Kidney | 5 | 0.130 | 0.010 | 2.437 | 0.254 | 0.317 | 0.047 | 0.022 | 0.006 |
| Lung | 5 | 0.131 | 0.010 | 0.047 | 0.005 | 0.006 | 0.001 | 1.141 | 0.348 |
| Blood | 5 | 0.235 | 0.004 | 0.004 | 0.002 | 0.006 | 0.002 | 15.167 | 9.733 |
| Stomach | 5 | 0.367 | 0.066 | 0.027 | 0.016 | 0.010 | 0.006 | 2.441 | 1.365 |
| Small Int. | 5 | 0.970 | 0.071 | 0.038 | 0.012 | 0.036 | 0.011 | 1.464 | 0.429 |
| Large Int. | 5 | 0.829 | 0.093 | 0.071 | 0.032 | 0.060 | 0.033 | 0.808 | 0.253 |

All Blood CPMs are 75 or less
All Spleen CPMs are 375 or less
All Lung CPMs are 350 or less

TABLE 15

Time post Injection: 3 hr
Experiment Description: Pretargeting Bio with In-111-IMP-241 vs IMP-281 vs IMP-284
Group #: IIIB
uCi injected: 8.8
Isotope injected: In-111
MAb injected: IMP-284
CPM Injected: 6768496.6
Mean Body weight: 19.16

| Tissue | n | Weight | STD WT | % ID/g | STD % ID/g | % ID/org | STD % ID/org | T/NT | STD T/NT |
|---|---|---|---|---|---|---|---|---|---|
| Tumor | 5 | 0.306 | 0.076 | 0.255 | 0.081 | 0.075 | 0.023 | 1.000 | 0.000 |
| Liver | 5 | 0.908 | 0.050 | 0.155 | 0.024 | 0.140 | 0.022 | 1.708 | 0.709 |
| Spleen | 5 | 0.076 | 0.007 | 0.077 | 0.013 | 0.006 | 0.001 | 3.507 | 1.588 |
| Kidney | 5 | 0.122 | 0.012 | 4.359 | 0.531 | 0.533 | 0.086 | 0.059 | 0.018 |
| Lung | 5 | 0.151 | 0.019 | 0.149 | 0.135 | 0.022 | 0.019 | 2.732 | 1.914 |
| Blood | 5 | 0.235 | 0.002 | 0.021 | 0.026 | 0.029 | 0.036 | 23.725 | 13.540 |

TABLE 15-continued

Time post Injection: 3 hr
Experiment Description: Pretargeting Bio with In-111-IMP-241 vs IMP-281 vs IMP-284
Group #: IIIB
uCi injected: 8.8
Isotope injected: In-111
MAb injected: IMP-284
CPM Injected: 6768496.6
Mean Body weight: 19.16

| Tissue | n | Weight | STD WT | % ID/g | STD % ID/g | % ID/org | STD % ID/org | T/NT | STD T/NT |
|---|---|---|---|---|---|---|---|---|---|
| Stomach | 5 | 0.299 | 0.069 | 0.078 | 0.032 | 0.022 | 0.009 | 3.483 | 0.863 |
| Small Int. | 5 | 0.910 | 0.059 | 0.138 | 0.040 | 0.127 | 0.041 | 2.002 | 0.884 |
| Large Int. | 5 | 0.646 | 0.071 | 0.522 | 0.138 | 0.336 | 0.094 | 0.494 | 0.099 |

TABLE 16

Time post Injection: 30 min
Experiment Description: Pretargeting Bio with In-111-IMP-241 vs IMP-281 vs IMP-284
Group #: IIIB
uCi injected: 8.8
Isotope injected: In-111
MAb injected: IMP-284
CPM Injected: 6768496.6
Mean Body weight: 19.92

| Tissue | n | Weight | STD WT | % ID/g | STD % ID/g | % ID/org | STD % ID/org | T/NT | STD T/NT |
|---|---|---|---|---|---|---|---|---|---|
| Tumor | 2 | 0.294 | 0.016 | 2.515 | 0.590 | 0.743 | 0.214 | 1.000 | 0.000 |
| Liver | 2 | 0.939 | 0.072 | 0.506 | 0.194 | 0.482 | 0.219 | 5.122 | 0.797 |
| Spleen | 2 | 0.085 | 0.018 | 0.520 | 0.171 | 0.046 | 0.024 | 4.915 | 0.482 |
| Kidney | 2 | 0.127 | 0.003 | 6.705 | 0.699 | 0.851 | 0.070 | 0.373 | 0.049 |
| Lung | 2 | 0.148 | 0.002 | 1.310 | 0.367 | 0.193 | 0.051 | 1.933 | 0.091 |
| Blood | 2 | 0.233 | 0.001 | 1.725 | 0.965 | 2.560 | 1.487 | 1.615 | 0.561 |
| Stomach | 2 | 0.430 | 0.078 | 0.285 | 0.170 | 0.116 | 0.051 | 9.980 | 3.876 |
| Small Int. | 2 | 1.032 | 0.001 | 0.446 | 0.175 | 0.460 | 0.180 | 5.827 | 0.968 |
| Large Int. | 2 | 0.579 | 0.032 | 0.339 | 0.134 | 0.194 | 0.067 | 7.670 | 1.289 |

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," "more than" and the like include the number recited and refer to ranges which can be subsequently broken down into subranges as discussed above. In the same manner, all ratios disclosed herein also include all subratios falling within the broader ratio.

One skilled in the art will also readily recognize that where members are grouped together in a common manner, such as in a Markush group, the present invention encompasses not only the entire group listed as a whole, but each member of the group individually and all possible subgroups of the main group. Accordingly, for all purposes, the present invention encompasses not only the main group, but also the main group absent one or more of the group members. The present invention also envisages the explicit exclusion of one or more of any of the group members in the claimed invention.

It will be apparent to those skilled in the art that various modifications and variations can be made to the compositions and processes of this invention. Thus, it is intended that the present invention cover such modifications and variations, provided they come within the scope of the appended claims and their equivalents.

The disclosure of all publications disclosed herein are expressly incorporated herein by reference in their entireties to the same extent as if each were incorporated by reference individually.

Additional references of interest include the following:

Arano Y, Uezono T, Akizawa H, Ono M, Wakisaka K, Nakayama M, Sakahara H, Konishi J, Yokoyama A., "Reassessment of diethylenetriaminepentaacetic acid (DTPA) as a chelating agent for indium-111 labeling of polypeptides using a newly synthesized monoreactive DTPA derivative," *J Med Chem.* 1996 Aug. 30; 39(18):3451-60.

Bamias, A., and Epenetos, A. A. Two-step strategies for the diagnosis and treatment of cancer with bioconjugates. *Antibody, Immunoconjugates, Radiopharm.* 1992; 5: 385-395.

Barbet, J., Peltier, P., Bardet, S., Vuillez, J P., Bachelot, I., Denet, S., Olivier, P., Lecia, F., Corcuff, B., Huglo, D., Proye, C., Rouvier, E., Meyer,P., Chatal, J. F. Radioimmunodetection of medullary thyroid carcinoma using indium-111 bivalent hapten and anti-CEA×anti-DTPA-indium bispecific antibody. *J. Nucl. Med.* 1998; 39:1172-1178.

Bos, E S., Kuijpers, W H A., Meesters-Winters, M., Pham, D T., deHaan, A S., van Doormalen, Am., Kasperson, F. M., vanBoeckel, C A A and Gouegeon-Bertrand, F. In vitro evaluation of DNA-DNA hybridization as a two-step approach in radioimmunotherapy of cancer. *Cancer Res.* 1994; 54:3479-3486.

Carr et al., WO00/34317.

Gautherot, E., Bouhou, J., LeDoussal, J-M., Manetti, C., Martin, M., Rouvier, E., Barbet, J. Therapy for colon carcinoma xenografts with bi-specific antibody-targeted, iodine-131-labeled bivalent hapten. *Cancer suppl.* 1997; 80: 2618-2623.

Gautherot, E., Bouhou, J., Loucif, E., Manetti, C., Martin, M., LeDoussal, J. M., Rouvier, E., Barbet, J. Radioimmunotherapy of LS174T colon carcinoma in nude mice using an iodine-131-labeled bivalent hapten combined with an anti-CEA×anti-indium-DTPA bi-specific antibody. *J. Nucl. Med.* Suppl. 1997; 38: 7p.

Goodwin, D. A., Meares, C F., McCall, M J., McTigue, M., Chaovapong, W. Pre-targeted immunoscintigraphy of murine tumors with indium-111-labeled bifunctional haptens. *J. Nucl. Med.* 1988; 29:226-234.

Greenwood, F. C. and Hunter, W. M. The preparation of I-131 labeled human growth hormone of high specific radioactivity. *Biochem.* 1963; 89:114-123.

Hawkins, G. A., McCabe, R. P., Kim, C.-H., Subramanian, R., Bredehorst, R., McCullers, G. A., Vogel, C.-W., Hanna, M. G. Jr., and Pomata, N. Delivery of radionuclides to pretargeted monoclonal antibodies using dihydrofolate reductase and methotrexate in an affinity system. *Cancer Res.* 1993; 53: 2368-2373.

Kranenborg, M. h., Boerman, O. C., Oosterwijk-Wakka, j., weijert, M., Corstens, F., Oosterwijk, E. Development and characterization of anti-renal cell carcinoma×antichelate bi-specific monoclonal antibodies for two-phase targeting of renal cell carcinoma. *Cancer Res.*(suppl) 1995; 55: 5864s-5867s Losman M. J., Qu Z., Krishnan I. S., Wang J., Hansen H. J., Goldenberg D. M., Leung S. O. *Clin. Cancer Res.* 1999; 5(10 Suppl.):3101s-3105s.

Penefsky, H. S. A centrifuged column procedure for the measurement of ligand binding by beef heart F1. Part G. *Methods Enzymol.* 1979; 56:527-530.

Schuhmacher, J., Klivenyi, G., Matys, R., Stadler, M., Regiert, T., Hauser, H., Doll, J., Maier-Borst, W., Zoller, M. Multistep tumor targeting in nude mice using bi-specific antibodies and a gallium chelate suitable for immunocintigraphy with positron emission tomography. *Cancer Res.* 1995; 55, 115-123.

Sharkey, R M., Karacay, Griffiths, G L., Behr, T M., Blumenthal, R D., Mattes, M J., Hansen, H J., Goldenberg. Development of a streptavidin-anti-carcinoembryonic antigen antibody, radiolabeled biotin pretargeting method for radioimmunotherapy of colorectal cancer. Studies in a human colon cancer xenograft model. *Bioconjugate Chem* 1997; 8:595-604.

Stickney, D R., Anderson, L D., Slater, J B., Ahlem, C N., Kirk, G A., Schweighardt, S A and Frincke, J M. Bifunctional antibody: a binary radiopharmaceutical delivery system for imaging colorectal carcinoma. *Cancer Res.* 1991;51: 6650-6655.

All references cited herein are hereby incorporated herein by reference in their entireties.

The invention claimed is:

1. A compound comprising the formula: X—$R^1$-D-[Dpr, Orn or Lys](A)-$R^2$(Z)-D-[Dpr, Orn or Lys](B)—$R^3$(Y)—$NR^4R^5$; or $R^1$(X)-D-[Dpr, Orn or Lys](A)-$R^2$(Z)-D-[Dpr, Orn or Lys](B)—$R^3$(Y)—$NR^4R^5$, wherein:

X is a hard acid cation chelator, a soft acid cation chelator, or Ac—;

$R^1$ is a covalent bond or a D-amino acid selected from the group consisting of D-Tyr, D-Ala, D-Ser, D-Thr, D-Cys, D-Leu, D-Ile, D-Met, D-Gln, D-Val, D-Pro, D-His, D-Trp, D-Glu, D-Asp, and D-Lys;

$R^2$ is a covalent bond or a D-amino acid selected from the group consisting of D-Asp, D-Glu and D-Tyr;

$R^3$ is a covalent bond or D-Lys;

Y is a hard acid cation chelator, a soft acid cation chelator or is absent;

Z is a hard acid cation chelator, a soft acid cation chelator or is absent;

A and B independently are haptens or hard acid cation chelators and can be the same or different; and $R^4$ or $R^5$ is a therapeutic agent, diagnostic agent or enzyme.

2. The compound of claim 1, wherein the therapeutic agent, diagnostic agent or enzyme is covalently linked by a linker moiety.

3. The compound of claim 2, wherein the linker moiety comprises at least one amino acid.

4. The compound of claim 1, wherein the therapeutic agent comprises a drug, prodrug or toxin.

5. The compound of claim 4, wherein the prodrug is selected from the group consisting of epirubicin glucuronide, CPT-11, etoposide glucuronide, daunomicin glucuronide and doxorubicin glucuronide.

6. The compound of claim 4, wherein the toxin is selected from the group consisting of ricin, abrin, ribonuclease (RNase), DNase I, Staphylococcal enterotoxin-A, pokeweed antiviral protein, gelonin, diphtherin toxin, *Pseudomonas* exotoxin, and *Pseudomonas* endotoxin.

7. The compound of claim 1, wherein the therapeutic agent comprises doxorubicin, SN-38, camptothecin, etoposide, methotrexate, 6-mercaptopurine or etoposide phosphate.

8. The compound of claim 1, wherein the diagnostic agent comprises one or more agents for photodynamic therapy.

9. The compound of claim 8, wherein the agent for photodynamic therapy is a photosensitizer.

10. The compound of claim 1, wherein the diagnostic agent comprises one or more image enhancing agents for use in magnetic resonance imaging (MRI).

11. The compound of claim 10, wherein the enhancing agent comprises Mn, Fe, La or Gd.

12. The compound of claim 1, wherein the diagnostic agent comprises one or more radiopaque or contrast agents for X-ray or computed tomography.

13. The compound of claim 1, wherein the diagnostic agent comprises one or more ultrasound contrast agents.

14. The compound of claim 1, wherein the enzyme is capable of converting a drug intermediate to a toxic form to increase toxicity of the drug at a target site.

15. The compound of claim 1 wherein when $R^1$ or $R^3$ is a covalent bond then the other $R^1$ or $R^3$ is a D-amino acid.

16. The compound of claim 1 wherein R2 is selected from the group consisting of D-Asp, D-Glu, and D-Tyr.

17. The compound of claim 1, wherein $R^4$ or $R^5$ is a therapeutic agent.

18. The compound of claim 1, wherein $R^4$ or $R^5$ is a diagnostic agent.

19. The compound of claim 1, wherein R4 or $R^5$ is an enzyme.

* * * * *